United States Patent [19]

Sessler et al.

[11] Patent Number: 5,559,207
[45] Date of Patent: Sep. 24, 1996

[54] TEXAPHYRIN METAL COMPLEX MEDIATED ESTER HYDROLYSIS

[75] Inventors: Jonathan L. Sessler, Austin, Tex.; Daniel A. Smith, Goshen, Ind.; Richard A. Miller, Portola Valley, Calif.; Kevin L. Ross, Blue Ash, Ohio; Meredith Wright, San Jose; William C. Dow, Fremont, both of Calif.; Vladimir A. Král; Brent Iverson, both of Austin, Tex.; Darren Magda, Cupertino, Calif.

[73] Assignees: Board of Regents, University of Texas, Austin, Tex.; Pharmacyclics, Inc., Sunnyvale, Calif.

[21] Appl. No.: 227,370

[22] Filed: Apr. 14, 1994

Related U.S. Application Data

[63] Continuation-in-part of Ser. No. 75,123, Jun. 9, 1993, abandoned, which is a continuation-in-part of Ser. No. 822,964, Jan. 21, 1992, Pat. No. 5,252,720, which is a continuation-in-part of Ser. No. 771,393, Sep. 30, 1991, abandoned, which is a continuation-in-part of Ser. No. 539,975, filed as PCT/US90/01208, Mar. 6, 1990, Pat. No. 5,162,509, which is a division of Ser. No. 320,293, Mar. 6, 1989, Pat. No. 4,935,498.

[51] Int. Cl.[6] .................. C07K 2/00; C07K 16/00; C07H 3/00; C07F 5/00
[52] U.S. Cl. ............... 530/300; 530/387.1; 536/1.11; 536/23.1; 435/91.1; 435/135; 435/155; 534/11; 534/15; 534/16
[58] Field of Search ................ 530/387.1, 300; 536/23.1, 1.11; 534/11, 15, 16; 435/188.5, 91.1, 135, 155

[56] References Cited

U.S. PATENT DOCUMENTS

| | | | |
|---|---|---|---|
| 4,647,447 | 3/1987 | Gries et al. | 424/9 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235.2 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,162,509 | 11/1992 | Sessler et al. | 534/15 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1994 | Sessler et al. | 204/157.5 |
| 5,432,171 | 7/1995 | Sessler et al. | 514/185 |

FOREIGN PATENT DOCUMENTS

| | | |
|---|---|---|
| 0111418A2 | 6/1984 | European Pat. Off. |
| 0196515A1 | 10/1986 | European Pat. Off. |
| 0233701A2 | 8/1987 | European Pat. Off. |
| WO90/10633 | 9/1990 | WIPO |
| WO91/19730 | 12/1991 | WIPO |
| WO92/01781 | 2/1992 | WIPO |
| WO93/14093 | 7/1993 | WIPO |

OTHER PUBLICATIONS

Iverson, B. L., et. al. (1994) Pure Appl. Chem. 66(4), 845–850.

Magda, D., et. al. (1994) J. Am. Chem. Soc. 116, 7439–7440.

Mody, T. D., et al., "Lutetium(III) Texaphyrin: A Novel Photodynamic Therapy Agent", abstract, 22nd Annual American Society for Photobiology, Scottsdale, AR, Jun. 25–29, 1994.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

(List continued on next page.)

Primary Examiner—Charles L. Patterson, Jr.
Attorney, Agent, or Firm—Arnold, White & Durkee

[57] ABSTRACT

A method of phosphate ester hydrolysis including incubating a solution of an aqueous phosphate ester with a texaphyrin metal complex. The metal is a metal cation having catalytic activity for ester bond hydrolysis in aqueous solution, in particular, a lanthanide metal cation, preferably Eu(III) or Dy(III). A preferred substrate is RNA and a preferred texaphyrin is a derivatized texaphyrin having binding specificity, in particular, a texaphyrin covalently coupled to a site-directed molecule, preferably an oligonucleotide.

40 Claims, 24 Drawing Sheets

OTHER PUBLICATIONS

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," Tetrahedron Letters, 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with $(Lys)_2Cu$ as the Core Motif," *Journal of the Chemical Society*, 4:337–339, 1993.

Sessler and Burrell, "Expanded Porphyrins," *Topics in Current Chemistry*, 161:180–273, 1991.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3',5'–Cyclic Adenosine Monophosphate by Cerium(III) Hydroxide Cluster," *J. Chem. Soc. Chem. Comm.*, 2 pages, 1992.

To and Neiman, "The Potential For Effective Antisense Inhibition of Retroviral Replication Mediated by Retroviral Vectors," *Gene Regulation: Biology of Antisense RNA and DNA*, 261–271, 1992.

Shelton and Morrow, "Catalytic Transesterification and Hydrolysis of RNA by Zinc(II) Complexes," *Inorg. Chem.*, 30:4295–4299, 1991.

Sessler et al., "Synthesis and Structural Characterization of Lanthanide(III) Texaphyrins," *Inorganic Chemistry*, 32(14):3175–3187, 1993.

Abid et al., "Lanthanide Complexes of Some Macrocyclic Schiff Bases Derived from Pyridine–2,6–dicarboxaldehyde and $\alpha,\omega$–Primary Diamines", *Inorg. Chim. Acta*, 95:119–125, 1984.

Acholla et al., "Binucleating Tetrapyrrole Macrocycles", *J. Am. Chem. Soc.*, 107:6902–6908, 1985.

Acholla et al., "A Binucleating Accordian Tetrapyrrole Macrocycle", *Tetrahedron Lett.*, 25:3269–3270, 1984.

Ansell, "X–Ray Crystal Structure of the Pentagonal Bipyramidal Nickel(11) Complex $[Ni^{11}(L)(H_2O)_2](BF_4)_2$ and the Selective Stabilisation of the Nickel(1) Oxidation State by a Quinquedentate Macrocyclic Ligand", *J. Chem. Soc., Chem. Commun.*, 546–547, 1982.

Bauer et al., "Sapphyrins: Novel Aromatic Pentapyrrolic Macrocycles", *J. Am. Chem. Soc.*, 105:6429–6436, 1983.

Broadhurst et al., "Preparation of Some Sulphur–containing Polypyrrolic Macrocycles. Sulphur Extrusion from a meso–Thiaphlorin", *J. Chem. Soc., Chem. Commun.* 807–809, 1970.

Broadhurst et al., "18– and 22–$\pi$–Electron Macrocycles Containing Furan, Pyrrole, and Thiophen Rings", *J. Chem. Soc., Chem. Commun.*, 1480–1482, 1969.

Broadhurst et al., "New Macrocyclic Aromatic Systems Related to Porphins", *J. Chem. Soc., Chem. Commun.*, 23–24, 1969.

Broadhurst et al., "The Synthesis of 22 $\pi$–Electron Macrocycles. Sapphyrins and Related Compounds", *J. Chem. Soc. Perkin Trans.* 1, 2111–2116, 1972.

Cuellar et al., "Synthesis and Characterization of Metallo and Metal–Free Octaalkylphthalocyanines and Uranyl Decaalkysuperphthalocyanines", *Inorg. Chem.*, 20:3766–3770, 1981.

Day et al., "Large Metal Ion–Centered Template Reactions. A Uranyl Complex of Cyclopentakis (2–iminoisoindoline)", *J. Am. Chem. Soc.*, 97:4519–4527, 1975.

De Cola et al., "Hexaaza Macrocyclic Complexes of the Lanthanides", *Inorg. Chem.*, 25:1729–1732, 1986.

Dougherty, "Photosensitizers: Therapy and Detection of Malignant Tumors", *Photochem. Photobiol.*, 45:879–889, 1987.

Gossauer, "Synthesis of Some Unusual Polypyrrole Macrocyles", *Bull. Soc. Chim. Belg.*, 92:793–795, 1983.

Knubel et al., "Biomimetic Synthesis of an Octavinylogous Porphyrin with an Aromatic [34] Annulene System", *Angew. Chem., Int. Ed. Engl.*, 27:1170–1172, 1988.

Lauffer, "Paramagnetic Metal Complexes as Water Proton Relaxation Agents for NMR Imaging: Theory and Design", *Chem. Rev.* 87:901–927, 1987.

LeGoff et al., "Synthesis of a [1,5,1,5] Platyrin, a 26 $\pi$–Electron Tetrapyrrolic Annulene", *J. Org. Chem.*, 52:710–711, 1987.

Marks et al., "Large Metal Ion–Centered Template Reactions. Chemical and Spectral Studies of the Superphthalocyanine Dioxocyclopentakis (1–iminoisoindolinato) uranium (VI) and Its Derivatives", *J. Am. Chem. Soc.*, 100:1695–1705, 1978.

Rexhausen et al., "The Synthesis of a New 22 $\pi$–Electron Macrocycle: Pentaphyrin", *J. Chem. Soc., Chem. Commun.* pp. 275, 1983.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin-Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Tweedle et al., "Principles of Contrast-Enhanced MRI", in Magnetic Resonance Imaging, 2nd ed. Partain, et al, Eds., W. B. Saunders: Philadelphia, I:793–809, 1988.

Vogel et al., "Porphycene—a Novel Porphin Isomer", *Angew. Chem., Int. Ed. Engl.*, 25:257–259, 1986.

Vogel et al., "2,7,12,17-Tetrapropylporphycene—Counterpart of Octaethylporphyrin in the Porphycene Series", *Angew. Chem., Int. Ed. Engl.*, 26:928–931, 1987.

Sessler et al., "A Water-Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X-ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989.

Sessler et al., "Expanded Porphyrins: The synthesis and Metal Binding Properties of Novel Tripyrrane-Containing Macrocycles", *J. Coord. Chem.*, 18:99–104, 1988.

Sessler et al., "A Water-Stable Gadolinium (III) Complex Derived from a New Pentadentate", *Chem. Absts.*, vol. 111:125716e (2 Oct. 1989) p. 720.

Sessler et al., "The Synthesis and Structure of a Novel 22 π-Electron Aromatic Pentadentate Macrocyclic Ligand: An Expanded Porphyrin", Toronto ACS Meeting, Jun. 1988, Abst. 528.

Sessler et al., "'Texaphyrin': A Novel 22 π-Electron Aromatic Pentadentate Macrocyclic Ligand", ACS meeting, Los Angeles, Sep. 1988, Abst. 304.

Stinson, "Unusual Porphyrin Analog Promises Many Applications", *Chemical and Engineering News*, Aug. 8, 1988, pp. 26–27.

Sessler et al., "Tripyrroledimethine-derived (Texaphyrin--type Macrocycles: Potential Photosensitizers Which Absorb in the Far-red Spectral Region", *SPIE*, Optical Methods for Tumor Treatment and Early Diagnosis: Mechanism and Technique, 1426:318–329, 1991.

"2–Äthylamino–2–methyl–propanol–(1)", *Beilstein's Handbuch*, vol. 4 (1950) p. 785.

"Tentative Rules for Carbohydrate Nomenclature Part 1 (1969)," *Handbook of Biochemistry and Molecular Biology*, 3rd ed., Fasman, Ed., CRC Press, Cleveland, Ohio, pp. 100–102.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC, Abst. 300.

Sessler et al., "Synthesis and Applications of Schiff-Base Derived Expanded Porphyrins," *Abstracts of Papers*, Part 1, 204th ACS National Meeting, Aug. 23–28, 1992, Washington, DC, Abst. 111.

Sessler, Jonathan L., "Texas-Sized Molecule," *Discovery*, 13(1):44–49, 1993.

Sessler et al., "Photodynamic Inactivation of Enveloped Viruses Using Sapphyrin, 1 22 π-Electron Expanded Porphyrin: Possible Approaches to Prophylactic Blood Purification Protocols," *SPIE Photodynamic Therapy: Mechanisms II.* 1203:233–245, 1990.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer-Biochemie und Tumortherapeutische Erfahrungen," *Pharmazie*, 47:815–824, 1992.

Maiya et al., "Ground- and Excited-State Spectral and Redox Properties of Cadmium(II) Texaphyrin," *Journal of Physical Chemistry*, 93(24):8111–8115, 1989.

Sessler et al., "Texaphyrins: Synthesis and Application," *Accounts of Chemical Research*, 27(2):43–50, 1994.

Leff, "Texas 'Son-of-Porphyrin' Molecule Lassos Europium to Kill Drug Resistance Gene," *BioWorld Today*, 5(156):1, Mar., 1994.

8A R$_1$ = R$_2$ = OCH$_2$CH$_2$CH$_2$OH
8B R$_1$ = OCH$_2$CO$_2$H, R$_2$ = H
8C R$_1$ = OCH$_2$CO-DNA, R$_2$ = H

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | $O(CH_2)_3OH$ | $O(CH_2)_3OH$ |
| A2 | " | " | " | " | $O(CH_2CH_2O)_3CH_3$ | $O(CH_2CH_2O)_3CH_3$ |
| A3 | " | " | " | " | $O(CH_2)_nCON$-linker-site-directed molecule, n=1-7 | " |
| A4 | " | " | " | " | $O(CH_2)_nCON$-linker-site-directed molecule | H |
| A5 | " | " | " | " | $OCH_2CO$-poly-L-lysine | " |
| A6 | " | " | " | " | $OCH_2CO$-hormone | " |
| A7 | " | " | " | " | $O(CH_2CH_2O)_3CH_3$ | " |
| A8 | " | " | " | " | $OCH_2CON$-linker-site-directed molecule | " |
| A9 | " | " | " | " | $OCH_2CO$-hormone | $O(CH_2CH_2O)CH_3$ |
| A10 | " | " | " | " | $OCH_2CO$-hormone | " |

FIG. 13A

| TXP | $R_1$ | $R_2$ | $R_3$ | $R_4$ | $R_5$ | $R_6$ |
|---|---|---|---|---|---|---|
| A11 | " | " | " | " | $O(CH_2CH_2O)_{120}CH_3$ | " |
| A12 | " | " | " | " | saccharide | H |
| A13 | " | " | " | " | $OCH_2CON(CH_2CH_2OH)_2$ | " |
| A14 | " | " | " | " | $CH_2CON(CH_3)CH_2$-$(CHOH)_4CH_2OH$ | " |
| A15 | " | COOH | COOH | " | " | " |
| A16 | " | $COOCH_2CH_3$ | $COOCH_2CH_3$ | " | " | " |
| A17 | $CH_2CH_2CON(CH_2CH_2OH)_2$ | $CH_2CH_3$ | $CH_2CH_3$ | " | " | " |
| A18 | $CH_2CH_2ON(CH_3)CH_2$-$(CHOH)_4CH_2OH$ | " | " | " | $OCH^3$ | $OCH^3$ |
| A19 | $CH_2CH_3$ | " | " | " | $OCH^2CO^2$-glucosamine | H |
| A20 | $CH_2(CH_2)_2OH$ | " | " | " | $O(CH^2)^nCOOH, n=1-7$ | " |

FIG. 13B

| TXP | R$_1$ | R$_2$ | R$_3$ | R$_4$ | R$_5$ | R$_6$ |
|-----|-------|-------|-------|-------|-------|-------|
| A21 | " | " | " | " | (CH$_2$)$_n$-CON-linker-site-directed molecule, n=1-7 | " |
| A22 | " | " | " | " | YCOCH$_2$-linker-site-directed molecule Y=NH,O | " |
| A23 | CH$_2$CH$_3$ | CH$_3$ | CH$_2$CH$_2$CO OH | " | O(CH$_2$)$_2$CH$_2$OH | O(CH$_2$)$_2$CH$_2$O H |
| A24 | " | " | CH$_2$CH$_2$CO N-oligo | " | " | " |

FIG. 13C

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

CTCGGCCATA GCGAATGTTC                                                   20

( 2 ) INFORMATION FOR SEQ ID NO:2:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear (ii) MOLECULE TYPE: DNA (genomic)

(xi) SEQUENCE DESCRIPTION: SEQ ID NO:2:

CATCTGTGAG CCGGGTGTTG    20

(2) INFORMATION FOR SEQ ID NO:3:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: RNA (genomic)

(xi) SEQUENCE DESCRIPTION: SEQ ID NO:3:

GAACAUUCGC UAUGGCCGAG AAGAUGUCAC C    31

(2) INFORMATION FOR SEQ ID NO:4:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: RNA (genomic)

(xi) SEQUENCE DESCRIPTION: SEQ ID NO:4:

GAACAUUCGC UAUGGCCGAG AAGAUG    26

TEXAPHYRIN METAL COMPLEX MEDIATED ESTER HYDROLYSIS

Research leading to the present invention was supported in part by the National Science Foundation (CHE 9122161) and the National Institutes of Health (AI 33577 and AI 28845). The U.S. government therefore has certain rights in the invention.

This application is a continuation-in-part application of U.S. Ser. No. 08/075,123 filed Jun. 9, 1993, now abandoned. U.S. Ser. No. 08/075,123 is a continuation-in-part application of Ser. No. 07/822,964 filed Jan. 21, 1992, since issued as U.S. Pat. No. 5,252,720, Oct. 12, 1993. U.S. Ser. No. 07/822,964 was a continuation-in-part application of Ser. No. 07/771,393, filed Sep. 30, 1991, now abandoned, which was a continuation-in-part of Ser. No. 07/539,975, filed Jun. 18, 1990, since issued as U.S. Pat. No. 5,162,509 on Nov. 10, 1992 and a continuation of international application no. PCT/US90/01208, filed Mar. 6, 1990, now abandoned, U.S. Ser. No. 07/539,975 was a divisional application of U.S. Ser. No. 07/320,293, filed Mar. 6, 1989, since issued as U.S. Pat. No. 4,935,498, Jun. 19, 1990, All of the above-named patents and applications are incorporated by reference herein.

BACKGROUND OF THE INVENTION

The present invention relates to catalysts for the cleavage of ester bonds, in particular, phosphate ester bonds related to a biological system. An effective catalyst would have the following properties:

1) Efficiency at physiological temperature and pH;
2) Specificity for certain biological substrates;
3) Low toxicity for physiological systems; and
4) Easy administration to a biological system and ready subsequent elimination.

Various biologically important phosphate esters may be hydrolyzed according to the methods of the present invention, including RNA, DNA, phospholipids, phosphate anhydrides, UDP-glucose or a widely used substrate for assays, p-nitrophenylphosphate ester.

Many divalent and trivalent metal salts have been shown to promote the hydrolysis of phosphate ester bonds. Komiyama et al. (1992) reported the hydrolysis of adenylyl(3'-5')adenosine and uridyl(3'-5')uridine at pH 8.0, 30° C. by rare earth metal(III) ions. A Cerium(III) hydroxide cluster has been reported to hydrolyze 3',5'-cyclic adenosine monophosphate (Sumaoka, et al. 1992). Browne and Bruice (1992) reported the hydrolysis of bis(8-hydroxyquinoline)phosphate in the presence of divalent cations. However, in order to convey a degree of specificity to catalysis by the metal ion, complexes of metals with various ligands have been studied. The ligand may serve a number of roles in catalysis including, modulation of catalytic efficiency, and maintenance of the metal ion in solution, while also allowing for coupling of reagents having a binding specificity for a desired substrate.

Ligands complexing metal ions for use in the hydrolysis of phosphate ester bonds include: tris(aminopropyl)amine (trpn), 1,4,7,10-tetraazacyclododecane (cyclen), tris(2-aminoethyl)amine (tren), triethylenetetramine (trien), tetraethylenepentamine (tetren), bipyridine conjugates, imidazole, cyclodextrin derivatives, lysine, terpyridine (trpy), 1,2-diaminoethane, a bis(diaquo) complex, "metallomicelles" and a phenanthrolinepolyamine tridentate complex (Basile et al. 1987, Menger et al. 1987, Chung et al. 1990, Hendry and Sargeson, 1989, Shelton and Morrow, 1991, Ranganathan et al. 1993, Breslow and Huang, 1991, Modak et al. 1991, Kim and Chin, 1992, Chin et al. 1989, Chin and Banaszczyk, 1989a,b, Chin and Zou, 1987).

In order for a metal complex to function catalytically in vivo, the complex should not release bound metal ion. Morrow et al. (1992) have studied the cleavage of RNA by a lanthanide(III) hexamine Schiff-base (HAM) macrocyclic complex. Cleavage of the dinucleotide adenylyl-3',5'uridine 3'-monophosphate (ApUp) or of oligomers of adenylic acid (A12–A18) was reported at 37° C. after 4 hours by several lanthanide complexes. Other hexadentate ligands such as EDTA formed lanthanide(III) complexes that are completely inactive in RNA cleavage under similar conditions. Inertness of the macrocyclic complex to metal release was reported to change dramatically throughout the lanthanide series. These complexes have some serious disadvantages, including high toxicity of the HAM ligand, weak coordination and dissociation of the lanthanide metals. Further, the ligand cannot be easily modified which precludes the generation of derivatives with substrate specificity.

Given the limitations of the HAM complex, it is clear that the development of new macrocycles, capable of chelating lanthanide metals and forming stable complexes which are able to cleave RNA, would be of utility.

LIST OF ABBREVIATIONS

DEPC: Diethylpyrocarbonate
dm: decimeter
EDTA: Ethylenediamine tetraacetic acid
EuOAc: Eu(III)(acetate)$_3$
Txp (txph) (TX): Texaphyrin

SUMMARY OF THE INVENTION

The present invention seeks to solve these problems by providing texaphyrin metal complexes and texaphyrin metal complex-conjugates for ester hydrolysis that provide stable chelation for an otherwise toxic metallic cation, specificity for targeted sites in a therapeutic application, and sufficient nontoxicity for in vivo use.

The present invention involves the discovery that texaphyrin metal complexes catalyze the hydrolysis of ester linkages. Texaphyrins are unique molecules in that they chelate the metal in a very stable complex but allow access to the metal coordination sites, thus preserving the metal's reactivity and its ability to hydrolyze phosphoester bonds. Furthermore, the texaphyrin molecule allows for derivatization for various biological applications. The texaphyrin complex is far less toxic than the HAM ligand as well.

U.S. Pat. No. 5,252,720, incorporated herein by reference, demonstrated the stability and utility of texaphyrin metal complexes for in vivo use in magnetic resonance imaging protocols. The $Y^{3+}$, $Gd^{+3}$, and $In^{3+}$ complexes of texaphyrin were found to be hydrolytically stable in 1:1 methanol-water mixtures with half-lives for decomplexation and/or ligand decomposition exceeding 3 weeks in both cases. A T2B2 texaphyrin-gadolinium complex showed low toxicity and good tissue selectivity in magnetic resonance imaging enhancement. The texaphyrin metal complex-conjugates of the present invention are expected to have similar stability for chelating lanthanide metal cations and similar low toxicity for in vivo applications.

Texaphyrin metal complexes possess inherent biolocalization specificity as described in the '720 patent. In one embodiment of the present invention, the texaphyrin metal complexes are further coupled to site-directed molecules to form conjugates for targeted in vivo delivery. "Specificity for targeted sites" means that upon contacting the texaphyrin metal complex-conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific nucleotide, amino acid or glycolytic residues of the target to form a stable complex under the conditions effective to promote the interaction. In the present invention, this interaction will allow cleavage of an ester linkage that is in the vicinity of the specific binding.

Exemplary conjugates, or site-directed molecules, contemplated in the present invention include but are not limited to: polynucleotides and oligonucleotides such as antisense oligonucleotides, polyamides including peptides having affinity for a biological receptor and proteins such as antibodies, hormones such as estradiol, morphine or histamine and further macrocycles such as sapphyrins and texaphyrins.

A conjugate group having site specificity may be covalently coupled to a texaphyrin directly on the macrocycle ring or through various couples. A couple may be described as a linker, i.e. a reactive group for covalently attaching another molecule at a distance from the texaphyrin macrocycle. Exemplary linkers or couples are amides, thiols, thioether or ether covalent bonds as described in the examples for attachment of oligonucleotides and antibodies. In most preferred embodiments, conjugates and appended groups are covalently bonded to the texaphyrin via a carbon-carbon, carbon-nitrogen or a carbon-oxygen bond.

It will be apparent to one of skill in the art in light of the present disclosure that a variety of ester linkages may be cleaved by the molecules of the present invention. Exemplary ester linkages cleaved by the molecules of the present invention include phosphate monoester and diester linkages, especially physiologically important phosphate linkages present in nucleic acids such as RNA and DNA, important mediators of metabolism such as nucleotides ATP, ADP, AMP, cAMP, UDP, NADH, NADPH, FAD or $FADH_2$, for example, and phospholipids such as phosphatidyl choline and sphingomyelin that are important in nerve and brain functions.

An embodiment of the present invention provides a method of phosphate ester hydrolysis. The method comprises the steps of obtaining an aqueous phosphate ester solution, and incubating the solution with a texaphyrin metal complex, the incubation being under conditions and for a time sufficient to hydrolyze the phosphate ester. A texaphyrin metal complex as used herein is an aromatic pentadentate expanded porphyrin analog metal complex with appended functional groups. Such pendant groups may enhance solubility or biolocalization or may provide coupling sites for site-directed molecules.

The metal is a divalent or a trivalent metal cation having catalytic activity for ester bond hydrolysis in aqueous solution, in particular, the metal is a lanthanide cation a Lewis acidic cation such as Y(III), In(III), or Sc(III). Exemplary metals include lanthanum, cerium, praseodymium, neodymium, promethium, samarium, europium, gadolinium, terbium, dysprosium, holmium, erbium, thulium, ytterbium, lutetium, scandium or yttrium. In particular, the metal may be La(III), Nd(III), Sm(III), Gd(III), Tm(III), or Lu(III), or preferably, Eu(III) Lu(III) or Dy(III).

In a preferred embodiment, the phosphate ester is a nucleic acid ester. The aqueous phosphate ester solution may be a suspension of nucleic acid, for example, a solution or suspension of RNA or DNA. RNA is more preferably cleaved than DNA by a factor of about 100. When the phosphate ester is RNA, the metal is preferably Dy(III) or Eu(III).

The texaphyrin metal complex may be a water soluble compound having the structure:

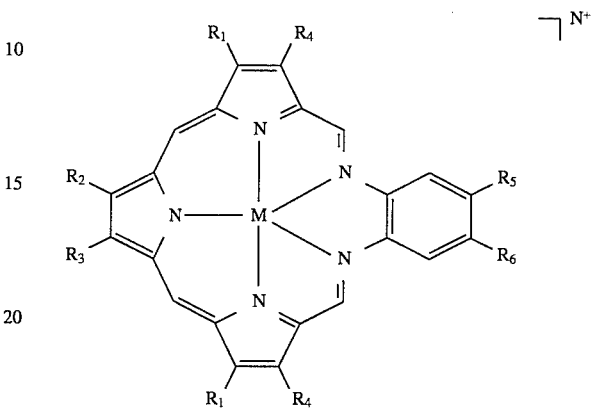

In this texaphyrin metal complex, M is a divalent or a trivalent metal cation catalyzing ester bond hydrolysis in aqueous solution. $R_1$, $R_2$, $R_3$, $R_4$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, a site-directed molecule or a couple to a site-directed molecule or to a catalytic group. A site-directed molecule is the conjugate of a texaphyrin metal complex-conjugate. A catalytic group is also the conjugate of a texaphyrin metal complex-conjugate and may include, but is not limited to, imidazole, guanidine or texaphyrin.

N will typically be an integer less than or equal to 2. In the context of the basic macrocycle with a divalent or trivalent metal cation, N is 1 or 2; however, with a site-directed molecule covalently attached, one skilled in the art in light of the present disclosure would realize that the value of N would be altered due to charges present on the site-directed molecule, for example, charges of the phosphate groups on an oligonucleotide.

Exemplary conjugates, or site-directed molecules, contemplated in the present invention include but are not limited to: polynucleotides and oligonucleotides such as antisense oligonucleotides, polyamides including peptides having affinity for a biological receptor and proteins such as antibodies, hormones such as estradiol, morphine or histamine and further macrocycles such as sapphyrins and texaphyrins.

$R_1$, $R_2$, $R_3$, $R_4$, $R_5$ and $R_6$ may also independently be amino, carboxy, carboxamide, ester, amide sulfonato, aminoalkyl, sulfonatoalkyl, amidealkyl, aryl, etheramide or equivalent structures conferring the desired properties. In a preferred embodiment, at least one of $R_1$, $R_2$, $R_3$, $R_4$, $R_5$ and $R_6$ is a site-directed molecule or is a couple to a site-directed molecule. For bulky R groups on the benzene ring portion of the molecule such as antibodies, peptides or oligonucleotides, one skilled in the art would realize that derivatization at one position on the benzene portion is more preferred.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, oxyhydroxyalkyl may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$. The oxyhydroxyalkyl or saccharide may be $C_nH_{(2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to $2n+1$, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directed molecule or catalytic group. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than $((2n+1)-q)$, q is zero or a positive integer less than or equal to $2n+1$, and $R^c$ is $(CH_2)_nCO_2R^d$, $(CH_2)_nCONHR^d$, $(CH_2)_nCON(R^d)_2$ or a site-directed molecule or catalytic group. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{(2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide. In a preferred embodiment, $R^c$ is an oligonucleotide.

In a preferred embodiment of the present invention, $R_1$, $R_2$, $R_3$, and $R_4$ are alkyl, or independently, $R_5$ and $R_6$ are H or alkyl. $R_3$ may be an oligonucleotide or may be a couple to an oligonucleotide. Further, $R_1$ may be $(CH_2)_2CH_2OH$, $R_2$ and $R_3$ may be $CH_2CH_3$, $R_4$ may be $CH_3$ and $R_5$ and $R_6$ may be $OCH_2CH_2CH_2OH$. $R_5$ may be $O(CH_2)_nCO$-oligonucleotide where n is preferably 1–3 and $R_6$ may be H. In a further preferred embodiment, $R_1$ may be $CH_2CH_2CH_2OH$, $R_2$ and $R_3$ may be $CH_2CH_3$, $R_4$ may be $CH_3$, $R_5$ may be $O(CH_2CH_2O)_2 CH_2CH_2OCH_3$ and $R_6$ may be a site-directed molecule or a couple to a site-directed molecule.

In a further embodiment of the present invention, at least one of $R_1$, $R_2$, $R_3$, $R_4$, $R_5$ and $R_6$ is a site-directed molecule or is a couple to a site-directed molecule. In a more preferred embodiment, the site-directed molecule is an oligonucleotide or is a couple to an oligonucleotide and most preferably, the oligonucleotide is a deoxyribonucleotide and the phosphate ester is RNA. The oligonucleotide has complementary binding affinity for the RNA in a region proximal to the phosphate ester bond being hydrolyzed. The oligonucleotide may have complementary binding affinity for viral RNA, in particular, retroviral RNA, or for bacterial ribosomal RNA, thereby cleaving the viral RNA or bacterial RNA and killing the organism. When the phosphate ester is RNA, the metal cation is preferably a lanthanide metal cation, more preferably, Eu(III) or Dy(III).

The oligonucleotide may be a deoxyribonucleotide and have complementary binding affinity for oncogenes. The oligonucleotide, antibody, hormone, sapphyrin or a second texaphyrin metal complex may have binding specificity for localization to a treatment site and the biological receptor may be localized to a treatment site.

Another embodiment of the present invention is a method of phosphate ester hydrolysis comprising the steps of i) obtaining an aqueous phosphate ester solution and ii) incubating the solution with a texaphyrin metal complex linked to a sapphyrin. Sapphyrins have binding specificity for phosphate esters as described in example 9. The incubation is under conditions and for a time sufficient to hydrolyze the phosphate ester.

One skilled in the art would recognize in light of the present disclosure that sapphyrin-conjugated texaphyrin metal complexes may be used in methods for generating singlet oxygen. Sapphyrin compounds are disclosed in U.S. Pat. Nos. 5,159,065 and 5,120,411, incorporated by reference herein.

Another embodiment of the present invention is a method for targeted intracellular mRNA hydrolysis. The method comprises the introduction into a cell of a texaphyrin metal complex coupled to an oligonucleotide having complementary binding affinity for a targeted RNA, whereby hydrolysis of the targeted mRNA is catalyzed by the texaphyrin metal complex. The mRNA may be transcribed from an oncogene or it may encode a growth factor. The mRNA may be a normal mRNA which needs to be destroyed, for example, due to improper timing of expression.

A method for inhibiting the expression of a gene in an animal comprising the administration to the animal of a texaphyrin metal complex-conjugate is a further embodiment of the present invention. The oligonucleotide may have complementary binding affinity for messenger RNA transcribed from said gene or may be complimentary to either strand of the DNA surrounding the gene or encoding the gene. The gene may be an oncogene or it may encode a growth factor. A further embodiment of the present invention is a method for inhibiting the expression of a gene in a particular tissue of an animal comprising administering to the animal a texaphyrin metal complex-conjugate having specificity for the tissue. The texaphyrin metal complex-conjugate may have appended an oligonucleotide complimentary to the target gene and a further appended tissue-specific molecule like estradiol, for example, or an antibody directed for said tissue or a peptide having affinity for a biological receptor on said tissue.

An embodiment of the present invention is a texaphryin having the structure:

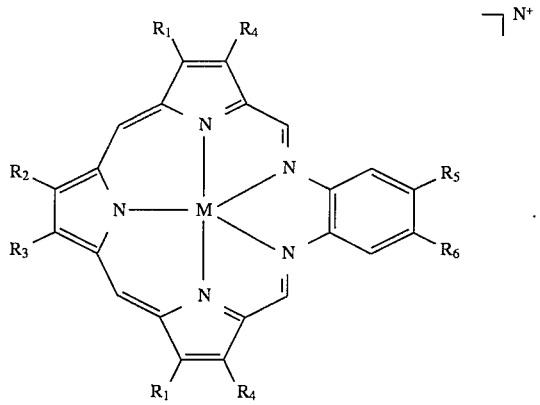

M may be H, a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2^{+2}$ or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$.

$R_1$, $R_2$, $R_3$, $R_4$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, a site-directed molecule or a couple to a site-directed molecule or to a catalytic group, and at least one of $R_1$, $R_2$, $R_3$, $R_4$, $R_5$ and $R_6$ is a site-directed molecule or a couple to a site-directed molecule or to a catalytic group. The terms, hydroxyalkyl, oxyalkyl, oxyhydroxyalkyl, saccharide, carboxyalkyl, carboxyamidealkyl, site-directed molecule, couple to a site-directed molecule, catalytic group and N are as previously described in this summary.

A preferred embodiment of the present invention is a texaphyrin metal complex-conjugate where the conjugate is a site-directed molecule. The site-directed molecule may be an antibody, a peptide having affinity for a biological receptor, an oligonucleotide, a hormone, a texaphyrin molecule or a sapphyrin molecule. More preferably, the site-directed molecule is an oligonucleotide where the oligonucleotide is a deoxyribonucleotide or is a couple to a deoxyribonucleotide. The oligonucleotide may have complementary binding affinity for oncogenes, for viral RNA or for retroviral RNA. Further, the oligonucleotide may have complementary binding affinity for a bacterial nucleic acid, for example, bacterial ribosomal RNA.

The metal cation may be a lanthanide metal cation and, more preferably, may be Eu(III) or Dy(III).

In preferred texaphyrins, $R_5$ is a site-directed molecule or a couple to a site-directed molecule or to a catalytic group and $R_6$ is H; $R_5$ is $O(CH_2)_nO$-oligonucleotide and n is 1–7; $R_1$ is $(CH_2)_2CH_2OH$, $R_2$ and $R_3$ are $CH_2CH_3$ and $R_4$ is $CH_3$; $R_1$ is $CH_2CH_2CH_2OH$, $R_2$ and $R_3$ are $CH_2CH_3$, $R_4$ is $CH_3$, $R_5$ is $O(CH_2CH_2O)_2CH_2CH_2OCH_3$ and $R_6$ is a site-directed molecule or a couple to a site-directed molecule or to a catalytic group; $R_6$ is $O(CH_2)_nO$-oligonucleotide and n is 1–7; or $R_1$–$R_6$ are as in FIG. 13A, FIG. 13B and FIG. 13C for texaphyrins A1–A24.

BRIEF DESCRIPTION OF THE DRAWINGS

FIG. 13A, FIG. 13B and FIG. 13C shows representative substituents for Texaphyrin macrocycles of the present invention.

DETAILED DESCRIPTION OF THE PREFERRED EMBODIMENTS

Figure 1A:
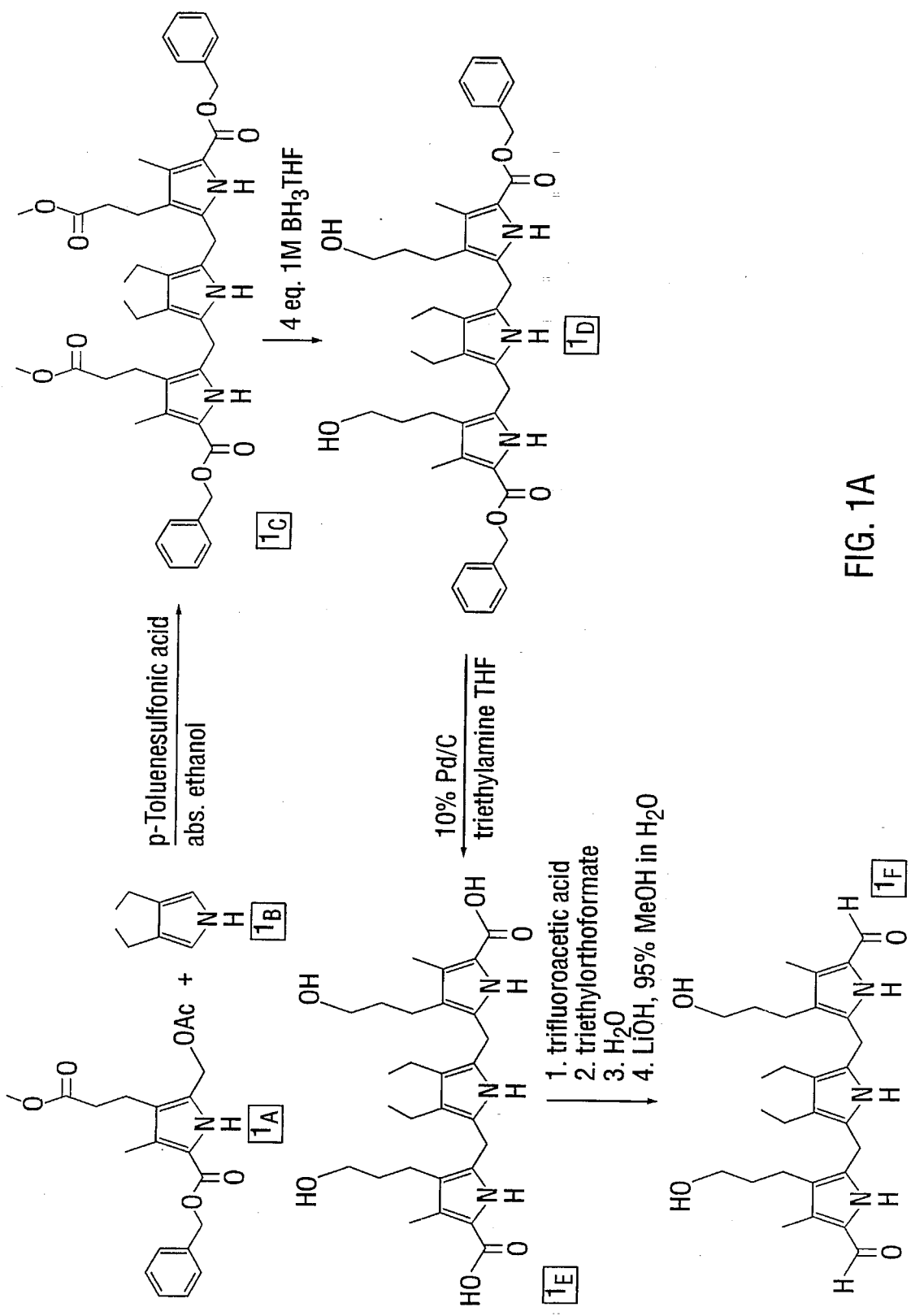
FIG. 1A, FIG. 1B, and FIG. 1C schematically summarize the synthesis of B2T2TXP($1_H$, $1_J$) and lanthanide metal complexes of B2T2, $1_J$–$1_W$.

The present invention involves the use of texaphyrin metal complexes, in particular, water soluble texaphyrin metal complexes for the cleavage of ester bonds. More particularly, the invention involves the cleavage of phosphate ester bonds of a diester, a monoester, an RNA and a DNA substrate using a lanthanide metal complex of a hydroxylated texaphyrin. Although a survey of lanthanide (III) texaphyrin complexes indicates that all of the metal complexes examined are capable of hydrolytically cleaving RNA, complexes of europium (III) and dysprosium (III) cleave RNA faster than other lanthanides of those tested thus far.

An individual skilled in the art of organic synthesis in light of the present disclosure is able to prepare a large variety of lanthanide texaphyrins, all of which are expected to hydrolytically cleave RNA, an important biological species. Potential particular applications for this process include the specific cleavage and possible subsequent recombination of RNA, destruction of viral RNA, digestion of cell membrane components such as phosphatidyl cholines and sphingomyelin, disruption of the transfer of free energy in cells by hydrolyzing ATP, ADP, NADH, NADPH, FAD or $FADH_a$, treatment of liver diseases by preventing the formation of glycogen, regulation of hormones by hydrolysis of cAMP, hydrolysis of mutagenic and carcinogenic di- and trialkyl phosphates commonly used as solvents, and the detoxification of phosphate ester nerve gases and insecticides by hydrolysis of phosphate ester bonds.

Texaphyrin compounds are described in U.S. Pat. Nos. 4,935,498, 5,162,509, 5,252,720, 5,272,142 and 5,256,399, each of which is incorporated by reference herein.

The introduction of hydroxy substituents on the B (benzene ring) portion of the texaphyrin molecule is accomplished by their attachment to phenylenediamine in the 4 and 5 positions of the phenyl subunit of the molecule or they may be added in a synthetic step following the condensation step that forms the macrocycle metal complex as described in the above-named patents. The introduction of hydroxy substituents on the T (tripyrrole or tripyrrane) portion of the molecule is accomplished by appropriate functionalization of the alkyl substituents in the 3 and/or 4 positions of the pyrrole rings at a synthetic step prior to condensation with the substituted phenylenediamine. Standard deprotection methodology such as ester hydrolysis may be used to unmask free hydroxyl substituents. Alternatively, they may be prepared as the result of ester reduction. These derivatives exhibit significant solubility in aqueous media, up to 1 mM or better, yet they retain affinity for lipid rich regions which allows them to be useful in biological environments.

Divalent and trivalent metal complexes of texaphyrins are by convention shown with a formal charge of $N^+$, where $N=1$ or 2, respectively. It is understood by those skilled in the art that the complexes described in the present invention have one or more additional ligands providing charge neutralization and/or coordinative saturation to the metal ion. Such ligands include chloride, nitrate, acetate, and hydroxide, among others.

Exemplary texaphyrins of the present invention are listed in FIG. 18.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Synthesis of B2T2 TXP, see FIG. 1A, FIG. 1B, and FIG. 1C 2,5-Bis[(5-benzyloxycarbonyl-4-methyl-3-methoxycarbonylethylpyrrol- 2-yl)methyl]-3,4-diethylpyrrole. $1_C$, FIG. 1A, FIG. 1B, and FIG. 1C.

In a 500 mL round bottom flask was placed 250 mL of ethanol from an unopened bottle and this was then purged with dry nitrogen for ten minutes. 3,4-Diethylpyrrole $1_B$ (1.29 g, 0.01 mol) and 2-acetoxymethyl-5-benzyloxycarbonyl-4-methyl-3-methoxycarbonylethylpyrrole $1_A$ (7.83 g, 0.02 mol) were added and the mixture heated until all of the pyrroles dissolved. p-Toluenesulfonic acid (65 mg) was added and the reaction temperature maintained at 60° C. The reaction slowly changed color from a clear yellow to a dark red with the product precipitating out of the solution as the reaction progressed. After ten hours the reaction was cooled to room temperature, the volume reduced to one half on a rotary evaporator, and then placed in the freezer for several hours. The product was collected by filtration, washed with a small amount of cold ethanol to afford 4.61 g of an off white fine powder (61%): $^1H$ NMR (CDCl$_3$, 250 MHz): δ1.14 (6H, t, CH$_2$CH$_3$), 2.23 (6H, s, pyrrole-CH$_3$), 2.31 (4H, t, CH$_2$CH$_2$CO$_2$CH$_3$), 2.50 (4H, q, CH$_2$CH$_3$), 2.64 (4H, t, CH$_2$CH$_2$CO$_2$CH$_3$), 3.60 (10H, br s, CH$_3$CO$_2$— and (pyrrole)$_2$—CH$_2$), 4.44 (4H, br s, C$_6$H$_5$CH$_2$), 6.99–7.02 (4H, m, aromatic), 7.22–7.26 (6H, m, aromatic), 8.72 (1H, s, NH), 10.88 (2H, br s, NH); $^{13}C$ NMR (CDCl$_3$, 250 MHz): δ10.97, 16.78, 17.71, 19.40, 22.07, 35.09, 51.46, 65.32, 117.37, 119.34, 122.14, 126.58, 126.79, 127.36, 128.19, 133.55, 136.62, 162.35, 173.49; CI MS (M+H)$^+$750; HRMS 749.3676 (calc. for C$_{44}$H$_{52}$N$_3$O$_8$: 749.3676).

2,5-Bis[(5-benzyloxycarbonyl-3-(3-hydroxypropyl)- 4-methylpyrrol-2yl)methyl]-3,4-diethylpyrrole. $1_D$, FIG. 1A, FIG. 1B, and FIG. 1C 2,5-Bis[(5-benzyloxycarbonyl-4-methyl-3 -methoxycarbonylethylpyrrol-2-yl)methyl]-3,4-diethylpyrrole $1_C$ (5.00 g, 0.007 mol) was placed in a three necked 100 mL round bottom flask and vacuum dried for at least 30 minutes. The flask was equipped with a thermometer, an addition funnel, a nitrogen inlet tube, and a magnetic stir bar. After the tripyrrane was partially dissolved into 10 mL of dry THF, 29 mL of borane (1M BH$_3$ in THF) was added dropwise with stirring. The reaction became mildly exothermic and was cooled with a cool water bath. The tripyrrane slowly dissolved to form a homogeneous orange solution which turned to a bright fluorescent orange color as the reaction went to completion. After stirring the reaction for one hour at room temperature, the reaction was quenched by adding methanol dropwise until the vigorous effervescence ceased. The solvents were removed under reduced pressure and the resulting white solid redissolved into CH$_2$Cl$_2$. The tripyrrane was washed three times with 0.5M HCl (200 mL total), dried over anhydrous K$_2$CO$_3$, filtered, and the CH$_2$Cl$_2$ removed under reduced pressure until crystals of the tripyrrane just started to form. Hexanes (50 mL) was added and the tripyrrane allowed to crystallize in the freezer for several hours. The product was filtered and again recrystallized from CH$_2$Cl$_2$/ethanol. The product was collected by filtration and vacuum dried to yield 3.69 g of an orangish white solid (76%): mp 172°–173° C.; $^1H$ NMR (CDCl$_3$, 300 MHz): δ1.11 (6H, t, CH$_2$CH$_3$), 1.57 (4H, p, CH$_2$CH$_2$CH$_2$OH), 2.23 (6H, s, pyrrole-CH$_3$), 2.39–2.49 (8H, m, CH$_2$CH$_3$ and CH$_2$CH$_2$CH$_2$OH), 3.50 (4H, t, CH$_2$CH$_2$CH$_2$OH), 3.66 (4H, s, (pyrrole)$_2$—CH$_2$), 4.83 (4H, s, C$_6$H$_5$—CH$_2$), 7.17–7.20 (4H, m, aromatic), 7.25–7.30 (6H, m, aromatic), 8.64 (1H, s, NH), 9.92 (2H, s, NH); $^{13}C$ NMR (CDCl$_3$, 300 MHz): δ10.97, 16.72, 17.68, 20.00, 22.38, 33.22, 62.01, 65.43, 117.20, 119.75, 120.72, 122.24, 127.23,127.62, 128.30, 132.95, 136.60, 162.13; FAB MS (M$^+$) 693.

2,5-Bis[(3-(3-hydroxypropyl)-5-carboxyl-4-methylpyrrol-2-yl) methyl]-3,4-diethylpyrrole $1_E$. FIG. 1A, FIG. 1B, and FIG. 1C 2,5-Bis[(3-(3 -hydroxypropyl)-5-benzyloxycarbonyl-4-methylpyrrol-2-yl)methyl]- 3,4-diethylpyrrole $1_D$ (15.0 g, 0.02 mol) was placed in a 1 L round bottom flask and dried in vacuo for ca. 30 min. The tripyrrane was dissolved in dry THF (600 mL) with triethylamine (10 drops) and 10% Pd on carbon (600 mg) and the reaction was stirred at room temperature under one atmosphere of H$_2$. After 15 h, the suspension was filtered through celite to remove the catalyst and the resulting clear solution was concentrated under reduced pressure to yield a light pink solid. This material, obtained in near quantitative yield, was taken on to the next step without further purification.

2,5-Bis[(5-formyl-3-(3-hydroxypropyl)-4-methylpyrrol-2-yl) methyl]-3,4-diethylpyrrole $1_F$, FIG. 1A, FIG. 1B, and FIG. 1C 2,5-Bis[(3-(3 -(hydroxypropyl)-5-carboxyl-4-methylpyrrol-2-yl)methyl]-3,4 -diethylpyrrole $1_E$ (10 g, 0.02 mol) was placed in a 250 mL round bottom flask and dried in vacuo for ca. 1 h. At room temperature under nitrogen, trifluoroacetic acid (31 mL, 0.40 mol) was added dropwise via syringe. The tripyrrane dissolved with visible evolution of $CO_2$ to form a homogeneous yellow solution. The reaction was stirred at room temperature for ca. 15 min, then cooled to −20° C. using a dry ice/$CCl_4$ bath. Freshly distilled triethylorthoformate (31 mL, 0.20 mol, dried over $CaH_2$) was added via a syringe to produce a dark orange/yellow solution. This mixture was stirred an additional 10 min at −20° C., then the cold bath was removed and 100 mL of distilled water was added dropwise to the solution. The resulting brown suspension was stirred at room temperature for 15 min. The product was collected by filtration, washed several times with water and re-suspended into a 50 mL/100 mL/50 mL ($H_2O$:EtOH:$NH_4OH$, v/v) mixture. The yellow/brown suspension was stirred for 1 h, filtered, washed several times with water, and then rinsed with a small amount of cold 95% ethanol. At this point, TLC analysis shows a mixture of tripyrranes. Therefore, the crude dialdehyde tripyrrane and LiOH.$H_2O$ (2.10 g, 0.05 mol) were added to 400 mL of degassed 95% MeOH and the suspension heated to reflux under a $N_2$ atmosphere. The reaction became homogeneous when heated and after ca. 1 h, it was slowly cooled to room temperature. The reaction mixture was concentrated under reduced pressure to 75 mL and the resulting slurry placed in the freezer for several hours. The product was filtered and then purified by forming a slurry with 400 mL of methanol and 50 mL of water and heating close to boiling. The suspension was slowly cooled to room temperature, reduced to 150 mL under reduced pressure, and placed in the freezer for several hours. The purified dialdehyde tripyrrane was filtered, rinsed with water and dried in vacuo for 24 h to yield 7.65 g (80%) of a light tan powder. For $1_F$: mp 164°–166° C.; $^1$H NMR ($CD_3OD$): δ0.96 (t, 6H, $CH_2CH_3$), 1.49 (p, 4H, $CH_2CH_2CH_2OH$), 2.25 (s, 6H, pyrr-$CH_3$), 2.32–2.43 (m, 8H, $CH_2CH_3$ and $CH_2CH_2CH_2OH$), 3.46 (t, 4H, $CH_2CH_2CH_2OH$), 3.85 (s, 4H, (pyrr)$_2$—$CH_2$), 9.34 (s, 2H, CHO); CI MS, M$^+$: m/e 480; HR MS, M$^+$: m/e 481.2942 (calcd. for $C_{28}H_{39}N_3O_4$, 481.2941).

Figure 1B:
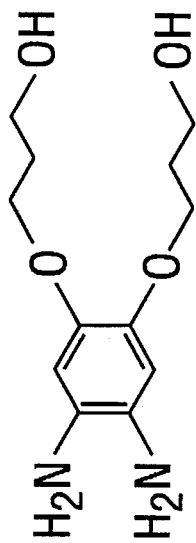
Figure 1B:
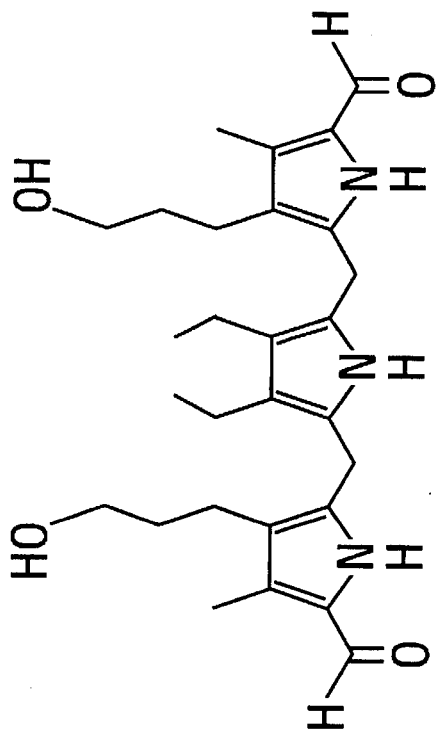
Figure 1C:
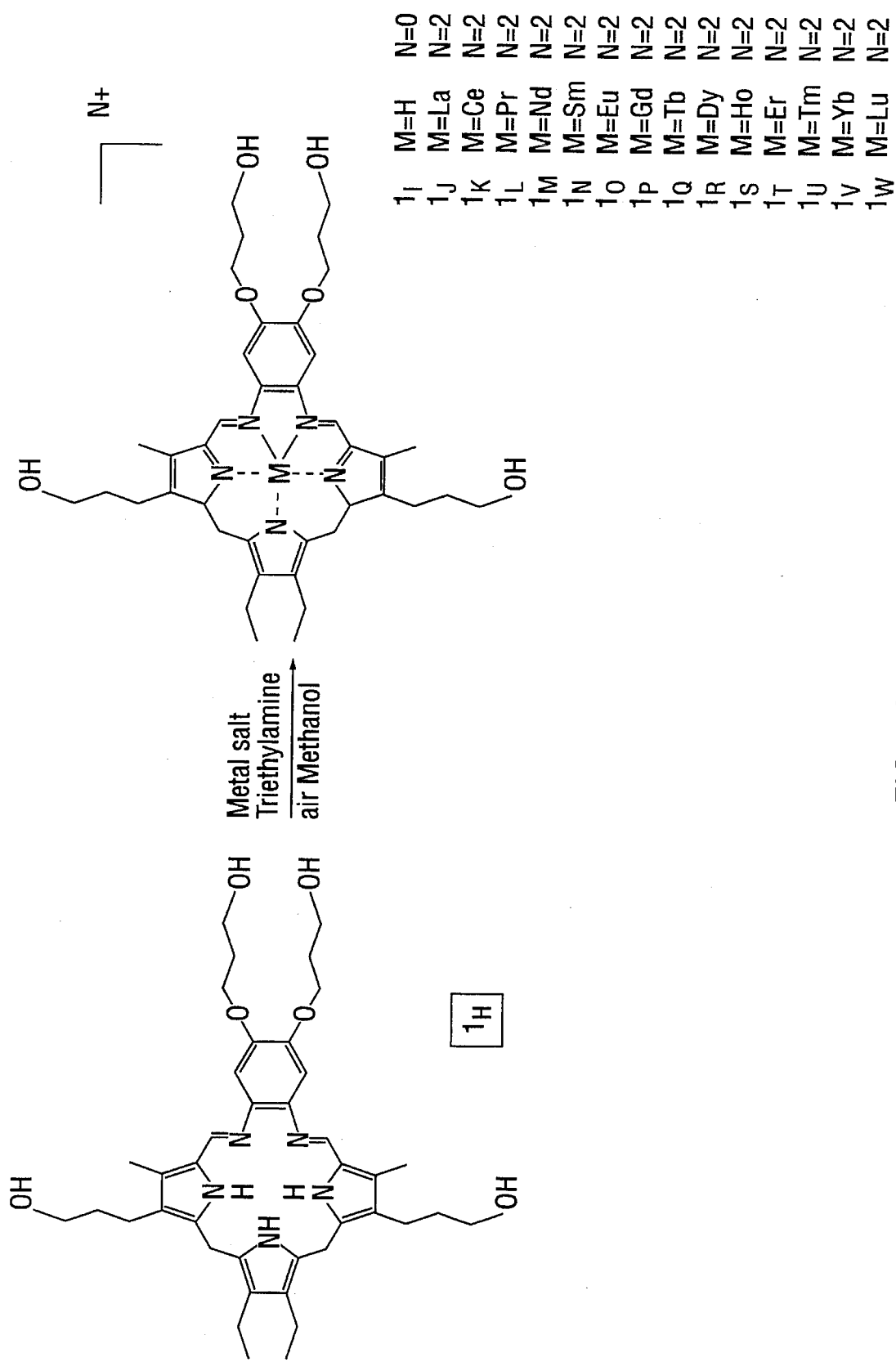

4,5-Diethyl-10,23-dimethyl-9,24-bis(3-hydroxypropyl)-16,17-bis( 3-hydroxypropyloxy)-13,20,25,26,27-pentaazapentacyclo [20.2.1.1$^{3,6}$.1$^{8,11}$.0$^{14,19}$]heptacosa-3,5,8,10,12,14,16,18,20,22,24-undecaene ( $1_H$, FIG. 1A, FIG. 1B, and FIG. 1C)

2,5-Bis[(5-formyl-3-(3-hydroxypropyl)-4 -methylpyrrol-2-yl)methyl]-3,4-diethylpyrrole $1_F$ (1.00 g, 0.002 mol) and 1,2-diamino-4,5-bis(3-hydroxy-propyloxy)benzene $1_G$ (0.52 g, 0.002 mol) were placed in a 2 L round bottom flask with 1000 mL of toluene and 200 mL of methanol. The solvents were purged with nitrogen prior to use. Concentrated HCl (0.5 mL) was added and the reaction heated to reflux under nitrogen. The reaction went from a clear suspension of starting materials to a dark red homogeneous solution as the reaction proceeded. After 5 h the reaction was cooled to room temperature and the solvents removed under reduced pressure until the product precipitated out of solution. The remainder of the solvent was decanted off and the macrocycle dried in vacuo. The dark red product was recrystallized from methanol/diethylether and yielded 1.4–1.5 g (90–100%). For $1_H$: mp 190° C. dec; $^1$H NMR ($CD_3OD$): δ1.11 (t, 6H, $CH_2CH_3$), 1.76 (p, 4H, pyrr-$CH_2CH_2CH_2OH$), 2.03 (p, 4H, $OCH_2CH_2CH_2OH$), 2.36 (s, 6H, pyrr-$CH_3$), 2.46 (q, 4H, $CH_2CH_3$), 2.64 (t, 4H, pyrr-$CH_2CH_2CH_2OH$), 3.61 (t, 4H, pyrr-$CH_2CH_2CH_2OH$), 3.77 (t, 4H, $OCH_2CH_2CH_2OH$), 4.10 (s, 4H, (pyrr)$_2$—$CH_2$), 4.22 (t, 4H, $OCH_2CH_2CH_2OH$), 7.41 (s, 2H, PhH), 8.30 (s, 2H, HC=N); $^{13}$C NMR ($CD_3OD$): δ10.0, 17.2, 18.6, 20.9, 24.5, 33.2, 33.5, 59.6, 61.9, 67.8, 107.1, 120.7 123.8, 125.0, 125.8, 128.7, 144.8, 145.0, 150.7, 154.6; UV/vis ($CH_3OH$) [$\lambda_{max}$, nm] 365; FAB MS, (M+H)$^+$: m/e 703; HRMS, M$^+$: m/e 701.4120 (calcd. for $C_{40}H_{55}N_5O_6$: 701.4152). Anal. calcd. [$C_{40}H_{55}N_5O_6$] (HCl) ($CH_3OH$): C, 63.92; H, 7.85; N, 9.09; Cl, 4.60. Found: C, 64.17; H, 7.68; N, 9.39; Cl, 4.70.

General procedure for the synthesis of water soluble lanthanide (III) 4,5-diethyl-10,23-dimethyl-9,24-bis(3-hydroxypropyl)- 16,17-(3-hydroxypropyloxy)-13,20,25,26,27-pentaazapentacyclo[20.2.1.1$^{3,6}$.1$^{8,11}$.0$^{14,19}$]heptacosa- 1,3,5,7,9,11(27),12,14,16,18,20,22(25),23-tridecaene, B2T2TXP ($1_I$, FIG. 1A, FIG. 1B, and FIG. 1C)

One equivalent of the hydrochloride salt of the macrocycle, 4,5-diethyl-10,23-dimethyl-9,24-bis(3-hydroxypropyl)- 16,17-bis(3-hydroxypropyloxy)-13,20,25,26,27-pentaazapentacyclo [20.2.1.1$^{3,6}$.1$^{8,11}$.0$^{14,19}$]heptacosa-3,5,8,10,12,14,16,18,20,22,24-undecaene $1_H$, 1.5 equivalents of the Ln(NO$_3$)$_3$.X$H_2O$ metal salt, 2–3 equivalents of tetrabutylammonium nitrate (TBANO$_3$) and triethylamine (ca. 1 mL) were mixed together in methanol and heated to reflux under air. After completion of the reaction (as judged by the UV/vis spectrum of the reaction mixture), the deep green solution was cooled to room temperature, the solvent removed under reduced pressure and the crude complex dried in vacuo for several hours. A solution of dichloromethane/methanol (99:1 v/v) was added to the crude complex and the suspension was sonicated a few min. The green suspension was filtered in order to remove red/brown colored impurities in the filtrate (incomplete oxidation products and excess triethylamine). The resulting deep green solid was first dissolved in methanol and then chloroform was added to reduce the polarity of the mixture (1:2 v/v). This solution was filtered through celite and loaded on a (pre-treated/pre-washed 1M NaNO$_3$) neutral alumina column (10 cm). The column was first eluted with a 1:10 (v/v) methanol/chloroform solution by gravity to remove a reddish brown impurity. The metal complex was then obtained by eluting the column with chloroform containing increasing amounts of methanol (20–50%). The purified lanthanide (III) texaphyrin complex was recrystallized by dissolving the complex in methanol/chloroform and carefully layering the dark green solution with a small amount of methanol, then with diethylether. The layered solution was kept at room temperature in the dark for a few days. Some of the lanthanide (III) texaphyrin complexes formed single crystals by this method. Other complexes were recrystallized twice for analytically pure measurements and characterizations.

Lanthanum(III) complex, $1_J$

The hydrochloride salt of macrocycle $1_H$ (300 mg, 0.407 mmol), La(NO$_3$)$_3$.6$H_2O$ (350 mg, 0.814 mmol), TBANO$_3$ (305 mg, 1.0 mmol) and triethylamine (ca. 0.5 mL) in 350 mL methanol were heated to reflux under air for 10 h. After workup using the general procedure outlined above, 132 mg of the complex was obtained (34%). For $1_J$: $^1$H NMR ($CD_3OD$): δ1.68 (t, 6H, $CH_2CH_3$), 2.22 –2.30 (m, 4H, pyrr-$CH_2CH_2CH_2OH$ and 4H, $OCH_2CH_2CH_2OH$), 3.20 (s, 6H, pyrr-$CH_3$), 3.72–3.78 (m, 4H, $CH_2CH_3$ and 4H, pyrr-$CH_2CH_2CH_2OH$ and 4H, pyrr-$CH_2CH_2CH_2OH$), 3.94 (t, 4H, $OCH_2CH_2CH_2OH$), 4.78 (m, 4H, $OCH_2CH_2CH_2OH$), 9.37 (s, 2H, ArH), 9.87 (s, 2H, (pyrr)$_2$C=CH), 11.71 (s, 2H, HC=N); $^{13}$C NMR (CD$_3$OD): δ11.0, 18.9, 20.3, 23.0, 33.3, 36.3, 59.7, 62.2, 68.1, 101.5, 118.5, 137.1, 140.3, 144.6, 147.5, 148.2, 152.9, 154.9, 159.4; UV/vis: [(MeOH) λ$_{max}$, nm (log ε)]: 355 (4.34), 417 (4.73), 476 (5.06), 685.5 (4.08), 746 (4.59); FAB MS, M$^+$: m/e 835; HRMS, (M+H)$^+$: m/e 836.2919 (calcd. for C$_{40}$H$_{51}$N$_5$O$_6$$^{139}$La, 836.2903). Anal. calcd. for [C$_{40}$H$_{50}$N$_5$O$_6$La] (NO$_3$)$_2$(H$_2$O)$_2$: C, 48.23; H, 5.47; N, 9.85. Found: C, 47.93; H, 5.41; N, 9.77.

Cerium(III) complex $1_K$

The hydrochloride salt of macrocycle $1_H$ (300 mg, 0.407 mmol), Ce(NO$_3$)$_3$·6H$_2$O (265 mg, 0.611 mmol), TBANO$_3$ (305 mg, 1.0 mmol) and triethylamine (ca. 0.5 mL) in 350 mL methanol were heated to reflux under air for 7 h. It is important to note that initially the reaction mixture formed a suspension, however, as the product formed the solution became homogeneous. After workup using the general procedure outlined above, 143 mg of dark green crystals were obtained (37%). This material was suitable for X-ray diffraction analysis. For $1_K$: UV/vis: [(MeOH) λ$_{max}$, nm (log ε)]: 349.5 (4.34), 416.5 (4.70) 476.5 (5.05), 684 (4.07), 741 (4.56); FAB MS, M$^+$: m/e 836; HRMS, (M+H)$^+$: m/e 836.2807 (calcd. for C$_{40}$H$_{51}$N$_5$O$_6$$^{140}$Ce, 836.2816). Anal. calcd. for [C$_{40}$H$_{50}$N$_5$O$_6$Ce] (NO$_3$)$_2$(H$_2$O)$_3$: C, 47.32; H, 5.56; N, 9.66. Found: C, 46.98; H, 5.22; N, 9.63.

Praseodymium(III) complex $1_L$

The hydrochloride salt of macrocycle $1_H$ (300 mg, 0.407 mmol), Pr(NO$_3$)$_3$·5H$_2$O (255 mg, 0.611 mmol), TBANO$_3$ (305 mg, 1.0 mmol) and triethylamine (ca. 0.5 mL) in 350 mL methanol were heated to reflux under air for 10 h. After workup using the general procedure outlined above, 200 mg of the complex was obtained (51%). For $1_L$: UV/vis: [(MeOH) λ$_{max}$, nm (log ε)]: 352 (4.32), 416.5 (4.69), 476.5 (5.04), 689 (4.07), 744.5 (4.57); FAB MS, M$^+$: m/e 838; HRMS, M$^+$: m/e 837.2823 (calcd. for C$_{40}$H$_{50}$N$_5$O$_6$$^{141}$Pr, 837. 2838). Anal. calcd. for [C$_{40}$H$_{50}$N$_5$O$_6$Pr] (NO$_3$)$_2$(CH$_2$OH) (H$_2$O): C, 48.65; H, 5.58; N, 9.69. Found: C, 48.75; H, 5.52; N, 9.71.

Neodymium(III) complex $1_M$

The hydrochloride salt macrocycle $1_H$ (300 mg, 0.407 mmol), Nd(NO$_3$)$_3$·6H$_2$O (267 mg, 0.611 mmol), TBANO$_3$ (305 mg, 1.0 mmol) and triethylamine (ca. 0.5 mL) in 350 mL methanol were heated to reflux under air for 12 h. After workup using the general procedure outlined above, 125 mg of the complex was obtained (32%). For $1_M$: UV/vis: [(MeOH) λ$_{max}$, nm (log ε)]: 353.5 (4.32), 416 (4.68), 476 (5.05), 688 (4.06), 742.5 (4.56); FAB MS, M$^+$: m/e 839; HRMS, M$^+$: m/e 838.2828 (calcd. for C$_{40}$H$_{50}$N$_5$O$_6$$^{142}$Nd, 838.2838). Anal. calcd. for [C$_{40}$H$_{50}$N$_5$O$_6$Nd] (NO$_3$)$_2$(CH$_3$OH): C, 49.48; H, 5.47; N, 9.86. Found: C, 49.23; H, 5.49; N, 9.83.

Samarium(III) complex $1_N$

The hydrochloride salt of macrocycle $1_H$ (300 mg, 0.407 mmol), Sm(NO$_3$)$_3$·5H$_2$O (270 mg, 0.611 mmol), TBANO$_3$ (305 mg, 1.0 mmol) and triethylamine (ca. 0.5 mL) in 350 mL methanol were heated to reflux under air for 7 h. After workup using the general procedure outlined above, 183 mg of a dark green crystalline solid was obtained (46%). This material has the potential for X-ray diffraction. For $1_N$: UV/vis: [(MeOH) λ$_{max}$, nm (log ε)]: 354.5 (4.36), 415.5 (4.71), 475.5 (5.09), 682 (4.09), 741 (4.61); FAB MS, M$^+$: m/e m/e 849; HRMS, M$^+$: m/e 848.2957 (calcd. for C$_{40}$H$_{50}$N$_5$O$_6$$^{152}$Sm, 848.2959). Anal. calcd. for [C$_{40}$H$_{50}$N$_5$O$_6$Sm](NO$_3$)$_2$(CH$_3$OH): C, 48.99; H, 5.42; N, 9.76. Found: C, 48.79; H, 5.64; N, 9.43.

Europium(III) complex $1_O$

The hydrochloride salt of macrocycle $1_H$ (400 mg, 0.543 mmol), Eu(NO$_3$)$_3$·5H$_2$O (290 mg, 0.65 mmol), TBANO$_3$ (500 mg, 1.64 mmol) and triethylamine (ca 1 mL) in 350 mL methanol were heated to reflux under air for 16 h. After workup using the general procedure outlined above, 255 mg of a dark green crystalline solid was obtained (48%). This material was suitable for X-ray diffraction analysis. For $1_O$: UV/vis: [(MeOH) λ$_{max}$, nm (log ε)]: 414 (4.72), 475.5 (5.10), 678 (4.08), 739.5 (4.63); FAB MS, (M+H)$^+$: m/e 850; HRMS, M$^+$: m/e 849.2961 (calcd. for C$_{40}$H$_{50}$N$_5$O$_6$$^{153}$Eu, 849.2974). Anal. calcd. for [C$_{40}$H$_{50}$N$_5$O$_6$Eu] (NO$_3$)$_2$(H$_2$O): C, 47.56; H, 5.39; N, 9.71. Found: C, 47.47; H, 5.45; N, 9.64.

Gadolinium (III) complex $1_P$

The hydrochloride salt of macrocycle $1_H$ (750 mg, 1 mmol), Gd(NO$_3$)$_3$·5H$_2$O (660 mg, 1.5 mmol), TBANO$_3$ (930 mg 3.0 mmol) and triethylamine (ca. 1 mL) in 600 mL methanol were heated to reflux under air for 12 h. After workup using the procedure outlined above, the dark green complex was recrystallized from chloroform/methanol/diethylether to yield 700 mg (72%) of a deep green crystalline solid. X-ray quality single crystals were obtained by dissolving the complex in methanol/chloroform and carefully layering the dark green solution with a small amount of methanol, then with diethylether. The layered solution was kept at room temperature in the dark for a few days. For $1_P$: UV/vis: [(MeOH) λ$_{max}$, nm (log ε)]: 358 (4.33), 416 (4.72), 478 (5.12), 678 (4.03), 737.5 (4.64); [(H$_2$O) λ$_{max}$, nm (log ε)]: 347 (4.43), 419 (4.75), 469 (5.08), 740 (4.60). IR (KBr, cm$^{-1}$, major peaks): υ3299 (OH), 1647 (C=N), 1601 (C=N), 1507, 1456, 1437, 1385 (NO$_3$—), 1290, 1221, 1098, 1082. FAB MS, M$^+$: m/e 854; HRMS, M$^+$: m/e 854.2989 (calcd. for C$_{40}$H$_{50}$N$_5$O$_6$$^{158}$Gd, 854.300. Anal. calcd. for [C$_{40}$H$_{50}$N$_5$O$_6$Gd] (NO$_3$)$_2$(CH$_3$OH) (H$_2$O): C, 47.85; H, 5.49; N, 9.53. Found: C, 47.62; H, 5.37; N, 9.54. NOTE: If the alumina is not pre-treated with a NaNO$_3$ wash, the Gd(III) will not have two nitrate counter anions, instead it will have one nitrate and one chloride counter anion: Anal. calcd. for [C$_{40}$H$_{50}$N$_5$O$_6$Gd] (NO$_3$)Cl(H$_2$O)$_2$: C, 48.65; H, 5.51; N, 8.51; Cl, 3.59. Found: C, 48.21; H, 5.58; N, 8.34; Cl, 3.62.

Terbium(III) complex $1_Q$

The hydrochloride salt of macrocycle $1_H$ (300 mg, 0.407 mmol), Tb(NO$_3$)$_3$·6H$_2$O (276 mg, 0.611 mmol), TBANO$_3$ (305 mg, 1.64 mmol) and triethylamine (ca. 0.5 mL) in 350 mL methanol were heated to reflux under air for 12 h. After workup using the general procedure outlined above, 152 mg of the complex was obtained (38%). For $1_Q$: UV/vis: [(MeOH) λ$_{max}$, nm (log ε)]: 353 (4.35), 414 (4.71), 474.5 (5.09), 680 (4.08), 737 (4.62); FAB MS, M$^+$: m/e 856; HRMS, M$^+$: m/e 855.3017 (calcd. for C$_{40}$H$_{50}$N$_5$O$_6$$^{159}$Tb, 855.3015). Anal. calcd. for [C$_{40}$H$_{50}$N$_5$O$_6$Tb] (NO$_3$)$_2$(CH$_3$OH) (H$_2$O): C, 47.80; H, 5.48; N, 9.52. Found: C, 48.11; H, 5.28; N, 9.75.

Dysprosium(III) complex $1_R$

The hydrochloride salt of macrocycle $1_H$ (300 mg, 0.407 mmol), Dy(NO$_3$)$_3$·5H$_2$O (266 mg, 0.611 mmol), TBANO$_3$ (305 mg, 1.64 mmol) and triethylamine (ca. 0.5 mL) in 350 mL methanol were heated to reflux under air for 5 h. After workup using the general procedure outlined above, 250 mg of the complex was obtained (62%). For $1_R$: UV/vis: [(MeOH) λ$_{max}$, nm (log ε)]: 354 (4.32), 414 (4.68), 475 (5.07), 677.5 (4.03), 735.5 (4.60); FAB MS, (M+H)$^+$: m/e 861; HRMS, M$^+$: m/e 860.3048 (calcd. for C$_{40}$H$_{50}$N$_5$O$_6$$^{164}$Dy, 860.3053). Anal. calcd. for [C$_{40}$H$_{50}$N$_5$O$_6$Dy] (NO$_3$)$_2$(H$_2$O): C, 47.89; H, 5.23; N, 9.78. Found: C, 47.97; H, 5.22; N, 9.72.

Holmium(III) complex $1_S$

The hydrochloride salt of macrocycle $1_H$ (300 mg, 0.407 mmol), Ho(NO$_3$)$_3$·6H$_2$O (269 mg, 0.611 mmol), TBANO$_3$ (305 mg, 1.64 mmol) and triethylamine (ca. 0.5 mL) in 350 mL methanol were heated to reflux under air for 12 h. After workup using the general procedure outlined above, 220 mg of the complex was obtained (55%). For $1_S$: UV/vis: [(MeOH) $\lambda_{max}$, nm (log $\epsilon$)]: 354 (4.35), 414 (4.72), 475.5 (5.12), 677 (4.08), 734 (4.65); FAB MS, M$^+$: m/e 862; HRMS, M$^+$: m/e 861.3044 (calcd. for $C_{40}H_{50}N_5O_6{}^{165}Ho$, 861.3064). Anal. calcd. for [$C_{40}H_{50}N_5O_6Ho$] $(NO_3)_2(CH_3OH)$ $(H_2O)$: C, 47.52; H, 5.45; N. 9.47. Found: C, 47.55; H, 5.26; N, 9.30.

Erbium(III) complex $1_T$

The hydrochloride salt of macrocycle $1_H$ (300 mg, 0.407 mmol), $Er(NO_3)_3.5H_2O$ (270 mg, 0.611 mmol), $TBANO_3$ (305 mg, 1.64 mmol) and triethylamine (ca. 0.5 mL) in 350 mL methanol were heated to reflux under air for 12 h. After workup using the general procedure outlined above, 143 mg of the complex was obtained (36%). For $1_T$: UV/vis: [(MeOH) $\lambda_{max}$, nm (log $\epsilon$)]: 355.5 (4.36), 414.5 (4.72), 477 (5.13), 672 (4.08), 732 (4.66); FAB MS, M$^+$: m/e 863; HRMS, M$^+$: m/e 865.3110 (calcd. for $C_{40}H_{50}N_5O_6{}^{166}Er$, 862.3064). Anal. calcd. for [$C_{40}H_{50}N_5O_6Er$] $(NO_3)_2(CH_3OH)$: C, 48.32; H, 5.34; N, 9.63. Found: C, 48.14; H, 5.14; N, 9.55.

Thulium(III) complex $1_U$

The hydrochloride salt of macrocycle $1_H$ (300 mg, 0,407 mmol), $Tm(NO_3)_3.5H_2O$ (274 mg, 0,611 mmol), $TBANO_3$ (305 mg, 1.64 mmol) and triethylamine (ca. 0.5 mL) in 350 mL methanol were heated to reflux under air for 22 h. After workup using the general procedure outlined above, 150 mg of the complex was obtained (37%). This complex is more difficult to purify due to its lower solubility in methanol/chloroform solutions, which leads to its lower yield. For $1_U$: UV/vis: [(MeOH) $\lambda_{max}$, nm (log $\epsilon$)]: 355.5 (4.36), 414.5 (4.72), 477 (5.13), 672 (4.08), 732 (4.66); FAB MS, M$^+$: m/e 866; HRMS, M$^+$: m/e 865.3110 (calcd. for $C_{40}H_{50}N_5O_6{}^{169}Tm$, 865.3103). Anal. calcd. for [$C_{40}H_{50}N_5O_6Tm$] $(NO_3)_2(H_2O)_2$: C, 46.82; H, 5.31; N, 9.56. Found: C, 46.85; H, 5.23; N, 9.38.

Ytterbium(III) complex $1_V$

The hydrochloride salt of macrocycle $1_H$ (300 mg, 0.407 mmol), $Yb(NO_3)_3.5H_2O$ (274 mg, 0,611 mmol), $TBANO_3$ (305 mg, 1.64 mmol) and triethylamine (ca. 0.5 mL) in 350 mL methanol were heated to reflux under air for 24 h. After workup using the general procedure outlined above, 220 mg of the complex was obtained (54%). For $1_V$: FAB MS, M$^+$: m/e 870; HRMS, M$^+$: m/e 870. 3132 (calcd. for $C_{40}H_{50}N_5O_6{}^{174}Yb$, 870.3149).

Lutetium(III) complex $1_W$

The hydrochloride salt of macrocycle $1_H$ (300 mg, 0.407 mmol), $Lu(NO_3)_3.H_2O$ (220 mg, 0.611 mmol), $TBANO_3$ (305 mg, 1.64 mmol) and triethylamine (ca. 0.5 mL) in 350 mL methanol were heated to reflux under air for 24 h. After workup using the general procedure outlined above, 150 mg of the complex was obtained (37%). This complex has very low solubility in methanol/chloroform solution. Almost half of the product remained on the column during purification. For $1_W$: FAB MS, M$^+$: m/e 872; HRMS, M$^+$: m/e 871.3154 (calcd. for $C_{40}H_{50}N_5O_6{}^{175}Lu$, 871.3169).

Acid-catalyzed Schiff-base condensation between $1_G$ and $1_F$ produced the so-called "sp$^3$" nonaromatic macrocycle $1_H$ in quantitative yield. Macrocycle $1_H$ is quite stable, decomposing only slightly over a period of months when stored in freezer. Oxidation and metallation of $1_H$ in the presence of 1.5 equivalents of lanthanide(III) metal salt, triethylamine, and air in boiling methanol produces a deep green metal complex within 3–24 hours (as judged by UV-Vis) of reaction time. All the lanthanide(III) [La-Lu, except Pm] texaphyrin complexes $1_J$–$1_W$ were isolated with unoptimized yields ranging from 34%–75%. Satisfactory spectroscopic and mass spectrometric data were obtained for all new compounds. Single crystals suitable for X-ray diffraction analysis of the Eu(III) and Gd(III) complexes $1_O$ and $1_P$, respectively, were obtained by dissolving each complex in MeOH/CHCl$_3$ and layering with diethyl ether.

EXAMPLE 2

Synthesis of Europium(III) T2B1 TXP-oligo Conjugate

Figure 2A:
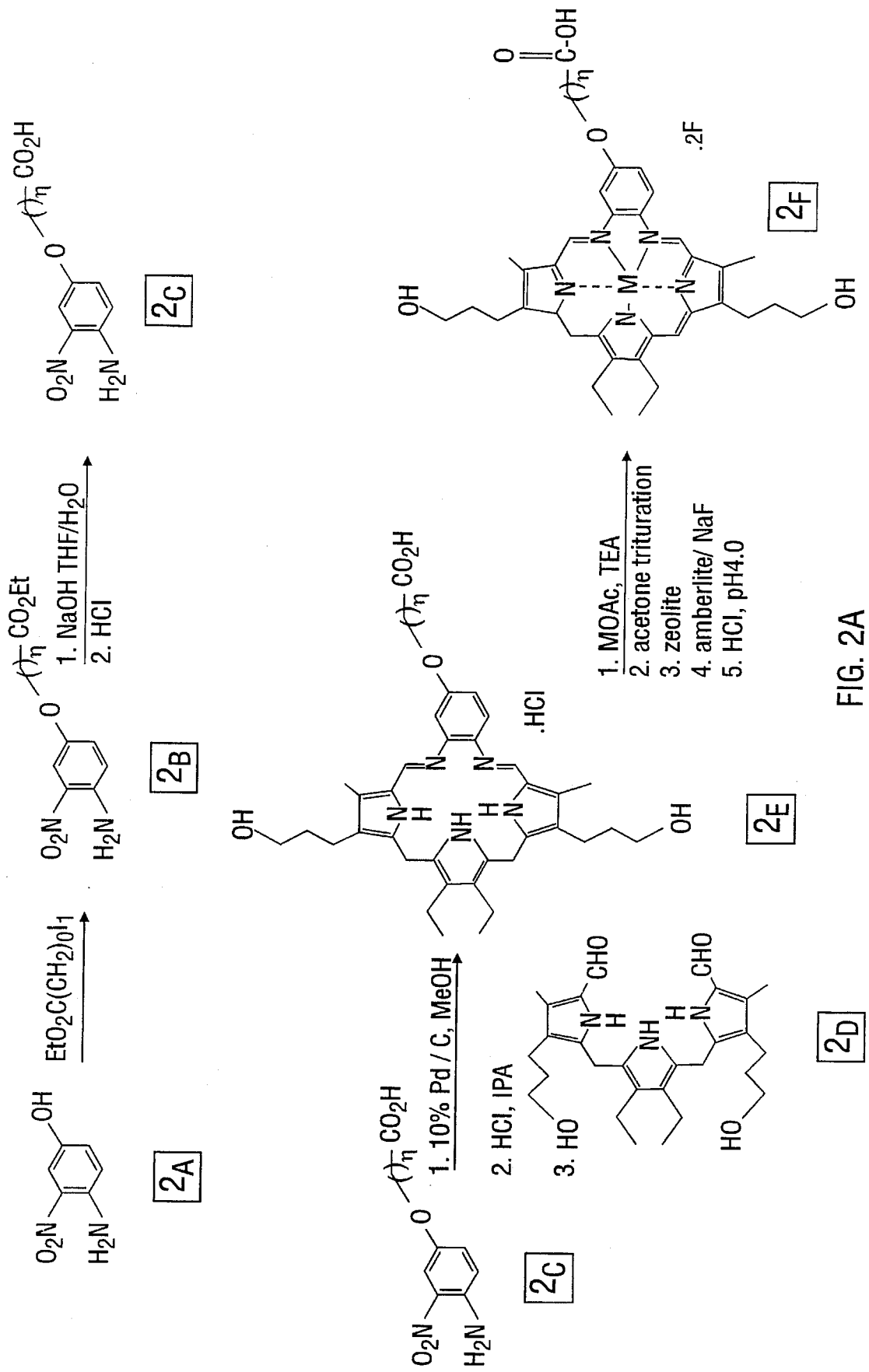
FIG. 2A and FIG. 2B schematically summarize the synthesis of an oligonucleotide conjugate of a texaphyrin metal complex, $2_H$.
Figure 2B:
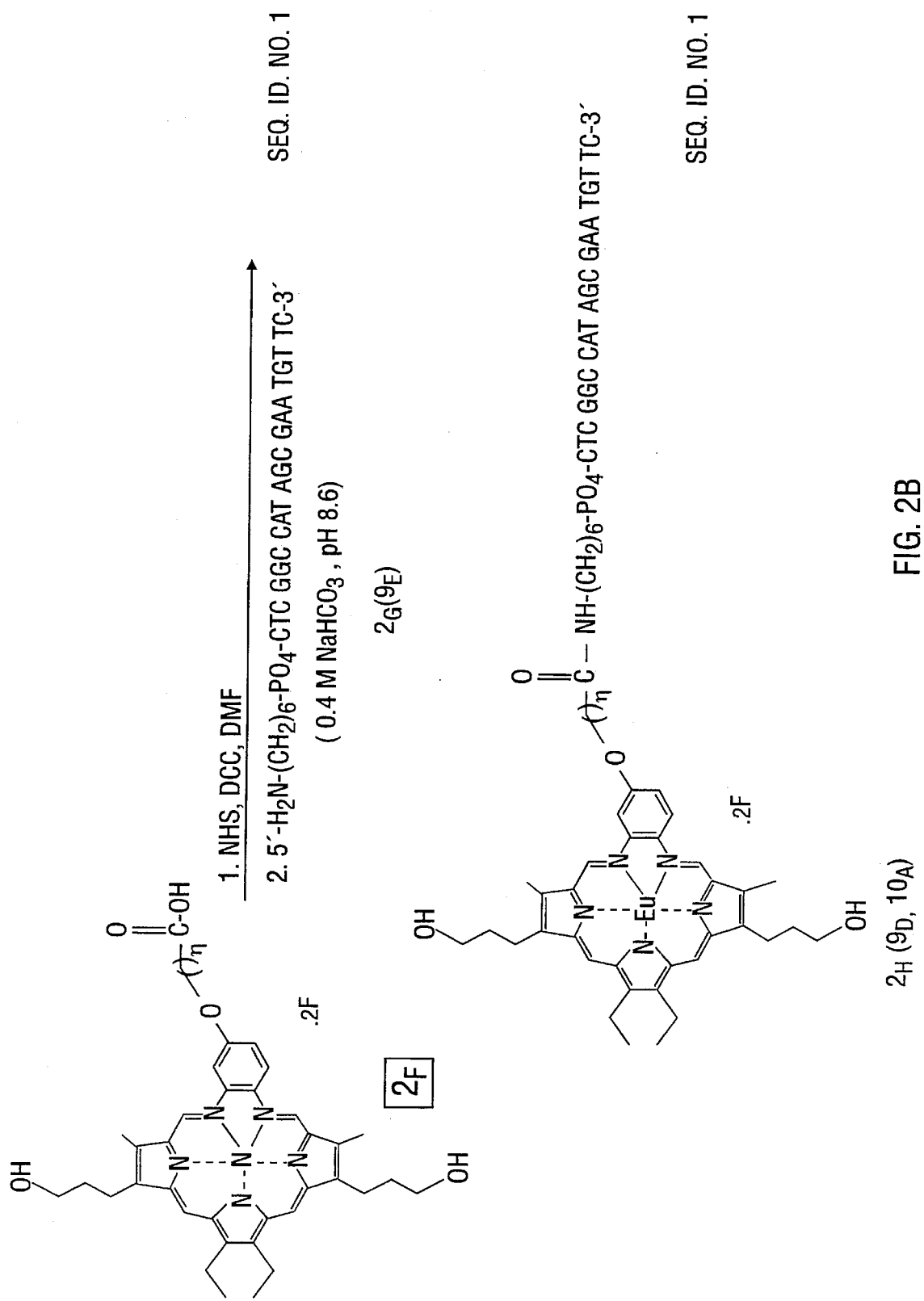

The present example provides for the synthesis of a texaphyrin metal complex-oligonucleotide conjugate useful for site-directed hydrolysis of ester bonds of a complementary nucleic acid (see FIG. 2A and FIG. 2B).

4-Amino-1-[1-(ethyloxy)acetyl-2-oxy]-3-nitrobenzene $2_B$, n=1

Potassium carbonate (14.0 g, 101 mmol) and 4-amino-3-nitrophenol $2_A$ (10.0 g, 64.9 mmol) were suspended in 150 mL dry acetonitrile. Ethyl-2-iodoacetate (10 mL, 84.5 mmol) (or ethyl iodobutyrate may be used, in that case n=3) was added via syringe, and the suspension was stirred at ambient temperature for ca. 21 h. Chloroform (ca. 375 mL) was added, and used to transfer the suspension to a separatory funnel, whereupon it was washed with water (2×ca. 100 mL). The water washes were in turn washed with CHCl$_3$ (ca. 100 mL) and the combined CHCl$_3$ extracts were washed with water (ca. 100 mL). Solvents were removed on a rotary evaporator, and the residue was redissolved in CHCl$_3$ (ca. 500 mL) and precipitated into hexanes (1.5 L). After standing two days, the precipitate was filtered using a coarse fritted funnel and dried in vacuo to provide 14.67 g compound $2_B$, n=1 (94.1%). TLC: Rf=0.43, CHCl$_3$.

4-Amino-1-[1-(hydroxy)acetyl-2-oxy]-3-nitrobenzene $2_C$, n=1

4-Amino-1-[1-(ethyloxy) acetyl-2-oxy]-3-nitrobenzene $2_B$, n=1, (10.00 g, 37.3 mmol) was dissolved in tetrahydrofuran (100 mL), aqueous sodium hydroxide (1M solution, 50 mL) was added and the solution was stirred at ambient temperature for ca. 21 h. Tetrahydrofuran was removed on a rotary evaporator, and water (100 mL) was added. The solution was washed with CHCl$_3$ (ca. 200 mL), then neutralized by addition of hydrochloric acid (1M solution, 50 mL). The precipitate which formed was filtered after standing a few minutes, washed with water, and dried in vacuo to provide 8.913 g compound $2_C$, n=1 (99.5%). TLC: Rf=0.65, 10% methanol/CHCl$_3$.

16-[1-(Hydroxy) acetyl-2-oxy]-9,24-bis(3-hydroxypropyl)-4,5-diethyl-10,23-dimethyl-13,20,25,26,27-pentaazapentacyclo[20.2.1.1$^{3,6}$.1$^{8,11}$.0$^{14,19}$] heptacosa-3,5,8,10,12,14(19), 15,17,20,22,24-undecaene $2_E$, n=1.

4-Amino-1-[1-(hydroxy) acetyl- 2-oxy]-3-nitrobenzene $2_C$, n=1 (1.800 g, 8.49 mmol) was dissolved in methanol (100 mL) in a 1 L flask. Palladium on carbon (10%, 180 mg) was added, and the atmosphere inside the flask was replaced with hydrogen at ambient pressure. A grey precipitate was formed after ca. 3 h, and the supernatant was clear. Methanol was removed in vacuo, taking precautions to prevent exposure to oxygen, and the compound was dried overnight in vacuo. Isopropyl alcohol (500 mL) and HCl (12M, 400 μL) were added, and the suspension was allowed to stir for ca. 15'. 2,5-Bis[(3-hydroxypropyl-5-formyl-4-methylpyrrol-2-yl)methyl]-3,4-diethylpyrrole $2_D$ (n=1) (4.084 g, 8.49 mmol) was added, and the reaction stirred at room temperature under argon for 3 hours. Hydrochloric acid was again added (12M, 400 μL) and the reaction again was allowed to stir for an additional 3.5 h. The resulting red solution was filtered through celite, and the filtercake was washed with isopropyl alcohol until the filtrate was colorless. Solvent was reduced to a volume of ca. 50 mL using a rotary evaporator, whereupon the solution was precipitated into rapidly stirring Et$_2$O (ca. 700 mL). Compound $2_E$ (n=1) was obtained as a red solid (5.550 g, 98.4%) upon filtering and drying in vacuo. TLC: R$_f$=0.69, 20% methanol/CHCl$_3$ (streaks, turns green on plate with I$_2$).

Europium (III) complex of 16-[1-(hydroxy) acetyl-2-oxy]-9,24-bis( 3-hydroxypropyl)-4,5-diethyl-10,23-dimethyl-13, 20,25,26,27-pentaazapentacyclo [20.2.1.1$^{3,6}$.1$^{8,11}$.0$^{14,19}$] heptacosa- 1,3,5,7,9,11(27),12,14(19),15,17,20,22(25),23-tridecaene $2_F$, n=1.

The protonated form of the macrocycle, 16-[1-(hydroxy) acetyl- 2-oxy]-9,24-bis(3-hydroxypropyl)-4,5-diethyl-10,23-dimethyl-13,20,25,26,27-pentaazapentacyclo [20.2.1.1$^{3,6}$ .1$^{8,11}$.0$^{14,19}$] heptacosa-3,5,8,10,12,14(19),15, 17,20,22,24-undecaene hydrochloride $2_E$, n=1 (500 mg, 753 μmol), europium(III) acetate pentahydrate (334 mg, 797 μmol) and triethylamine (1.33 mL, 8.0 mmol) in 150 mL of methanol were heated to reflux under air for 5.5 h. The reaction was cooled to room temperature, and stored at −20° C. overnight. Solvent was removed on a rotary evaporator, acetone (200 mL) was added, and the suspension was stirred on a rotary evaporator for 2 h. The suspension was filtered and the precipitate was dried briefly in vacuo, whereupon a solution was formed in methanol (ca. 250 mL) and water (25 mL). The pH was adjusted to 4.0 using HCl (1M), HCl-washed zeolite LZY54 was added (ca. 5 g) and the suspension was stirred on the rotary evaporator for ca. 6 h. Amberlite™ IRA-900 ion exchange resin (NaF treated, ca. 5 g) was added, and the suspension was stirred for an additional hour. The suspension was filtered, the resin was washed with methanol (ca. 100 mL), and the filtrate was adjusted to pH 4.0 using HCl (1M). Solvents were removed on a rotary evaporator, using ethanol (abs.) to remove traces of water. After drying in vacuo, the compound was dissolved in methanol (25 mL) and precipitated into rapidly stirring Et$_2$O (300 mL). Compound $2_F$, n=1 was obtained as a olive precipitate (303 mg, 48.4%) after filtering and drying in vacuo. An analytical sample was prepared by treating 50 mg of $2_F$, n=1 dissolved in methanol (25 mL) with acetic acid-washed zeolite, then acetic acid-washed Amberlite™ for ca. 1 h. After reducing methanol to a minimum volume, the solution was precipitated into rapidly stirring Et$_2$O (70 mL), filtered, and dried in vacuo. Analysis. Calculated for (C$_{36}$H$_{39}$N$_5$O$_5$Eu) (CH$_3$CO$_2$) (H$_2$O): C, 53.66; H, 5.21, N, 8.23. Found: C, 53.39, H, 5.50, N, 8.25. HR FAB mass spectrum, M$^+$: Calculated for C$_{36}$H$_{40}$N$_5$O$_5$Eu, 773.2228. Found: 773.2239. UV/vis (MeOH) [λ$_{max}$, nm (log ε)]: 330.0 (4.47), 464.0 (4.72), 708.0 (3.90), 762.0 (4.35).

Postsynthetic modification of oligodeoxynucleotide-amine $2_G$ ($9_E$) with europium(III) complex $2_F$, n=1

The europium(III) complex of 16-[1-(hydroxy)acetyl-2-oxy]-9,24-bis(3-hydroxypropyl)- 4,5-diethyl-10,23-dimethyl-13,20,25,26,27-pentaazapentacyclo [20.2.1.1$^{3,6}$.1$^{8,11}$.0$^{14,19}$]heptacosa- 1,3,5,7,9,11(27),12,14(19),15,17,20, 22(25),23-tridecaene $2_F$, n=1, (25 mg, 30.1 μmol) and N-hydroxysuccinimide (5 mg, 43 μmol) were dried together overnight in vacuo. The compounds were dissolved in dimethylformamide (anhydrous, 500 μL) and dicyclohexylcarbodiimide (10 mg, 48 μmol) was added. The resulting solution was stirred under argon with protection from light for 8 h, whereupon a 110 μL aliquot was added to a solution of oligodeoxynucleotide $2_G$ (87 nmol) in a volume of 350 μL of 0.4M sodium bicarbonate buffer in a 1.6 mL eppendorf tube. After vortexing briefly, the solution was allowed to stand for 23 h with light protection. The suspension which formed was filtered through 0.45 μm nylon microfilterfuge tubes, and the eppendorf tube was washed with 250 μL sterile water. The combined filtrates were divided into two eppendorf tubes, and glycogen (20 mg/mL, 2 μL) and sodium acetate (3M, pH 5.4, 30 μL) were added to each tube. After vortexing, ethanol (absolute, 1 mL) was added to each tube to precipitate the DNA. Ethanol was decanted following centrifugation, and the DNA was washed with an additional 1 mL aliquot of ethanol and allowed to air dry. The pellet was dissolved in 50% formamide gel loading buffer (20 μL), denatured at 90° C. for ca. 2', and loaded on a 20% denaturing polyacrylamide gel. The yellow band corresponding to conjugate $2_H$, n=1 ($9_D$, $10_A$) was cut from the gel, crushed, and soaked in 1X TBE buffer (ca. 7 mL) for 1–2 days. The suspension was filtered through nylon filters (0.45 μm) and desalted using a Sep-pak™ reverse phase cartridge. The conjugate was eluted from the cartridge using 40% acetonitrile, lyophilized overnight, and dissolved in 1 mM HEPES buffer, pH 7.0 (500 μL). The solution concentration determined using UV/vis spectroscopy (calculated ε$^{260}$=187,110) was 21.6 μM in conjugate $2_H$, n=1 ($9_D$, $10_A$) (12%).

EXAMPLE 3

Figure 3A:
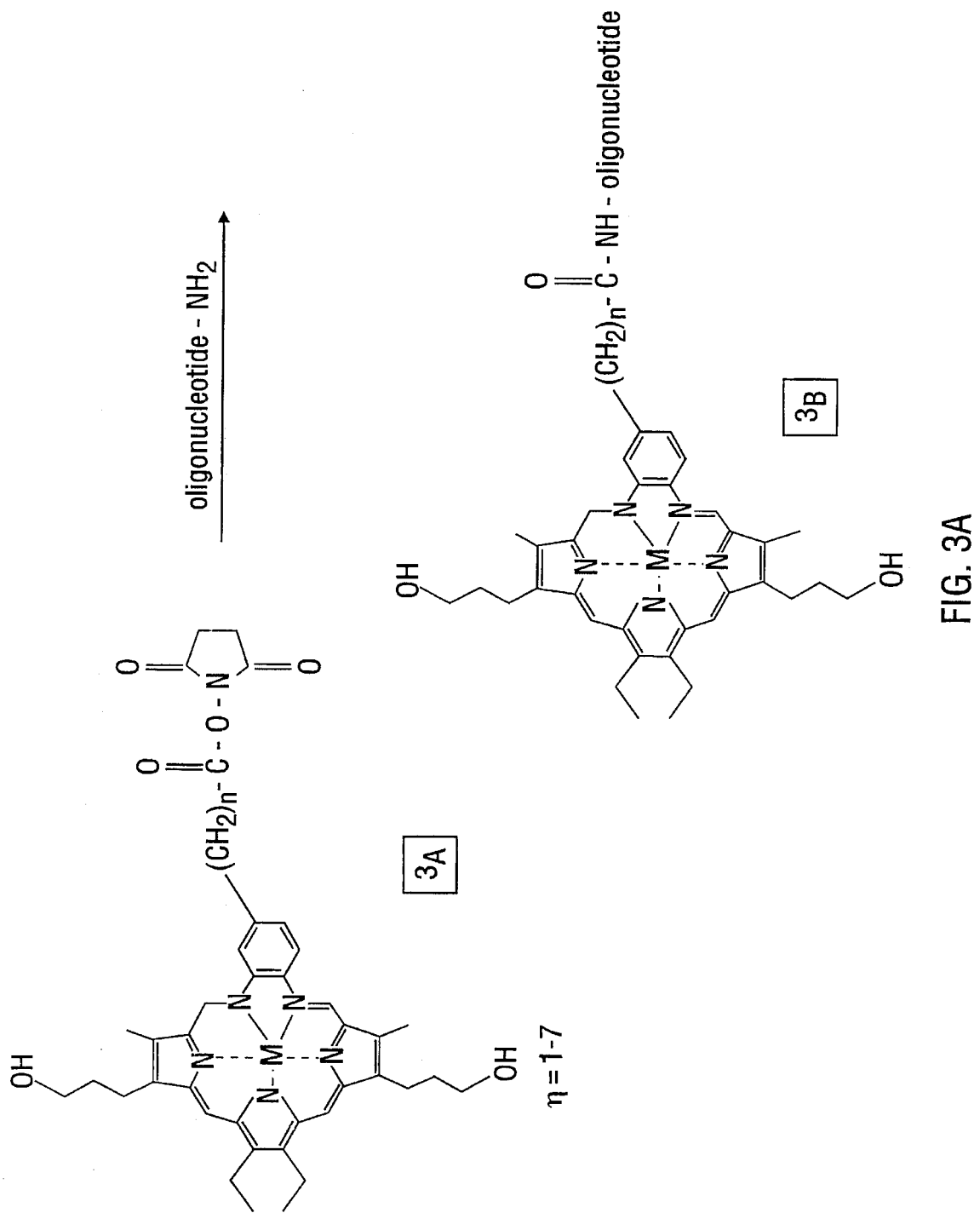
FIG. 3A, FIG. 3B and 3C demonstrate the covalent coupling of texaphyrin metal complexes with amine, thiol or hydroxy linked oligonucleotides to form preferred compounds of the present invention.
Figure 3B:
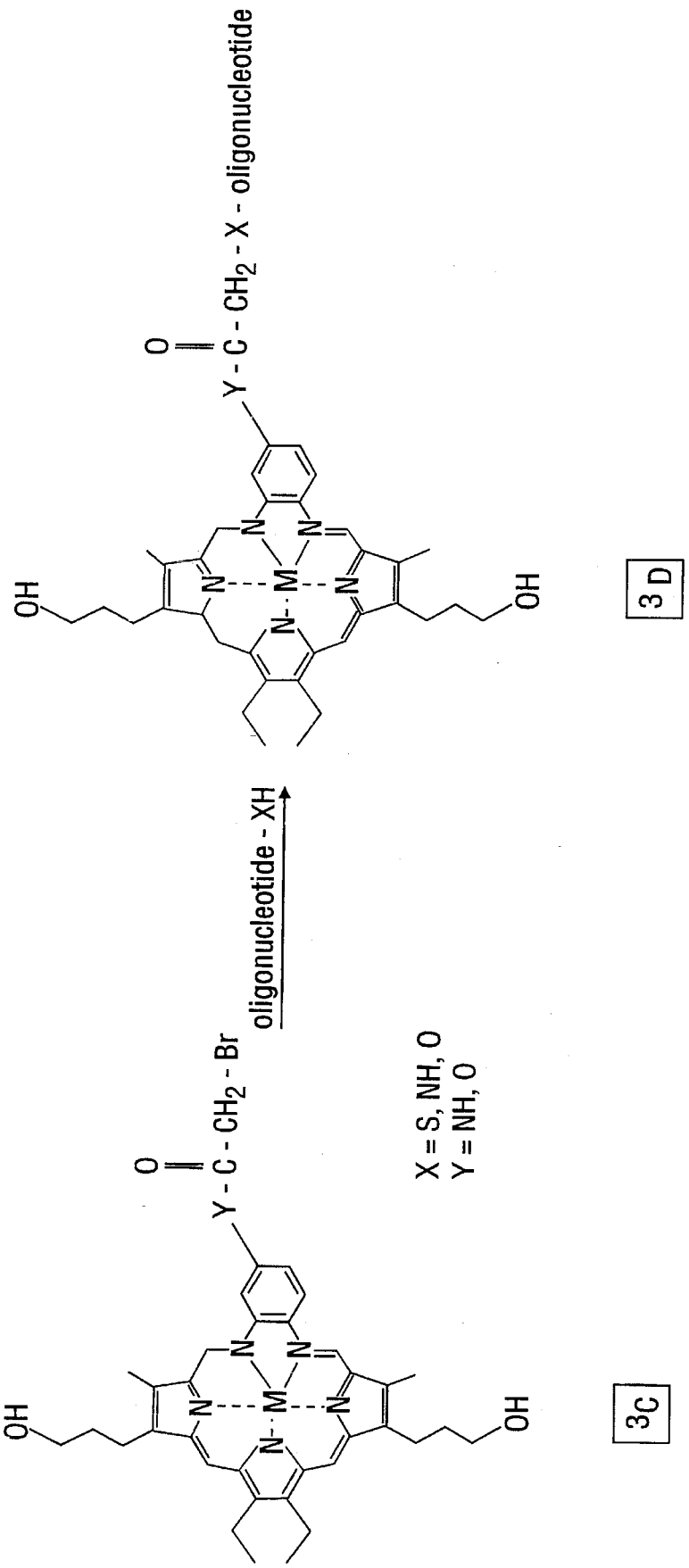
Figure 3C:
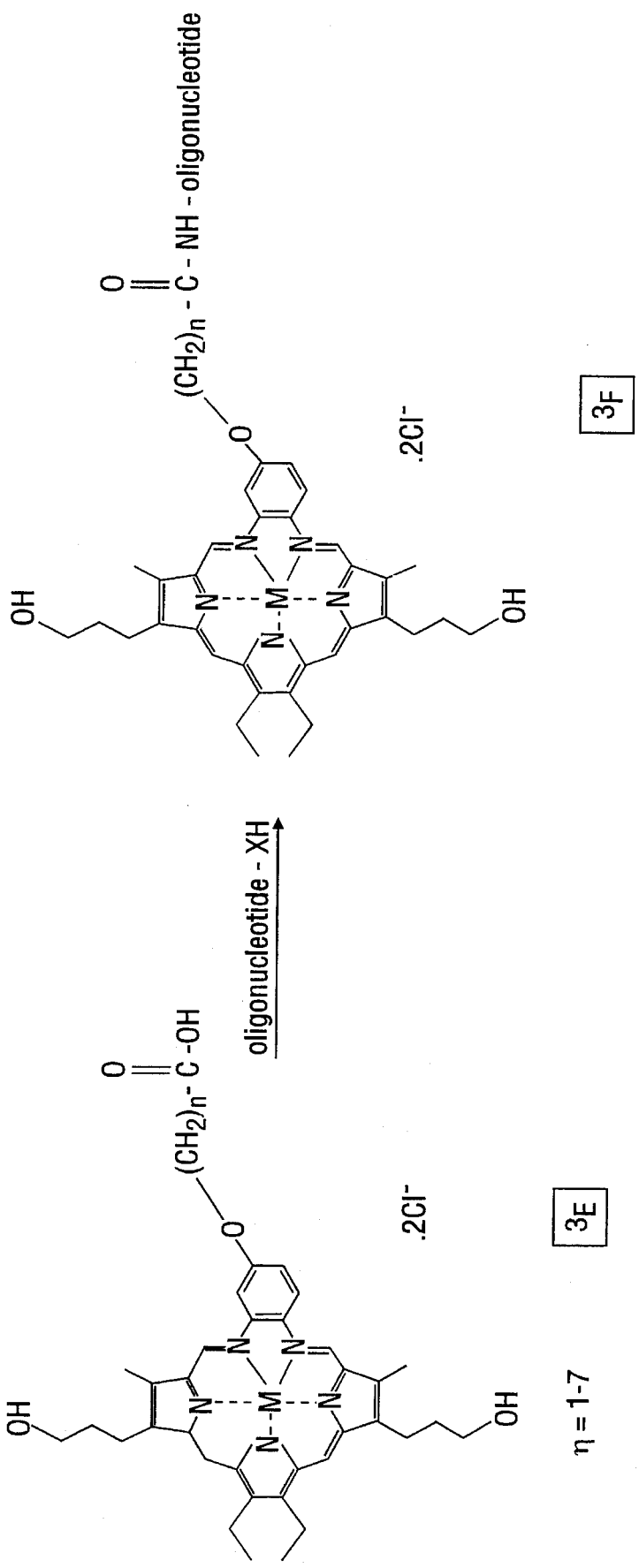
Figure 4A:
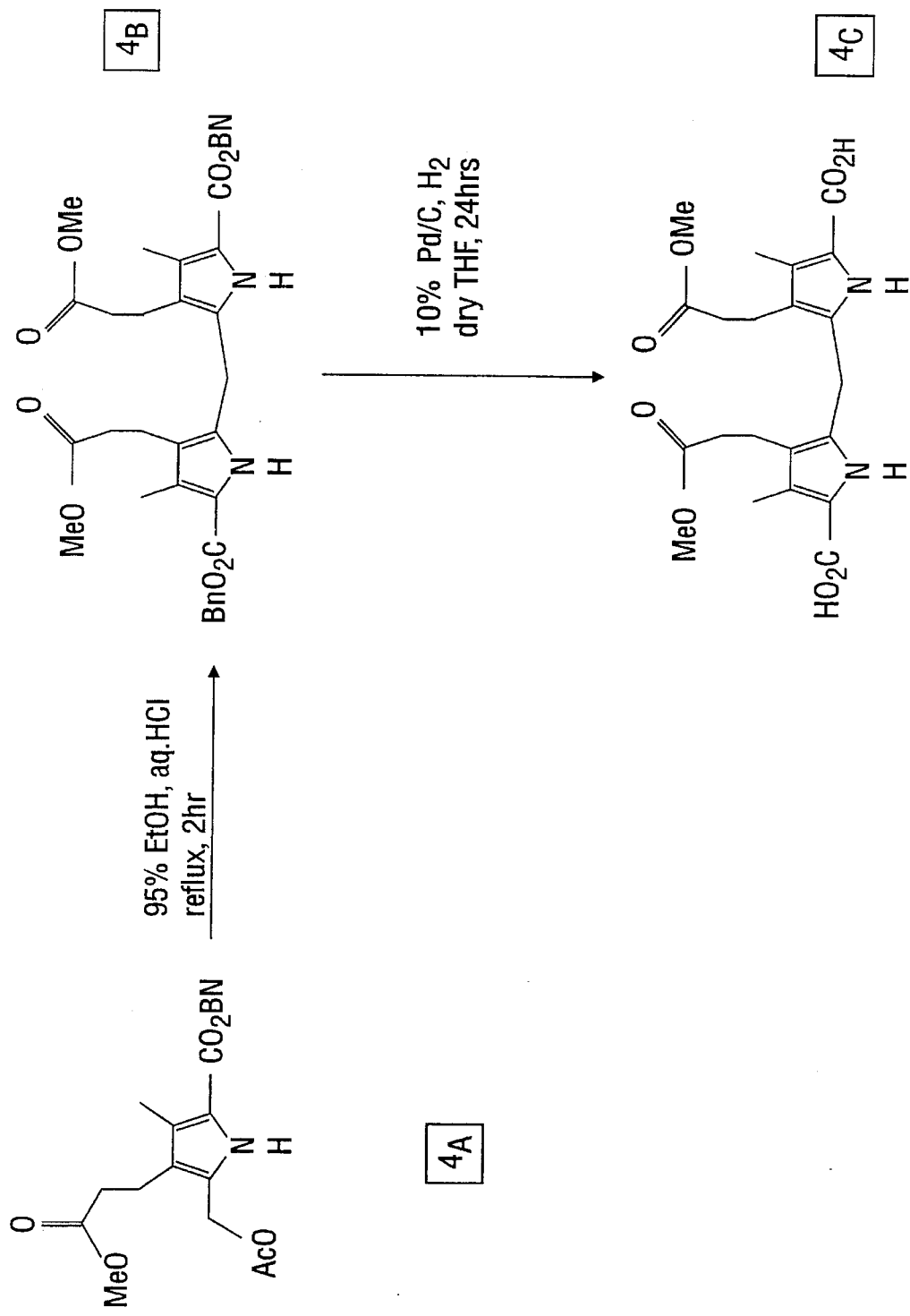
FIG. 4A, FIG. 4B, 4C, and 4D demonstrate the synthesis of diformyl monoacid tripyrrane $4_H$ and oligonucleotide conjugate $4_J$.
Figure 4B:
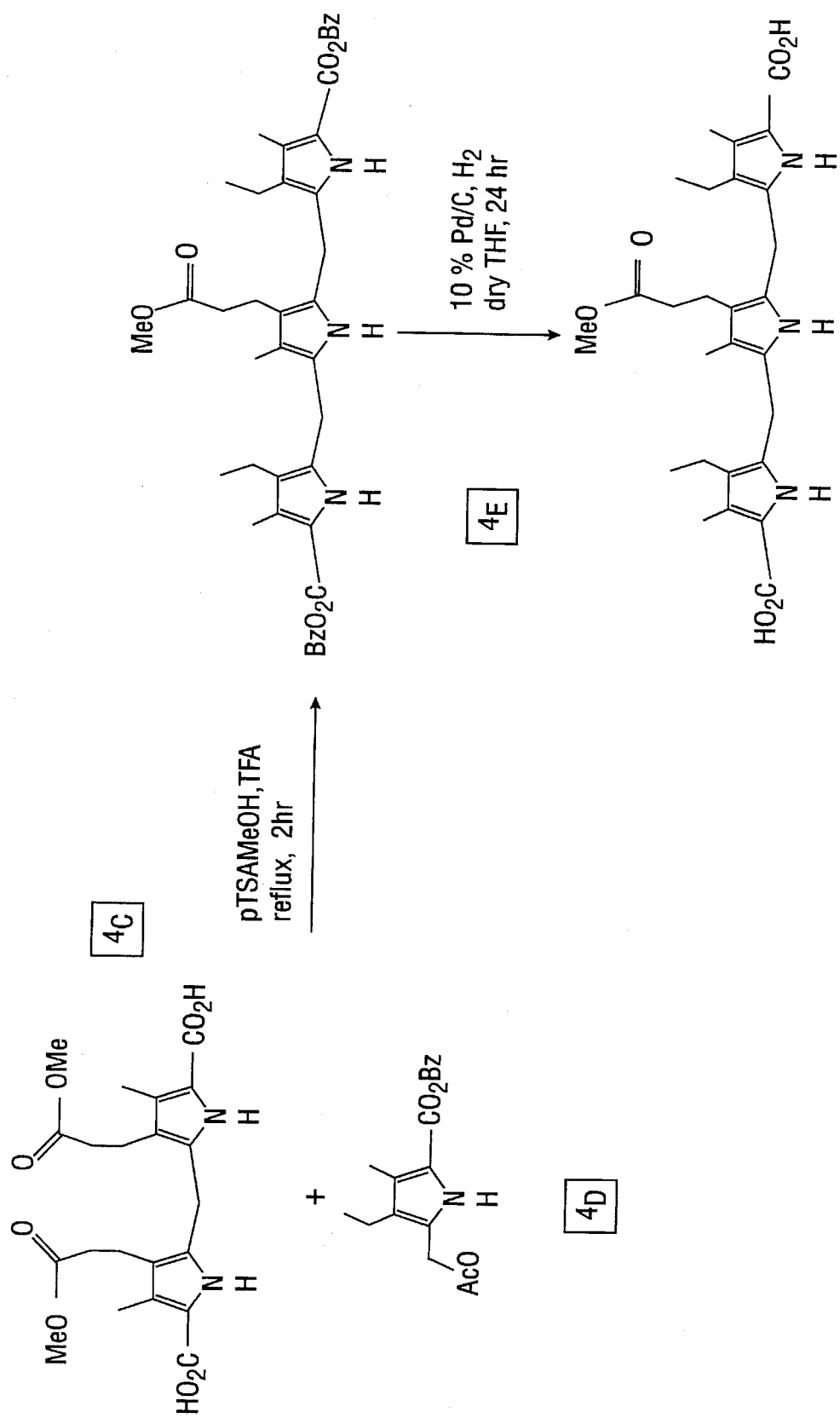
Figure 4C:
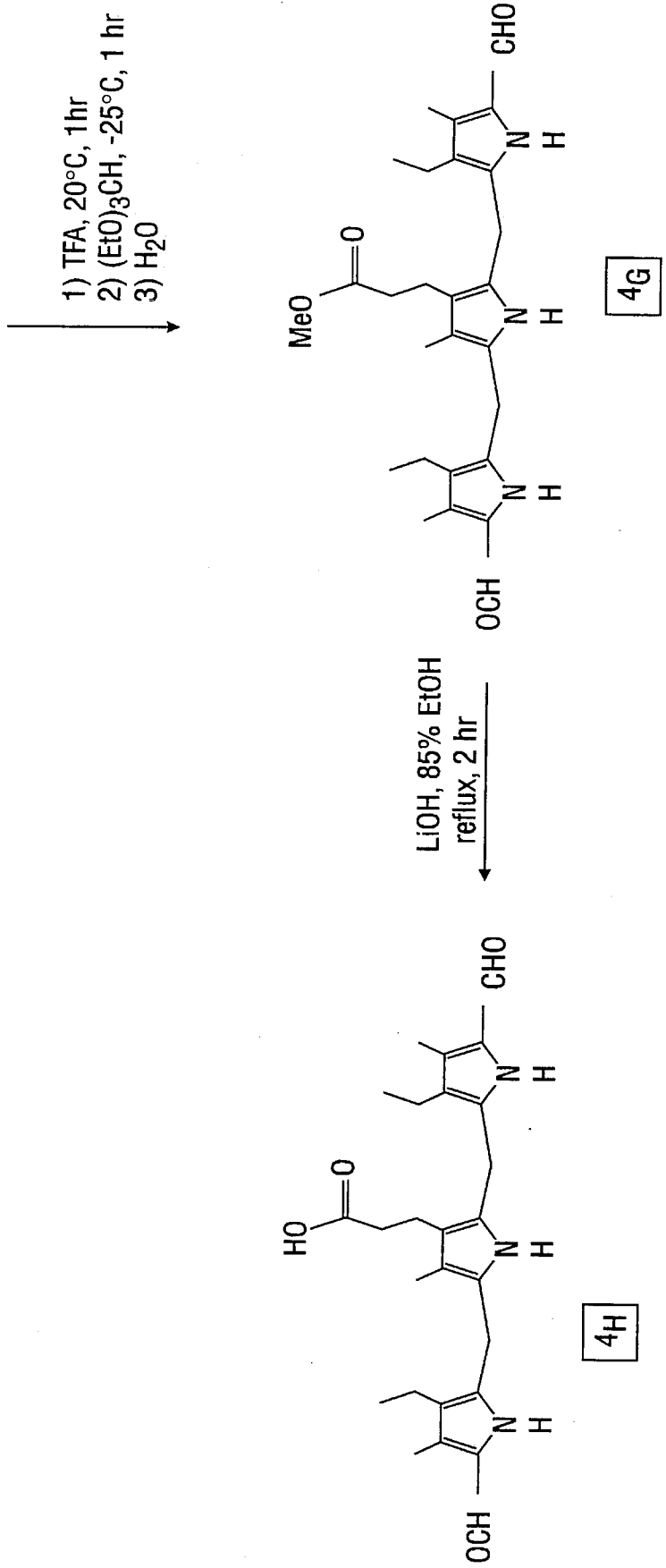
Figure 4D:
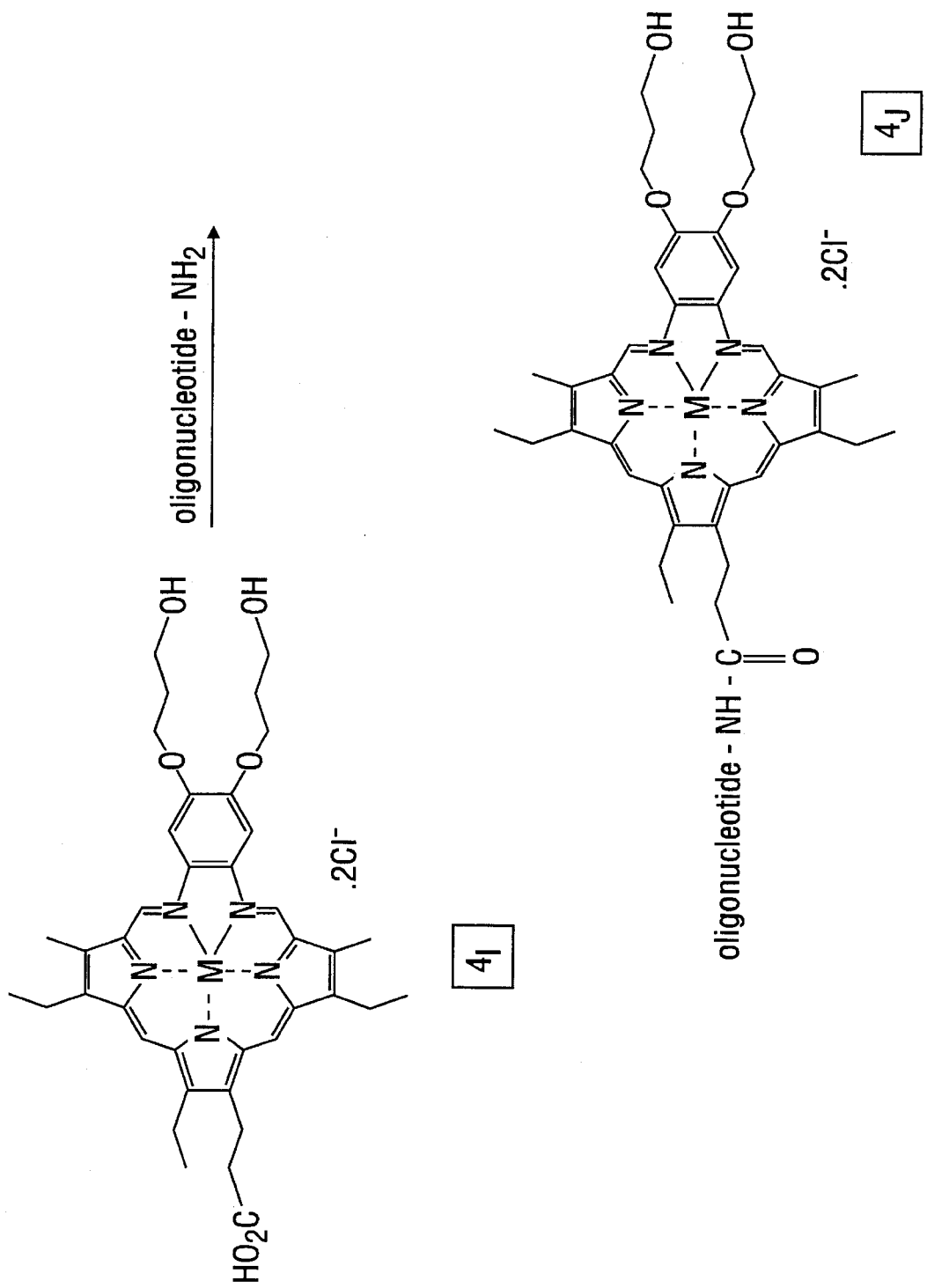
Figure 5:
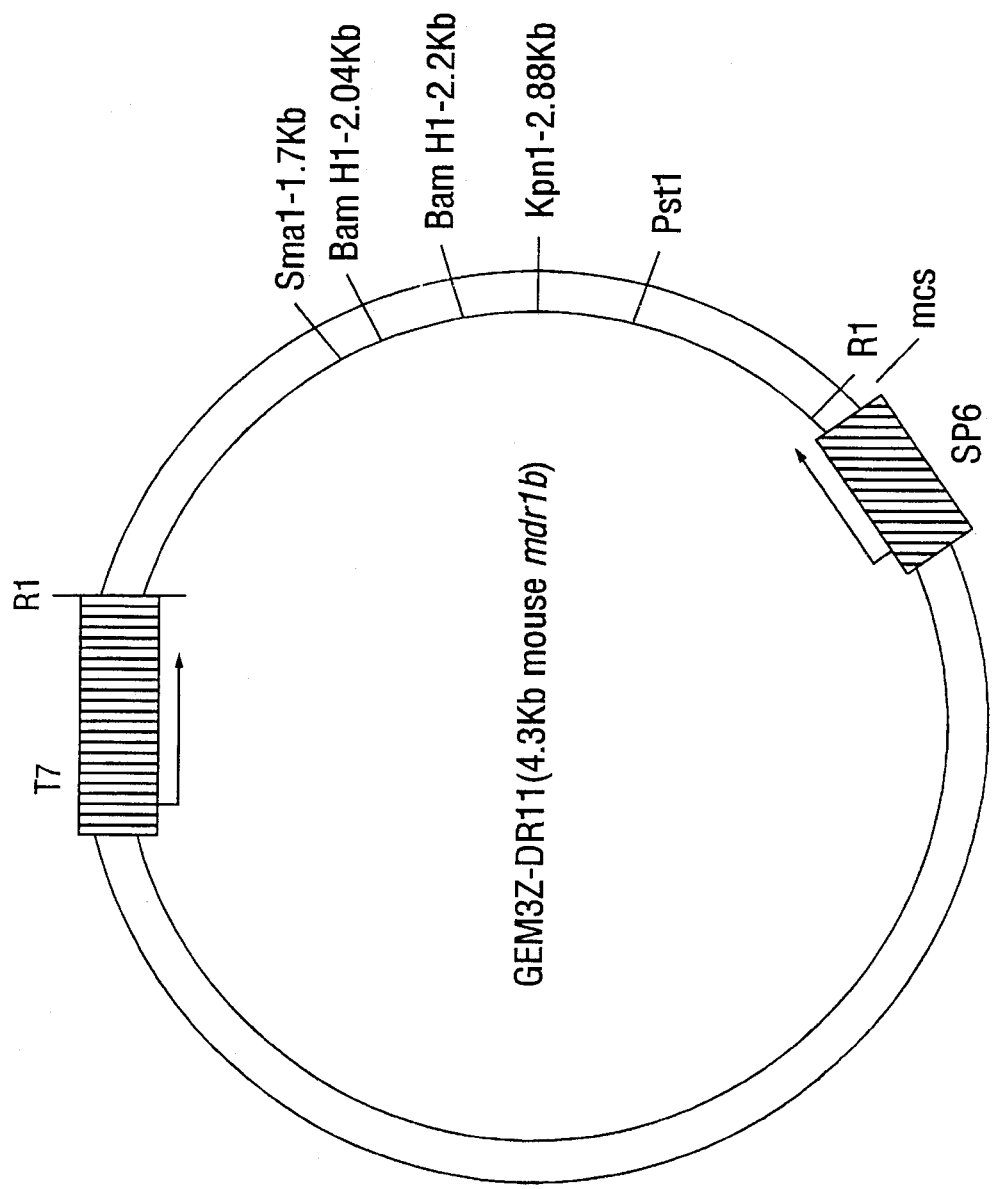
FIG. 5 shows the recombinant plasmid from which $^{32}P$-labelled 2000 base pair RNA transcripts were made for the RNA hydrolysis experiments of example 6. R1=EcoRI, MCS=multi-cloning sequence.

Synthesis of Texaphyrin Metal Complexes with Amine, Thiol or Hydroxy Linked Oligonucleotides, see FIG. 3A, FIG. 3B and 3C Amides, ethers and thioethers are representative of linkages which may be used for coupling site-directed molecules such as oligonucleotides to texaphyrin metal complexes (see FIG. 3A, FIG. 3B and FIG. 3C). Oligonucleotides or other site-directed molecules functionalized with amines at the 5'-end, the 3'-end, or internally at sugar or base residues are modified post-synthetically with an activated carboxylic ester derivative of the texaphyrin complex. Alternatively, oligonucleotide analogues containing one or more thiophosphate or thiol groups are selectively alkylated at the sulfur atom(s) with an alkyl halide derivative of the texaphyrin complex. Oligodeoxynucleotide-complex conjugates are designed so as to provide optimal catalytic interaction between the targeted RNA or DNA phosphoester backbone and the texaphyrin-bound lanthanide cation(s).

Oligonucleotides are used to bind selectively compounds which include the complementary nucleotide or oligo or polynucleotides containing substantially complementary sequences. As used herein, a substantially complementary sequence is one in which the nucleotides generally base pair with the complementary nucleotide and in which there are very few base pair mismatches.

Oligonucleotides are used, for example, as hybridization probes in blot analyses, primers for polymerase chain reaction (PCR) amplification, and for site-specific mutagenesis. Oligonucleotide-derived products are being used for the detection of genetic diseases and for proviral HIV, the causative agent of Acquired Immunodeficiency Syndrome (AIDS). They are also being considered as potential chemotherapeutic agents, for example, in gene therapy, and in an antisense capacity.

The oligonucleotide may be large enough to bind probably at least 9 nucleotides of complementary nucleic acid.

A general method for preparing oligonucleotides of various lengths and sequences is described by Caracciolo et al. (1989) *Science*, 245:1107.

In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to coupled is reacted with the free hydroxyl of a growing nucleotide chain derivatized to a solid support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base (*J. Org. Chem.*, 55:4693–4699, (1990) and Agrawal, (1990). Oligodeoxynucleotides or their phosphorothioate analogues may be synthesized using an Applied Biosystem 380B DNA synthesizer (Applied Biosystems, Inc., Foster City, Calif.).

EXAMPLE 4

Synthesis of diformyl monoacid tripyrrane $4_H$ and oligonucleotide conjugate $4_J$, see FIG. 4A, FIG. 4B, FIG. 4C, and FIG. 4D Dimethylester Dibenzylester Dipyrromethane $4_B$:

A three-neck 1000 ml round-bottom flask set with a magnetic stirring bar, a thermometer, a heating mantle, and a reflux condenser attached to an argon line was charged with methylester acetoxypyrrole $4_A$ (100.00 g; 267.8 mmol), 200 proof ethyl alcohol (580 ml), and deionized water (30 ml.) The reaction mixture was heated up and when the resulting solution began to reflux, 12N aq. hydrochloric acid (22 ml) was added all at once. The flask contents were stirred under reflux for two hours. The heating element was replaced by a 0° C. bath and the resulting thick mixture was stirred for two hours prior to placing it in the freezer overnight.

The mixture was filtered over medium fritted glass funnel, pressed with a rubber dam, and washed with hexanes until the filtrate came out colorless. The collected solids were set for overnight high vacuum drying at 30° C. to afford slightly yellowish solids (65.85 g, 214.3 mmol, 80.0% yield.)

Dimethylester Diacid Dipyrromethane, $4_C$:

All the glassware was oven dried. A three-neck 2000 ml round-bottom flask set with a magnetic stirring bar, a hydrogen line, and a vacuum line was charged with dimethylester dibenzylester dipyrromethane $4_B$ (33.07 g, 53.80 mmol), anhydrous tetrahydrofuran (1500 ml), and 10% palladium on charcoal (3.15 g.) The flask was filled with dry hydrogen gas after each of several purges of the flask atmosphere prior to stirring the reaction suspension under a hydrogen atmosphere for 24 hours.

The solvent of the reaction suspension was removed under reduced pressure. The resulting solids were dried under high vacuum overnight.

The dry solids were suspended in a mixture of saturated aqueous sodium bicarbonate (1500 ml) and ethyl alcohol (200 ml), and stirred at its boiling point for five minutes. The hot suspension was filtered over celite. The filtrate was cooled down to room temperature and acidified to pH 6 with 12N aqueous hydrochloric acid. The resulting mixture was filtered over medium fritted glass. The collected solids were dried under high vacuum to constant weight (21.63 g, 49.78 mmol, 92.5% yield.)

Methylester Dibenzylester Tripyrrane, $4_E$

A three-neck 2000 ml round-bottom flask set with a heating mantle, a magnetic stirring bar, a thermometer, and a reflux condenser attached to an argon line was charged with dimethylester diacid dipyrromethane $4_C$ (21.00 g, 48.33 mmol), ethyl acetoxy pyrrole $4_D$ (30.50 g), p-toluenesulfonic acid monohydrate (1.94 g), trifluoroacetic acid (39 ml), and methyl alcohol (1350 ml.) The flask contents were heated and stirred under reflux for two hours. The heating element was replaced with a 0° C. and the stirring was continued for half an hour prior to placing the resulting mixture in a freezer overnight.

The cold mixture was filtered over medium fritted glass. The collected solids were washed with hexanes and dried under high vacuum overnight (13.05 g, 19.25 mmol, 39.8% yield.)

Methylester Diacid Tripyrrane $4_F$:

All the glassware was oven dried. A three-neck 500 ml round-bottom flask set with a magnetic stirring bar, a hydrogen line, and a vacuum line was charged with methylester dibenzylester tripyrrane $4_E$ (12.97 g, 19.13 mmol), anhydrous tetrahydrofuran (365 ml), and 10% palladium on charcoal (1.13 g.) The flask was filled with dry hydrogen gas after each of several purges of the flask atmosphere prior to stirring the reaction suspension for 24 hours under a hydrogen atmosphere at room temperature.

The reaction suspension was filtered over celite. The solvent of the filtrate was removed under reduced pressure to obtain a foam which was dried under high vacuum overnight (10.94 g, 21.99 mmol, 87.0% pure.)

Monohook Tripyrrane $4_H$:

All the glassware was oven dried. A three-neck 500 ml round-bottom flask set with a mechanical stirrer, a thermometer, a 0° C. bath, and an addition funnel set with an argon line was charged with methylester diacid tripyrrane $4_F$ (10.20 g, 17.83 mmol). Trifluoroacetic acid (32.5 ml) was dripped into the reaction flask from the addition funnel over a 45 minute period keeping the flask contents below 5° C. The resulting reaction solution was stirred at 0° C. for 15 minutes, and then at 20° C. for three hours. Triethylorthoformate (32.5 ml) was dripped into the flask from the addition funnel over a 20 minute period keeping the flask contents below −25° C. by means of a dry ice/ethylene glycol bath. The reaction solution was stirred for one hour at −25° C. and then a 0° C. bath was set up. Deionized water (32.5 ml) was dripped into the reaction flask from the addition funnel keeping the flask contents below 10° C. The resulting two phase mixture was stirred at room temperature for 75 minutes and then added 1-butanol (200 ml.) The solvents were removed under reduced pressure. The resulting dark oil was dried under high vacuum overnight to obtain black solids (11.64 g.)

A three-neck 2000 ml round-bottom flask set with a thermometer, a heating mantle, a magnetic stirring bar, and a reflux condenser attached to an argon line, was charged with the crude methylester diformyl tripyrrane $4_G$ (11.64 g), methyl alcohol (900 ml), deionized water (60 ml), and lithium hydroxide monohydrate (4.7 g.) The flask contents were heated, stirred under reflux for two hours, cooled down to room temperature, added deionized water (250 ml), acidified with 12N aq. HCl to pH 5, and then stirred at 0° C. for one hour. The resulting mixture was filtered over medium fritted glass funnel. The collected solids were dried under high vacuum to constant weight prior to their purification by column chromatography (silica gel, MeOH in $CH_2Cl_2$, 0–10%; 3.64 g, 8.06 mmol, 45.2% yield.)

The monohook tripyrrane $4_E$ is condensed with a derivatized ortho-phenylene diamine, for example, $1_G$ to form a nonaromatic precursor which is then oxidized to an aromatic metal complex, for example, $4_I$. An oligonucleotide amine may be reacted with the carboxylic acid derivatized texaphyrin $4_I$ to form the conjugate $4_J$ having the site-directed molecule on the T portion of the molecule rather than the B portion.

EXAMPLE 5

Hydrolysis of Monoesters by Lanthanide (III) T2B2 Texaphyrin

The present example provides the utility of the present invention in the use of texaphyrin metal complexes for the hydrolysis of monoesters, in particular, the hydrolysis of UpU, cUMP, 3'-UMP and 2'-UMP.

Cytosine, uridine, uridine-2' and 3'-monophosphate disodium salt (2'-UMP and 3'-UMP), uridine-2',3'-cyclicmonophosphate sodium salt (cUMP), and uridylyl(3'→5') uridine ammonium salt (UpU) were purchased from Sigma (St. Louis, Mo.) and used without further purification. The lanthanide texaphyrins were prepared as in the previous examples. All solutions, unless otherwise stated, were prepared from a stock solution of 5.0 mM N-(2-hydroxyethyl) piperazine-N'-ethanesulfonic acid (HEPES), in Milli-Q purified water, adjusted to pH 7.0. Solutions were stored and reactions conducted in RNAse free plastic vials further sterilized by heating at 120° C. for 20 minutes in an autoclave. Gloves were worn at all times during solution preparation and reaction sampling. All kinetic runs were thermostated at 37° C. in a water bath.

High-performance liquid chromatography (HPLC) was performed on a Waters 501 equipped with a Waters model 440 absorbance detector, monitoring at 254 nm. A YMC, Inc., USA ODS-AQ column (150 mm×4.6 mm I.D.) was used. Satisfactory separation was achieved with an isocratic gradient (10 mM $NaH_2PO_4$ adjusted to pH 5.6 with 1% methanol) with a flow rate of 1.0 ml/min. A Beckman DU-7 spectrometer was used to confirm the concentrations of EuB2T2 txp.

$Eu(NO_3)_3$.

In the control experiment, the reaction solutions were prepared by diluting 100 μl of UpU (2.94 mM), 25 μl of $Eu(NO_3)_3$ (3.5 μm), and 100 μl of cytosine (0.423 mM), as internal standard, in 375 μl of 5.0 mM HEPES solution. The reactions were carried out as for EuB2T2 txp. The pseudo-zero order rate constant for the control reaction was determined to be k=(2.2±0.8)×10$^{-4}$ mM/h.

EuB2T2 txp.

In a typical kinetics experiment, the reaction solutions were prepared by diluting 100 μl of UpU (2.94 mM), 50 μl of EuB2T2 txp (7.8 mM), and 100 μl of cytosine (0.423 mM), as internal standard, in 350 μl of 5.0 mM HEPES solution. The rate of UpU hydrolysis was monitored by removing 15 μl aliquots which were frozen until HPLC analysis was possible. All samples were microfiltered (0.2 μm) prior to injection on the HPLC. All runs were performed in triplicate. The background as determined from the simultaneous control containing no metal complex was negligible. The pseudo-zero order rate constant for the reaction was determined to be k=(9.1±1.6)×10$^{-4}$ mM/h at 37° C., pH 7.0.

The pseudo-zero order rate constant for the hydrolytic cleavage of a ribodinucleotide by the nitrate salt of the water soluble EuB2T2 texaphyrin has been examined. Investigations indicate that a 0.15 mM aqueous solution of Eu(B2T2 txph)$^{2+}$ hydrolytically cleaved uridylyl (3'→5') uridine, UpU, (0.49 mM) with a pseudo-zero order rate of (9.1±1.6)×10$^{-4}$ mM/h at 37° C., pH 7.0. In the absence of the metal complex no evidence of RNA cleavage was observed by HPLC. The reaction was followed by HPLC, monitoring the formation of uridine. Uridine-2'-monophosphate, uridine-3'-monophosphate, and uridine-2':3'-cyclicmonophosphate (cUMP) were also observed by HPLC; this indicates a hydrolytic rather than an oxidative mechanism for the cleavage reaction. Uridine-2':3'-cyclicmonophosphate reached a steady state concentration, implying that the texaphyrin complex hydrolyzed cUMP as well. Under identical conditions, a 0.15 mM aqueous solution of $Eu(NO_3)_3$ has a pseudo-zero order rate constant of 2.2±0.35)×10$^{-4}$ mM/h. Therefore, small traces of free metal ions cannot account for the hydrolysis observed in the presence of the texaphyrin metal complex. Under these conditions, the Eu(III) complex of HAM displayed a pseudo-zero order rate constant of 4.1×10$^{-4}$ mM/h. Thus, the texaphyrin complex is found to be more effective than the HAM system.

A survey of other lanthanide (III) complexes of the B2T2 texaphyrin indicates that these complexes are also capable of RNA hydrolysis. Results are summarized in Table 1.

TABLE 1

| Rate Constants (Pseudo-Zero Order) for the Hydrolysis of UpU by Lanthanide (III) B2T2 Texaphyrin Complexes[a] | |
|---|---|
| LANTHANIDE CATION | k mM/h |
| La(III) | 1.16 × 10$^{-4}$ |
| Nd(III) | 4.69 × 10$^{-4}$ |
| Sm(III) | 6.3 × 10$^{-4}$ |
| Eu(III) | 4.99 × 10$^{-3}$ |
| Gd(III) | 1.44 × 10$^{-4}$ |
| Dy(III) | 6.0 × 10$^{-3}$ |
| Tm(III) | 4.16 × 10$^{-4}$ |
| Lu(III) | 1.91 × 10$^{-4}$ |

[a]The concentrations of the Lanthanide(III)B2T2 txph(NO$_3$)$_2$ are all approximately 0.25 mM.

Figure 9:
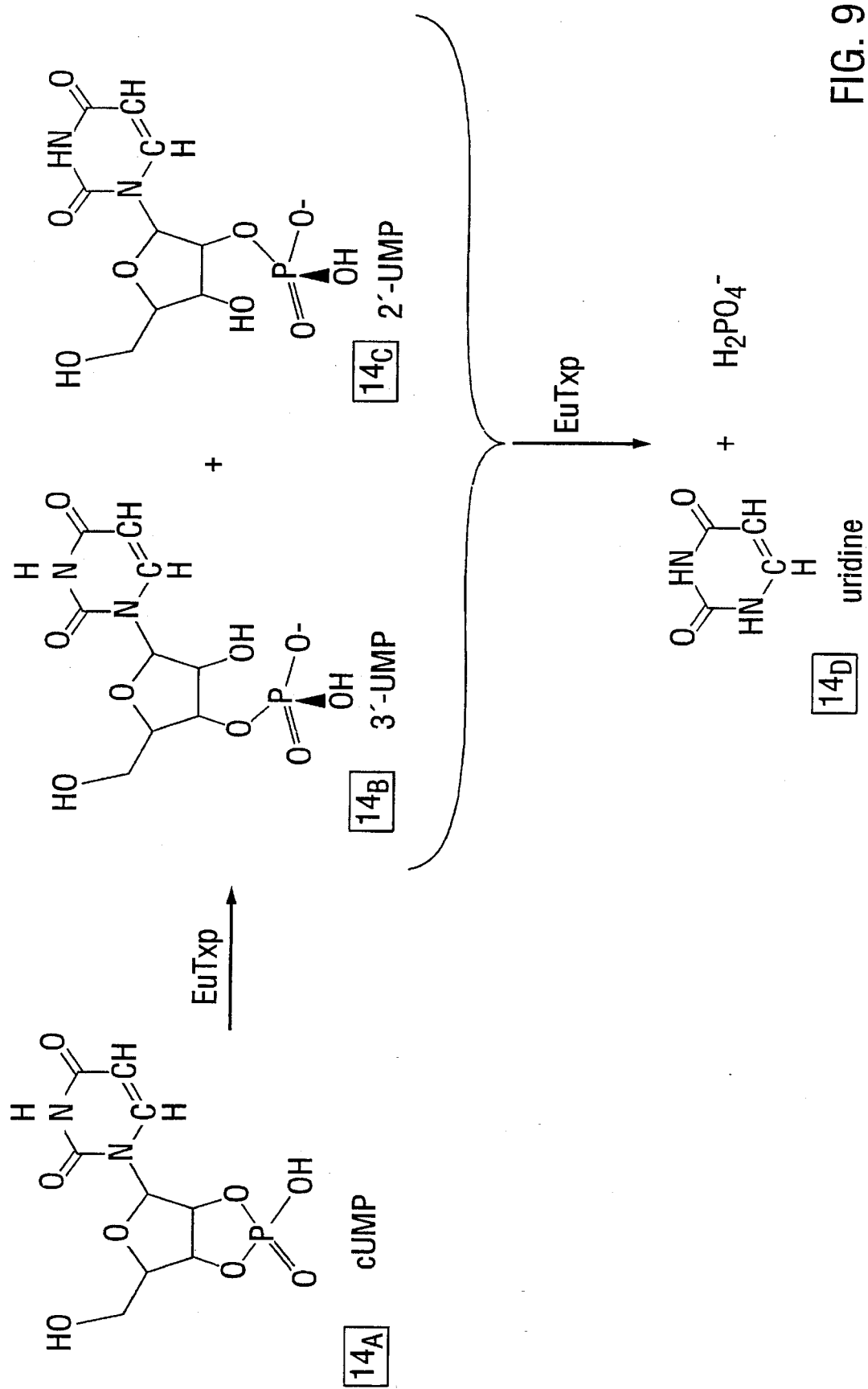
FIG. 9 shows the hydrolysis of cUMP to uridine in the presence of EuTXP.

Further evidence supporting the catalytic effect of the texaphyrin metal complex was obtained by monitoring the formation of uridine produced from the Eu(T2B2Txp)$^{+2}$ catalyzed decomposition of uridine-2',3'-cyclicmonophosphate (cUMP). The decomposition of cUMP (0.10 mM) catalyzed by Eu(T2B2Txp)$^{+2}$ (0.15 mM), when incubated at 37° C. and pH=7.0 (5 mM HEPES buffer), had a pseudo-zero order rate of $6.94 \times 10^{-5}$ mMh$^{-1}$ for the production of uridine. Examination of the reaction products by HPLC indicated that initially, cUMP is isomerized to uridine-3'-monophosphate (3'-UMP) and uridine-2'-monophosphate (2'-UMP) which are subsequently hydrolytically cleaved to produce uridine (FIG. 9).

EXAMPLE 6

Generalized Hydrolysis of RNA Using a Texaphyrin Metal Complex

This example describes the degradation of a homogenous population of RNA molecules with europium texaphyrin. P$^{32}$-labelled RNA transcripts from an isolated clone was the homogenous RNA substrate. The transcripts and their degradation products were visualized by polyacrylamide gel electrophoresis and autoradiography.

pGEM®-3Z vector and Riboprobe® RNA transcript systems were obtained from Promega Corporation, Madison, Wis. A 4.3 kb fragment of the mouse 1b Multi Drug Resistant gene (MDR) was cloned into the EcoRI site of the pGem 3Z vector and its orientation determined (see FIG. 5). The plasmid was used in transcription reactions and when digested with BamHI, T7 RNA polymerase makes a transcript from this template that is approximately 2000 bases long. The transcription reaction consisted of 100 ng of BamHI digested pGem 3Z/4.3 MDR#3, 20 µl of 5X transcription buffer, triphosphate nucleotides (A,C,G) at 500 µM, UTP at 100 µM, 50 µC of $^{32}$P α-UTP (3000 Ci/mmol), 10 mmol DTT, 120 units of RNasin and 70-100 units T7 RNA polymerase. This reaction was brought up to a total volume of 100 µl with DEPC treated double distilled water. The reaction was allowed to incubate at 37° C. for 1.5 hours. The entire reaction volume was then run over a G-50 Sephadex column (Nick column, Pharmacia) pre-equilibrated with 20 mM Tris pH 7.0, 2 mM EDTA, 0.1% SDS. The transcript was eluted from the column in the second 400 µl volume applied to the column. Any unincorporated nucleotide was left on the column.

Ten µl aliquots of the transcript were put into separate tubes and stock solutions of Eu(III)txp, EDTA or Eu(III) acetate were added so that the final volume was 20 µl. The tubes were allowed to incubate for 2 hr at 37° C. Thirty µl of dye mix (formamide, 0.2% bromphenol blue) was added to each tube. The tubes were mixed and heated at 60° C., 5 min, then the entire content of the reaction was loaded onto a 5% 8M urea polyacrylamide gel and electrophoresis was performed. The RNA transcripts incubated with europium B2T2 txph were loaded as follows: Lane 1, control, no EuB2T2 txph; lane 2, control with EDTA; lanes 3-7, EuB2T2 txph, 100 µM, 50 µM, 25 µM, 10 µM and 5 µM; lanes 8-10, EuB2T2 txph, 100 µM and EDTA at 500 µM, 300 µM and 100 µM; lane 11, M.W. std; lane 12, control, no EuB2T2 txph; lane 13, EuB2T2 txph, 100 µM and EDTA, 10 µM.

The autoradiogram showed the results of the digests of the 2000 base long transcripts with EuB2T2 txp. There was one band in the control and control with EDTA lanes 1, 2 and 12. This band was absent in the lane with 100 µM EuB2T2 txp, lane 3. An increase in lower molecular weight material, i.e. degradation products, was seen as smearing throughout lane 3. The transcript remained intact at the lower EuB2T2 txp concentrations, lanes 4-7. The transcript was degraded with 100 µM EuB2T2 txp in the presence of 500, 300, 100 and 10 µM amounts of EDTA, lanes 8-10 and 13. This experiment eliminates the possibility that free metal in the B2T2 txp solution was causing the degradation. Line 11 contained molecular weight standards of 1418 and 679 bases. Control experiments where RNA transcripts were incubated with europium acetate and with EuOAc and EDTA. Lane 1, control, no EuOAc; lane 2, control with EDTA, no EuOAc; lanes 3-7, EuOAc, 100 µM, 50 µM, 25 µM, 10 µM, and 5 µM; lane 8, EuOAc, 100 µM and EDTA 500 µM; lane EuOAc, 100 µM and EDTA, 300 µM; lane 10, EuOAc, 100 µM and EDTA, 100 µM; lane 11, EuOAc, 100 µM and EDTA, 10 µM; lane 12, MW std; lane 13, control, no EuOAc; lane 14, MW std. that the 100, 50, 25, 10 and 5 µM-concentrations of free Europium metal salt (EuOAc) did not digest the transcript, lanes 3-7. These results were not affected by the presence of EDTA, lanes 8-11.

A digestion of total RNA (primarily 28s and 18s ribosomal RNA from K562 cells) with EuOAc, EuT2B2 txp and GdT2B2 txp indicated that all are able to hydrolyze total RNA. The digestions were performed in 50% DMSO and H$_2$O, the gel was electrophoresed using a 10 µM phosphate buffer, pH 6.8. It is likely that EuOAc digests the homogeneous transcript also but at higher EuOAc concentrations than those used in the present example.

Clearly, EuB2T2 txph is able to hydrolyze RNA substrates. Since the texaphyrins have such versatility for functionalization, this result has significant implications for the construction of site-specific cleaving reagents for nucleic acids and other molecules as discussed further in Examples 7 and 8.

EXAMPLE 7

Figure 6:
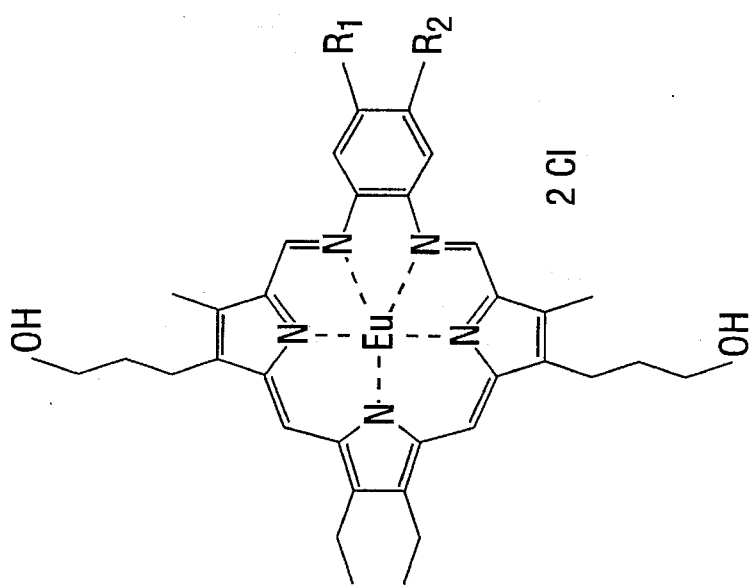
FIG. 6 shows preferred texaphyrin-europium complexes of the present invention.

Site-Specific Hydrolysis of RNA by Europium(III)-Texaphyrin Conjugated to a Synthetic Oligodeoxyribonucleotide The present example provides antisense agents using a texaphyrin metal complex-oligonucleotide conjugate that effects the hydrolysis of its RNA complement without the participation of endogenous nucleases. A DNA-EuTx-oligonucleotide conjugate was synthesized based on the functionalized texaphyrin 8$_B$, FIG. 6, (2$_F$, FIG. 2A and FIG. 2B). This "ribozyme analogue" (cf., 8$_C$) provides an example of oligodeoxynucleotide-directed, metal catalyzed hydrolysis of a complementary RNA oligomer.

Figure 7:
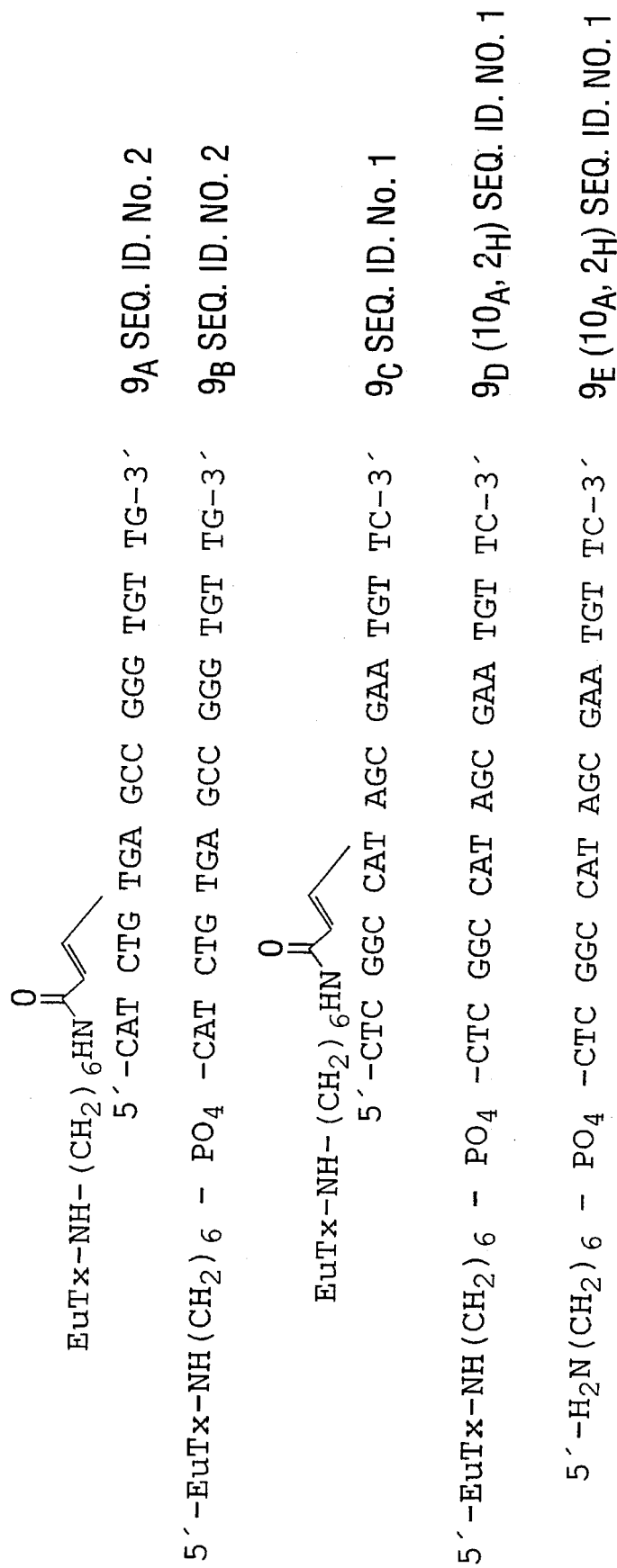
FIG. 7 shows four europium (III) texaphyrin (EuTx) DNA conjugates of Example 7.

Two 20-mer oligonucleotides were machine-synthesized to contain alkylamine groups at either the 5-position of an internal thymine residue or the 5'-end terminal phosphate. Oligodeoxynucleotide-amines modified on the 5-position of thymine were purchased from Oligo's Etc. (Wilsonville, Oreg.); oligodeoxynucleotide-amines modified on the 5' end were purchased from Keystone Laboratories, Inc. (Menlo Park, Calif.). Oligonucleotides were HPLC purified and precipitated using LiCl prior to use. Reaction of the carboxylic acid functionalized europium(III) texaphyrin complex 8$_B$ with carbodiimide and N-hydroxysuccinimide produced the corresponding activated ester, which was added directly to a solution of the chosen oligodeoxynucleotide amine. The resulting DNA-EuTx conjugates (FIG. 7) were purified by electrophoresis.

Figure 8:
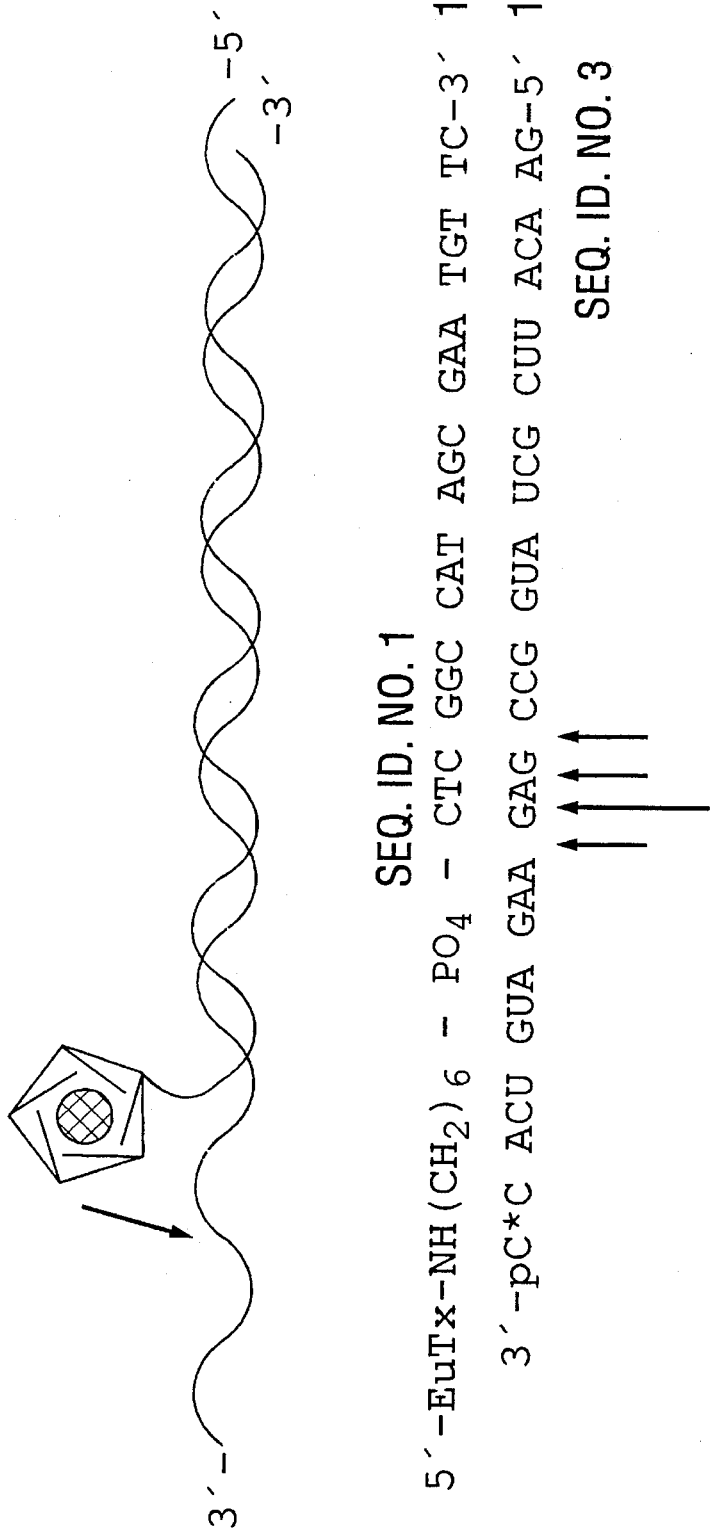
FIG. 8 shows a schematic representation of cleavage of an RNA 30-mer by EuTx-DNA conjugate; the arrows show sites of metal-catalyzed hydrolysis.

A synthetic RNA 30-mer (10$_B$, FIG. 8) was obtained as substrate (Keystone Labs, Inc., Menlo Park, Calif.), with a sequence selected from a unique site within the gene transcript for multiple drug resistance. Sequence is complementary at 1562 bases post-transcriptional start site in mouse multidrug resistance protein mRNA. The 3'-$^{32}$P-labelled substrate was incubated with an excess of oligodeoxynucleotide conjugate at 37° C. for 18–24 h in a buffered salt solution, ethanol precipitated, and assayed on a 20% denaturing polyacrylamide gel. As illustrated schematically in FIG. 8. The synthetic RNA 30-mer $10_B$ by incubated with EuTx-DNA conjugates or free europium complex $8_B$. A 20% high resolution denaturing polyacrylamide gel was run with sample where the substrate was labelled with $^{32}$P at the 3' end. Ca. 1.5×10$^5$ cpm of substrate was incubated for ca. 24h at 37° C. in a total volume of 20 μL of buffer containing 50 mM HEPES, pH 7.5, 100 mM NaCl, 25 μM EDTA and 5 μg/mL calf thymus DNA and analyzed as follows: lane 1, no DNA control; lane 2, control with unmodified oligodeoxynucleotide $9_g$; lane 3, 2.5μM $8_B$; lane 4, 25 μM $8_B$; lanes 5–7, $9_E$ and 250 nM, 2.5 μM, and 25 μM $8_B$, respectively; lane 8, $9_A$; lane 9, $9_C$; lane 10, $9_B$; lanes 11–14, $9_D$ at 2.5 nM, 25 nM, 250 nM, and 2.5 μM, respectively. All other oligonucleotides were at 2.5 μM final concentration. Nucleotide sequence analysis was determined by partial digestion with base-specific ribonucleases: Ti(G); U2 (A>G); Phy M (U+A); B, cereus (U+C); HCO$_3$ (alkaline hydrolysis); PNK (polynucleotide kinase-treated HCO$_3$ lane). The autoradiogram showed cleavage of the synthetic RNA 30-mer $10_B$ incubated with EuTx-DNA conjugates or free euorpium complex $8_B$, ca. 30% cleavage occurred near the expected location of the europium (III) texaphyrin complex upon hybridization with conjugate $10_A$. Cleavage yield was measured by densitometry and calculated as ratio of cleavage band to intact material. The corresponding cleavage bands were not observed when this same substrate was incubated with oligonucleotides that were non-complementary in sequence, unmodified, or were modified internally with the complex (lanes 8–10). Experiments were conducted to test the effect of various buffer conditions on the cleavage of 5' end labelled RNA 30-mer $10_B$ by EuTx-DNA conjugate $10_A$ ($9_D$). Labelled substrate was incubated with 2.5 μM EuTx-DNA conjugate for 24h at 37° C. (lanes 3–6) or 25° C. (lanes 7–14) in buffers containing 100 mM NaCl and analyzed as follows: lane 1, non-incubated RNA control; lane 2, ribonuclease T1 (G) reaction; lanes 3, 8, 50 mM HEPES, pH 7.5, 25 μM EDTA; lanes 4, 9, 50 mM HEPES, pH 7.0, 25 μM EDTA; lane 5, 10:50 mM TrisAcetate pH 7.5 25 μM EDTA; lanes 6, 11, 14, 50 mM TrisAcetate pH 7.0, 25 μM EDTA; lane 7, 50 mM HEPES, pH 7.5; lanes 12, 13, 50 mM TrisAcetate, pH 7.0; lane 13, 5 μM Fe(II), 4 mM DTT, 5 μM non-modified oligo $9_E$; lane 14, no conjugate control. EuTx: conjugate-derived cleavage; Bkgd: background autocleavage.

Further experiments were conducted to test the effect of addition of calk thymus DNA on the cleavage of 5'- end labelled RNA 30-mer $10_B$ by EuTx-DNA conjugate $10_A$ ($9_D$). Labelled substrate was incubated for 25h at 37° C. in 50 μM HEPES (or TrisAcetate, lane 6) buffer containing 100 mM NaCl, 25 μM EDTA, and 5 μg/mL calf thymus DNA and analyzed as follows: lane 1, no DNA control; lane 2, non-modified oligodeoxynucleotide $9_E$ (2.5 μM); lane 3, $9_B$ (2.5 μM); lane 4, $9_C$ (2.5 μM); lanes 5–9, $9_D$ ($10_A$) (250 nM). EuTx; conjugated cleavage: Bkgd: background autocleavage. These control reactions indicate that ambient light, calf thymus DNA or type of buffer (Tris acetate or HEPES, EDTA, pH 6.0–8.0) had no apparent effect on cleavage efficiency. EDTA inhibits cleavage by free lanthanide (III) cations as observed in Morrow et al. (1992).

The cleavage fragments co-migrate with bands in sequencing lanes produced by incubation of substrate under alkaline conditions or subjected to partial digestion with a series of base-specific ribonucleases (For an example of a similar endproduct analysis, see Dange et al., 1990). This observation is consistent with a hydrolytic mechanism, presumably involving the EuTx acting as a Lewis acid that facilitates an intramolecular attack of the 2'-hydroxyl group to effect cleavage. There are bands indicating site-specific cleavage of the ribonucleotide target sequence in the absence of any added cleavage reagents. Although the source of this background cleavage is unknown, it is believed to be the direct result of a higher order structure (ie., a hairpin) of the oligoribonucleotide, since hybridization with any complementary oligonucleotide dramatically inhibits the cleavage. This type of structure-dependent cleavage behavior has been seen previously with oligoribonucleotides (Dange et al., 1990, Kazabov et al., 1992).

Maximal cleavage activity of the Eu(III)Txp-oligonucleotide was observed down to 25 nM conjugate. Decreased cleavage below this level may be due to a decrease in hybridized material (as judged by increased background cleavage of the target RNA present at a concentration of about 1 nM). By means of comparison, the free europium complex non-specifically hydrolyzed the RNA substrate at 25 μM. In the control reaction containing both complex and the non-derivatized complementary DNA oligomer, cleavage occurred predominantly in the single stranded region, although still at lower efficiency than the Eu-Tx-DNA conjugate at 2.5 nM. Thus, attachment of the EuTx to the DNA probe increases its effective concentration ca. 10,000-fold. A target RNA without the secondary structure observed here would likely allow for cleavage at lower DNA-EuTx concentrations. These data indicate the utility of such conjugates in antisense applications.

As demonstrated in the present example, the selectivity of the texaphyrin complexes is enhanced by covalently linking oligonucleotides onto the periphery of the macrocycle. Since the metal complexes do cleave RNA over DNA preferentially, the DNA appendages would remain intact during the hydrolysis experiments. The DNA arm will recognize and bind to an appropriate RNA segment, effectively increasing the metal concentration at these loci relative to the overall metal concentration in solution. Phosphate ester hydrolysis will therefore be significantly increased at specific locations along the RNA backbone. In one embodiment, primers (known or deduced) for PCR could be coupled to a hydrolytic divalent or trivalent texaphyrin complex to induce hydrolysis of proximal RNA or DNA.

The use of texaphyrin metal complexes to cleave RNA in vivo as a treatment procedure relies on the effective localization of the complex to the site of desired cleavage. A site of desired cleavage may be a position novel to undesired organisms in terms of health care. A site of desired cleavage may be a messenger RNA encoding a product deleterious to the host or may be a normal RNA that is deleterious in some way.

The data of examples 6 and 7 demonstrate that lanthanide texaphyrin complexes may be developed into RNA antisense reagents. The anti-sense approach is efficient in regulating the expression of proteins. Many copies of a particular polypeptide are made from one messenger RNA molecule; therefore, by moving up in the levels of cellular processes and knocking out the message, fewer attacking agents would be required because there would be fewer target sites. The anti-sense strategy provides a clear and rational method for new drug design because there is one requirement, that the anti-sense probe hybridize to its target molecule. The hybridization requirement is very well understood via complementary Watson-Crick base pairing. Unlike the present methods in the art which require screening of thousands of compounds and X-ray crystal structure analysis, the information needed for anti-sense technology is the sequence of the target. Treating native RNA with this new texaphyrin complex results in the texaphyrin complex binding to a complementary RNA or DNA sequence via an appended oligonucleotide. The lanthanide texaphyrin complex then cleaves the RNA or DNA proximal to this specific site. Either one or two texaphyrin molecules may be attached to the DNA, creating the potential for gene splicing reagents.

The texaphyrin oligo complex would have immediate applications for anti-viral and anti-bacterial therapy as well as cancers (an oligonucleotide complementary to an oncogene, for example) and inflammatory responses that are caused by the overexpression of certain proteins. Antisense technology is discussed in U.S. Pat. Nos. 5,194,428, 5,110,802 and 5,216,141, all of which are incorporated by reference herein.

EXAMPLE 8

Texaphyrin-Sapphyrin Conjugates for Ester Cleavage and Transport Across Membranes A further means of gaining selectivity is to link covalently the texaphyrin complex to a sapphyrin (sap) molecule, (Sessler et al., 1992; Furuta et al., 1991; Sessler et al., 1991; U.S. Pat. No. 5,159,065; U.S. Pat. No. 5,120,411; U.S. Pat. No. 5,041,078, all incorporated by reference herein). Since sapphyrins bind phosphate, $K=20$ $M^{-1}$ in water at pH 7, the linked texaphyrin-sapphyrin complex (txph-sap) could effectively increase the metal concentration at locations adjacent to the sapphyrin binding sites. Since the txph-sap molecule would be quite large it is expected that the ternary structure of RNA will provide a limited number of favorable binding sites. Thus, a degree of structural selectivity for RNA hydrolysis would be expected, with this selectivity being based on the conformations of the substrate molecules.

Figure 10:
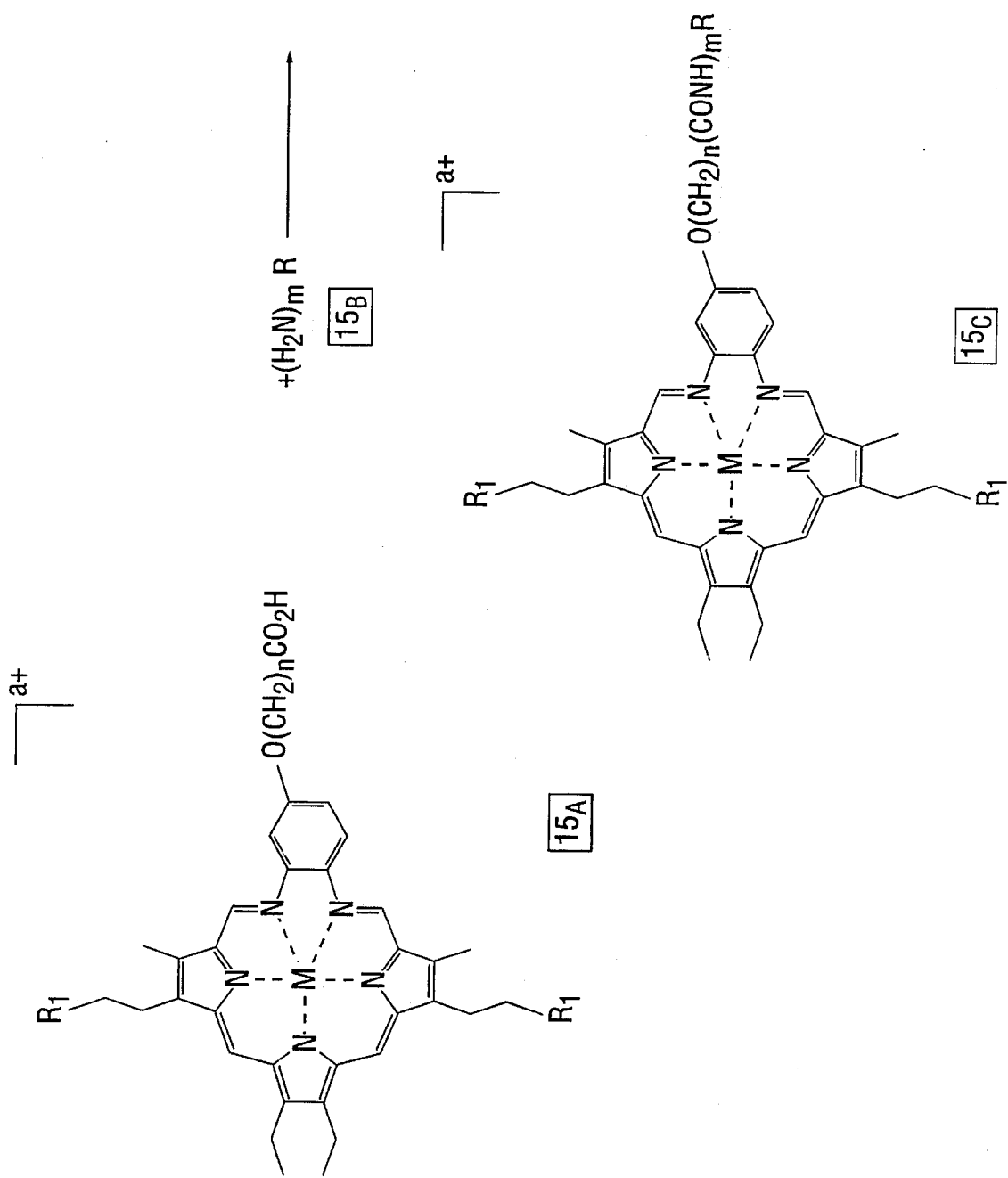
FIG. 10 shows the formation of amide linked derivatives of texaphyrin: R=sapphyrin, texaphyrin or porphyrin; $(NH_2)_m$—R represents diamines $NH_2$—$(CH_2)_n$—$NH_2$, n=2–12; triamines $NH_2(CH_2)_n)_3N$, n=2–6; or tetramines $(NH_2(CH_2)_n)_2N((CH_2)_nNH_2)_2$, n=2–4, m=2–6.

The synthesis of (Eu)texaphyrin-sapphyrin conjugate (FIG. 10 and FIG. 11):

Synthesis was accomplished by amide bond formation between activated (Eu)texaphyrin carboxylic acid and amino-substituted sapphyrin. By the same strategy, a variety of texaphyrin-sapphyrin conjugates may be prepared including conjugates where other metallic cations may be incorporated into the texaphyrin moiety. FIG. 10 shows the formation of exemplary amide linked derivatives of texaphyrin.

Figure 11A:
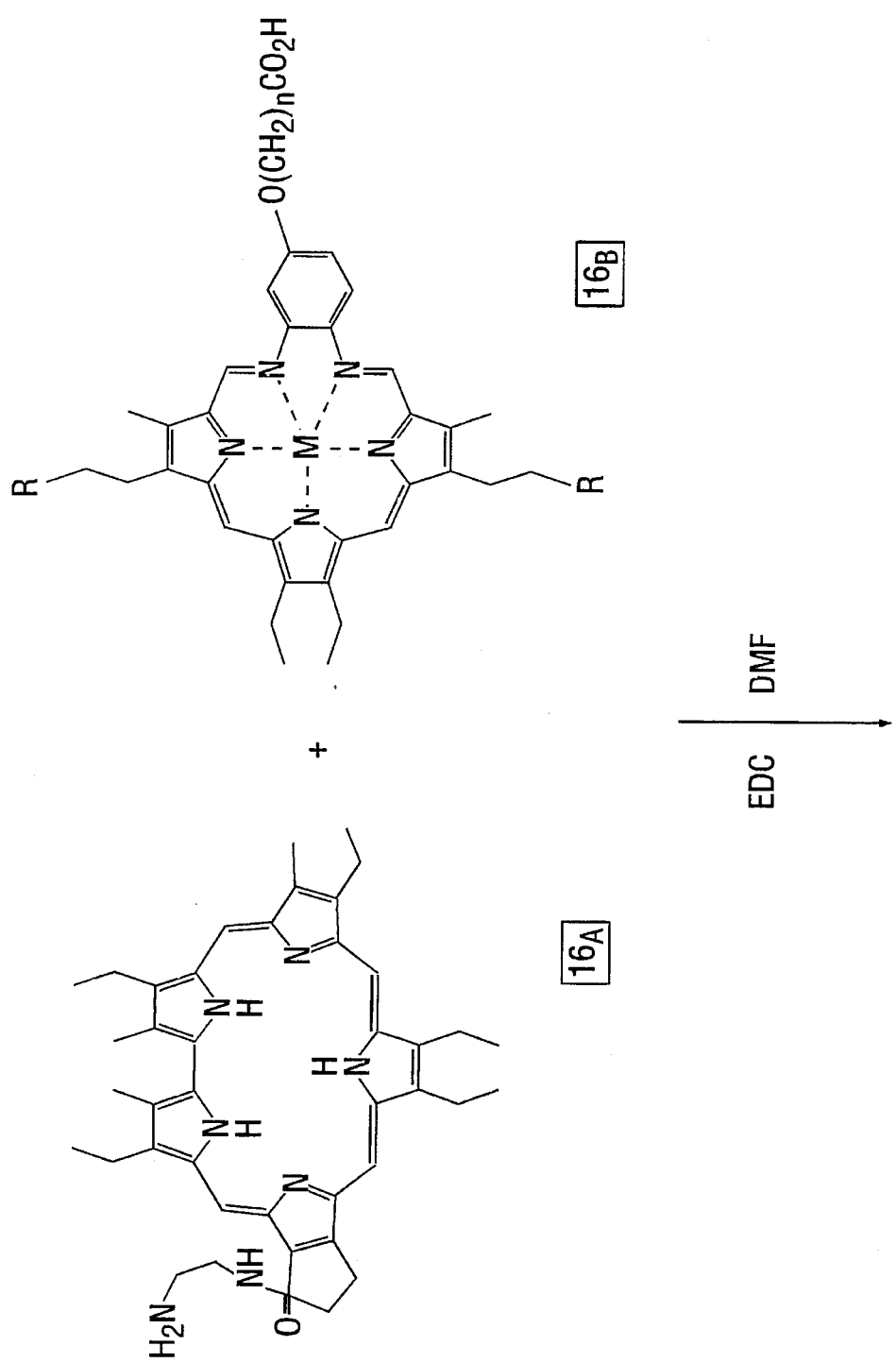
FIG. 11 shows the synthesis of a texaphyrin-sapphyrin conjugate, R may be H, OH, alkyl, hydroxyalkyl or oxyalkyl, M=Ln and n=1–5.
Figure 11B:
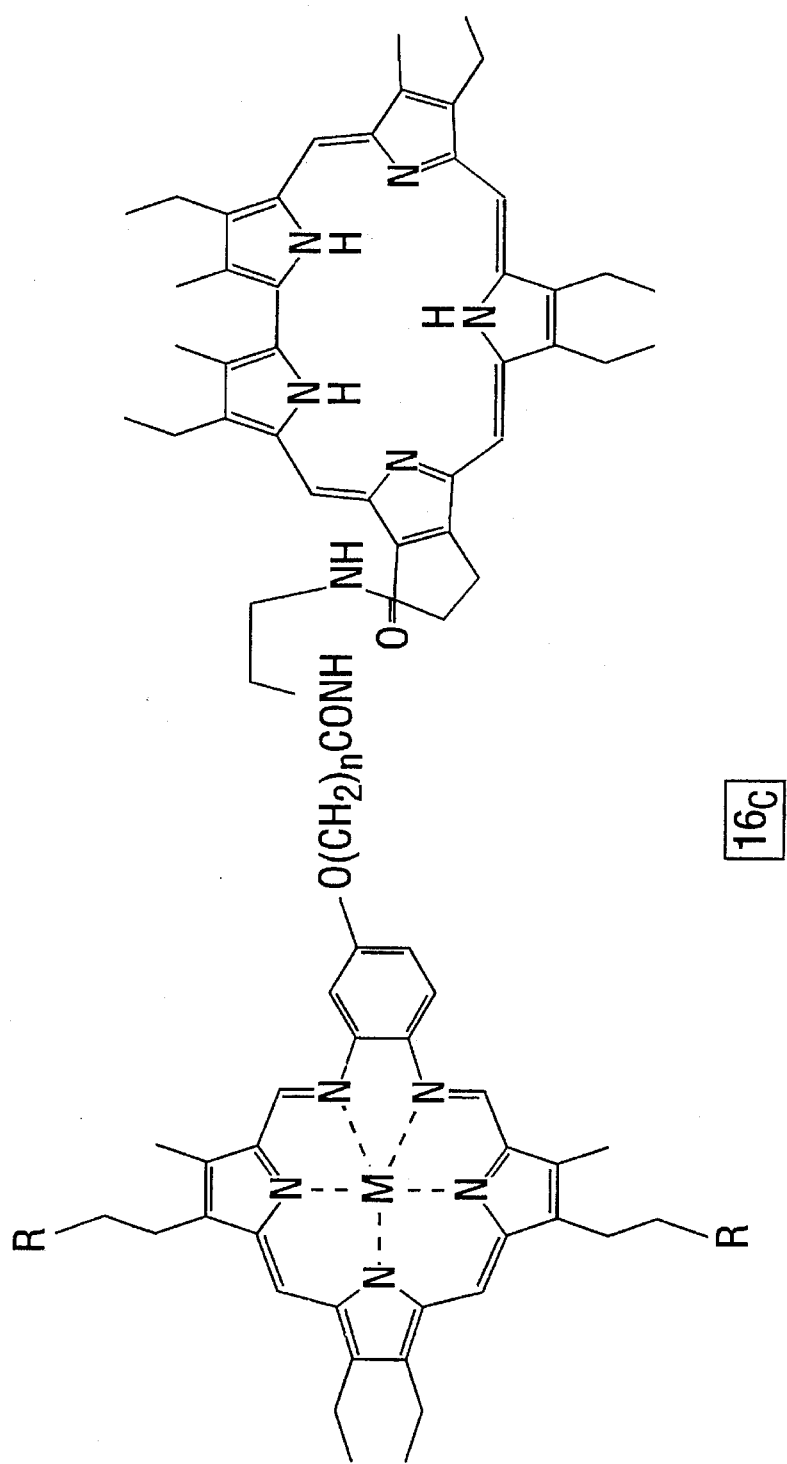

The synthesis of (Eu)texaphyrin acid EuT2B1(O(CH$_2$)$_3$CO$_2$H) $16_B$, R=CH$_2$OH, FIG. 11.

Texaphyrin derivative (T2B1(O(CH$_2$)$_3$CO$_2$H).HCl, 0.694g, 1 mmol) was dissolved in 80 ml of dry methanol. Eu(OAc)$_3$.H$_2$O (0.329 g, 1 mmol) was added, followed by triethylamine (0.5 ml). The reaction mixture was refluxed (reflux condenser was open to the air) for 6 hours, with the progress of metallation followed by visible spectra. Methanol was evaporated under reduced pressure to give a dry, dark solid which was washed with dichloromethane under vigorous stirring for 2 hours. The product was filtered off, redissolved in MeOH (25 ml), and the solution was treated with zeolite (by standard procedure for removing free europium salt). The product was twice precipitated from methanol by adding diethylether. The collected dark green solid was dried under high vacuum overnight. Yield 91.0%. Characterization data: Elemental analysis for $C_{38}H_{44}N_5O_5Eu.2(OAC)$ (F.W. 920.855) calc. 54.78% C, 5.47% H, 7.61% N; found 54.46% C, 5.50% H, 7.55% N. FAB HR MS: For $C_{38}H_{43}N_5O_5Eu$ calc. 802.24626; found 802.247752. UV-Vis (EtOH, $\lambda_{max}$): 420, 469, 760 nm.

The Synthesis of EuTexaphyrin-Sapphyrin derivative ($16_C$, FIG. 11):

Texaphyrin dihydroxyl, carboxylate derivative as described above (0,092 g, 0.1 mmol) was dissolved in 10 ml dry dimethylformamide (solvent without dimethylamine). The solution was cooled on ice to 0° C. The activating agent (carbodiimide, EDC, 95.5 mg, 0.5 mmol) and hydroxybenzotriazole (5 mg) were added and the mixture was held at 0° C. for 45 minutes. For the preparation of the aminosapphyrin derivative $16_A$, the sapphyrin monocarboxylic acid was, after activation with DCC, reacted with t-BOC monoprotected ethylenediamine and then subsequently deprotected by treating with TFA at room temperature for 1 hour. The solution of aminosapphyrin derivative 3,8,17,22-tetraethyl-12-[N-(2-aminoethyl)aminocarbonylethyl-2,7,13,18,23-pentamethylsapphyrin ($16_A$ 0,067 g, 0.1 mmol) in 5 ml of dimethylformamide and 0.1 ml of dry pyridine was added at the same temperature. The reaction mixture was kept at 0° C. for 30 minutes, allowed to warm to room temperature, and stirred for 3 days. Solvent was evaporated under reduced pressure. The crude product was washed, dissolved in EtOH (10 ml) and diethylether was slowly added. Precipitated product was dried in vacuo. Yield 68%. Characterization data: UV-Vis $\lambda_{max}$(EtOH): 358, 431, 450, 618, 681, 761 rim. (H$_2$O, pH7): 358, 408, 455, 623, 675, 765 nm. FAB MS: For $C_{80}H_{95}N_{12}O_5Eu$ calc. 1456.67539; found 1457.

Alternative synthetic approaches to analogous heterodimers may include the coupling of amino-substituted texaphyrins (prepared by the reaction of texaphyrin carboxylate anion with monoprotected ethylenediamine H$_2$N(CH$_2$)$_2$NHR, where R is (CH$_3$)$_3$COCO-(t-BOC), followed by heating to 180° C. to effect deprotection) with activated sapphyrin monocarboxylic acid derivatives (e.g., sapphyrin acid chloride, or the products obtained from treatment with dicylohexylcarbodiimide, DCC).

This compound $16_C$ was tested (a) for transport of ADP and ATP across bulk liquid membrane. Efficient transport at neutral pH was observed, and (b) phosphodiester hydrolysis—during ATP transport, AMP was formed as a result of hydrolysis. Transport studies were performed using an H$_2$O—CH$_2$Cl$_2$—H$_2$O three phase Pressman-type U-tube type model membrane system (Araki et al., 1990). Aqueous phase I (source phase) was 5 mM solution of ADP, ATP at pH 7.0, the organic phase was 0.1 mmol solution of (Eu)texaphyrin-sapphyrin conjugate. Aqueous phase II (receiving phase) was water, pH 7.0. The increase in concentration of ADP and ATP in the receiving phase as a result of membrane transport was followed as a function of time. Quantities transported were determined by HPLC analysis of receiving phase using cytosine and/or adenosine as the internal standard(s) (reverse phase analytical column, 10 mM phosphate buffer, pH 5.6). In this way the initial transport rates for the through-membrane transport of ADP and ATP were derived. Results show that the initial rate of transport for ADP is in range of $5\times10^{-9}$ mol/cm$^2$.h and about five times lower than this for ATP. During the course of the above-described through-membrane transport of ADP and ATP the formation of a new compound in the receiving phase, determined to be AMP by comparison with an authentic sample, was also observed. Since this AMP material was not present in the source phase nor observed when carrier-free control experiments were carried out, its production as the result of the (Eu)texaphyrin-sapphyrin conjugate mediated transport process is taken as indicating that the conjugate is capable of effecting the hydrolysis of a phosphodiester bond.

Texaphyrin-sapphyrin conjugates or analogs thereof should be very useful in antisense applications: Sapphyrin binds to phosphate diesters, such as those of DNA, with high specificity and affinity. Ln(III) texaphyrins bind to anionic phosphates and effect the hydrolytic cleavage of RNA and related species. Thus, a texaphyrin-sapphyrin conjugate should provide an enhanced recognition of RNA/DNA and an improved rate of hydrolysis by virtue of the induced "neighboring group effect". Since diamagnetic metallotexaphyrins (e.g., Lu(III)-containing TXPs) are photoactive, the present invention provides for the use of the sapphyrin portion of a sapphyrin-Lu(III)texaphyrin conjugate to effect binding to a DNA substrate and then use the singlet-oxygen-generating portion of the same conjugate to effect photocleavage of this same DNA target.

Along with the potential to cleave RNA specifically the texaphyrin molecule may be designed to pass through cell membranes and selectively attack viral RNA. Such a molecule would have the potential to treat human patients infected with a variety of viruses, including HIV.

EXAMPLE 9

Figure 12:
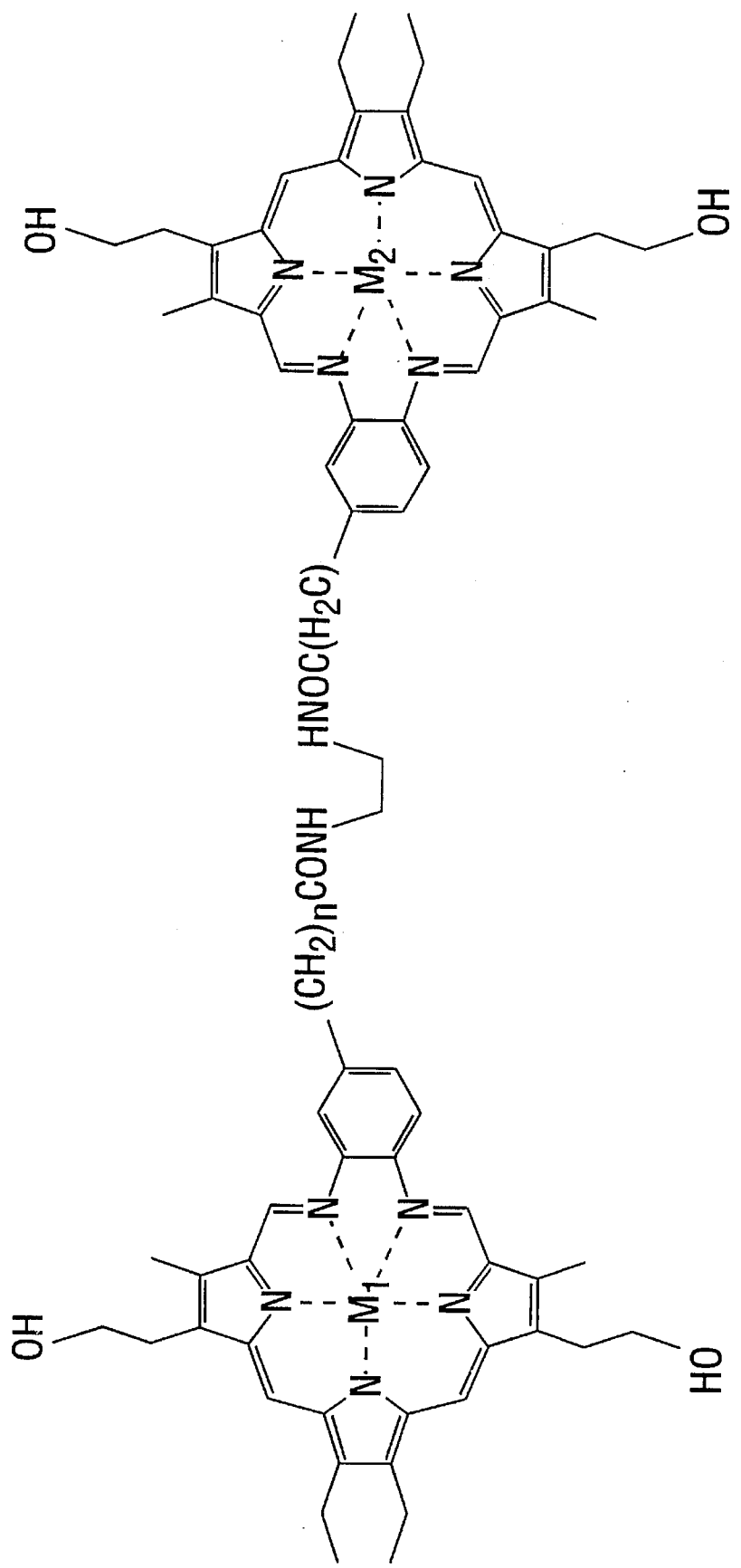
FIG. 12 shows a dimer or conjugate of texaphyrins. The metals may be the same or different.

Texaphyrin-Texaphyrin Conjugates (FIG. 12)

Texaphyrins may be coupled to form a texaphyrin-texaphyrin conjugate similar to the texaphyrin-sapphyrin conjugate described in Example 8. A carboxylate texaphryin derivative may be converted to an amino derivative by coupling with diamino compounds, such as $NH_2(CH_2)_nNH_2$, or by coupling with a monoprotected compound of the type $NH_2(CH_2)_nNHR$, where R may be a variety of protecting groups. The individual TX metal complex in a texaphyrin-texaphyrin conjugate may have the same or a different chelated metallic cation from the other TX metal complex. FIG. 12 shows a reaction product of 2 equivalents of a metallotexaphyrin (such as Eu-TX) carboxylic acid with an activating reagent, e.g. EDC, followed by coupling with an amino component, for example, ethylenediamine.

Texaphyrin metal complexes, especially paramagnetic metal complexes, bind phosphate anions, nucleotides and oligonucleotides as indicated by up to 200 ppm shifts in $^1$HNMR spectra induced by the binding of these compounds. The apparent association constant for formation of a monoadduct with diphenylphosphate monoanion in methanol/chloroform is 290 dm$^3$ mol$^{-1}$ and for formation of a diadduct is 74 dm$^3$ mol$^{-1}$. Similar changes in spectral patterns were observed from binding of phenyl phosphate dianion, phenylphosphonate monoanion, uridine 5'-monophosphate, uridine 2',3'- monophosphate, guanosine 5'-monophosphate and oligonucleotide mixtures. The lanthanide adducts of texaphyrin-texaphyrin conjugates may be useful for effecting hydrolysis of di- or triphosphate species such as ATP, hydrolysis at multiple sites in a phosphate polyester, such as RNA or for effecting simultaneous binding and hydrolysis of such RNA or DNA-type substrates. For MRI and PDT, a combined diamagnetic/paramagnetic species would allow for binding, imaging and dual cleavage possibilities via hydrolysis and photoactivation.

The use of two proximal texaphyrins should effect the hydrolysis of RNA with increased efficiency due to the concerted activity of the metal complexes. For example, one complex may act as a Lewis acid while the second serves to generate a metal-bound hydroxide general base at neutral pH. Similar mechanisms have been proposed based on crystallographic data obtained from single crystals of DNA hydrolyzing enzymes such as the 3'-5' exonuclease activity of DNA polymerase.

EXAMPLE 10

Further Uses for Lanthanide Texaphyrins Coupled to Site-Directed Molecules

U.S. Pat. No. 5,252,720 describes magnetic resonance imaging experiments with B2T2 gadolinium complex in vivo. The results show that the B2T2 gadolinium complex demonstrates in vivo affinity for tissue high in lipid content, atheroma, the liver, kidneys and tumors, and has low toxicity in rodents. As exemplified herein, the chemical properties of this texaphyrin class of macrocyclic ligands can be varied by peripheral substitution, which allows biological properties to be optimized in terms of biodistribution, pharmacokinetics and toxicity.

Texaphyrin metal complexes are especially suited for acting as bifunctional chelating agents in a variety of targeted treatment regimens. Texaphyrin-metal complexes are effective in antibody conjugate-based treatment since they have functional groups suitable for conjugation to the antibody. They form covalent linkages that are stable in vivo which do not destroy the immunological competence of the antibody, they are relatively nontoxic, and they are readily soluble in a physiological environment. A further advantage of these texaphyrins is that many would be suitable for further functionalization. Treatment of carboxylated texaphyrins with thionyl chloride or p-nitrophenol acetate would generate activated acyl species suitable for attachment to monoclonal antibodies or other biomolecules of interest. Standard in situ coupling methods (e.g. 1,1'-carbonyldiimidazole (CDI)) could be used to effect the conjugation.

Many cell membranes are partially constructed from phospholipids. Thus, lanthanide texaphyrins may be developed into synthetic specific phospholipases. One skilled in the art in light of the present disclosure could then determine precisely the lipid side chain that is connected via the phosphate ester bond in a given phospholipid. An extension of this process would be to digest cell membrane components such as phosphatidyl choline and sphingomyelin. This is important since the latter participates in nerve and brain functions.

The development of potent cytotoxins from lanthanide texaphyrins may be accomplished by developing reagents that specifically hydrolyze ATP, ADP, NADH, or FADH$_2$. Said cytotoxins may disrupt, in a biologically specific way, the flow of free energy in the cell and essentially starve the organism. This could allow for the death of undesired plants and animals or the treatment of mammalian cancers.

Liver diseases causing the accumulation of glycogen may be treated by hydrolyzing uridine diphosphate glucose (UDP), the phosphodiester precursor to glycogen. The present invention demonstrates that uridine phosphates are hydrolytically cleaved by lanthanide texaphyrins and previous work with texaphyrin (U.S. Pat. No. 5,252,720) has shown that they may localize in the liver. Thus, one skilled in the art would realize that the basic features of this approach have already been demonstrated by experiment.

Cyclic adenosine monophosphate (cAMP) is believed to play an important part in regulating various hormones. Hydrolyzing cAMP to the linear adenosine monophosphate (AMP) impedes certain hormone regulation. Texaphyrin complexes may therefore be used as hormone regulation drugs.

A further use for texaphyrin metal complexes may be as hydrolysis reagents for the detoxification of di- and trialkyl phosphate esters. Alkyl phosphate esters have a wide range of uses including solvents in chemical reactions, insecticides (e.g., parathion) and chemical nerve gases (e.g., diisopropyl phosphofluoridate, DIPF). Hydrolysis and detoxification of these agents in the environment is often slow by natural processes. Developing catalysts for the hydrolysis of alkyl phosphate esters could greatly improve the lives of many people. Texaphyrin complexes could further be developed as treatment for patients that have been exposed to such nerve agents. Here, the key feature is that texaphyrins are known to hydrolyze phosphate esters quickly.

The following references are incorporated in pertinent part by reference herein for the reasons cited below.

REFERENCES

Agrawal, S., and Tang, J. Y., *Tetrahedron Letters*, (1990) 31:7541.
Araki, T. et al., *Liquid Membranes: Chemical Applications*, CRC Press, Boca Raton, 1990.
Basile, L. A. et al., *J. Am. Chem. Soc.*, (1987) 109:7550.
Breslow, Ronald and Huang, Deeng-Lih, *Proc. Natl. Acad. Sci. USA*, (1991) 88:4080.
Browne, Kenneth A. and Bruice, Thomas C., *J. Am. Chem. Soc.*, (1992) 114 (13):4951.
Chin, Jik and Banaszczyk, Mariusz, *J. Am. Chem. Soc.*, (1989) 111:4103–4105.
Chin, Jik and Banaszczyk, Mariusz, *J. Am. Chem. Soc.*, (1989) 111:2724.
Chin, Jik et al. *J. Am. Chem. Soc.*, (1989) 111:186–190.
Chin, Jik and Zou, Xiang, *Can J. Chem.*, (1987) 65:1882.
Dange, et al., *Science* 1990, 248, 585–588.
Eichhorn, G. L.; Butzow, J. J. *Biopolymers* 1965, 3, 79–94.
England, T. E.; Uhlenbeck, O. C. *Biochemistry* 1978, 17, 2069–2076.
Furuta et al., *J. Amer. Chem. Soc.*, (1991) 113:6677.
Hayashi, N., et al., *Inorg. Chem.* 1993, 32, 5899–5900.
Hendry, Philip and Sargeson, Alan M., *J. Amer. Chem. Soc.*, (1989) 111:2521.
Kazakov, S.; Altman, S. *Proc. Natl. Acad. Sci. USA* 1992, 89, 7939–7943.
Kim, Jung Hee and Chin, Jik, *J. Am. Chem. Soc.*, (1992) 114:9792–9795.
Kolasa, et al., *Inorg. Chem.* 1993, 32, 3983–3984.
Komiyama, Makoto et al., *J. Chem. Soc., Chem. Commun.*, (1992): 640–641.
Kuchino, Y. *Methods in Enzymology* 1989, 180, 154–163.
Menger, F. M. et al., *J. Am. Chem. Soc.*, (1987) 109:2800.
Modak, Anil S. et al., *J. Am. Chem. Soc.*, (1991) 113:283.
Morrow, J. R. et al., *J. Am. Chem. Soc.*, (1992) 114:1903.
Morrow, et al., *Inorg. Chem.* 1993, 32, 4566–4572.
Ranganathan, Darshan et al., *J. Chem. Soc., Chem. Commun.*, (1993) 4:337.
Schneider, et al., *Angew. Chem. Int. Ed. Engl.* 1993, 32, 1716–1719.
Sessler et al., *Synlett*, (1991) 127.
Sessler, J. L. and Burrell, A. K., *Top. Curr. Chem. Rev.*, (1991) 161:179.
Sessler et al., *Tetrahedron*, (1992) 48:9661.
Shelton, Valerie and Morrow, Janet R., *Inorg. Chem.*, (1991) 30:4295.
Stern, Michael K. et al., *J. Am. Chem. Soc.*, (1990) 112:5357.
Sumaoka Jun et al., *J. Chem. Soc. Chem. Commun.*, (1992) 1707–1708.
Chung, Yongseog et al., *Tetrahedron Letters*, (1990) 31:5413.
U.S. Pat. No. 5,159,065.
U.S. Pat. No. 5,120,411.
U.S. Pat. No. 5,041,078.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A method of phosphate ester hydrolysis, comprising obtaining an aqueous phosphate ester solution, and incubating the solution with a texaphyrin metal complex, said incubation being under conditions and for a time sufficient to hydrolyze the phosphate ester.

2. The method of claim 1 where the metal is a divalent or a trivalent metal cation having catalytic activity for ester bond hydrolysis in aqueous solution.

3. The method of claim 1 where the metal is a lanthanide cation.

4. The method of claim 1 where the metal is La(III), Nd(III), Sm(III), Gd(III), Tm(III), or Lu(III).

5. The method of claim 1 where the metal is Eu(III) or Dy(III).

6. The method of claim 1 where the phosphate ester is RNA.

7. A method of phosphate ester hydrolysis, comprising incubating an aqueous phosphate ester solution with a texaphyrin metal complex, said incubation being under conditions and for a time sufficient to hydrolyze the phosphate ester, wherein the texaphyrin metal complex has the structure:

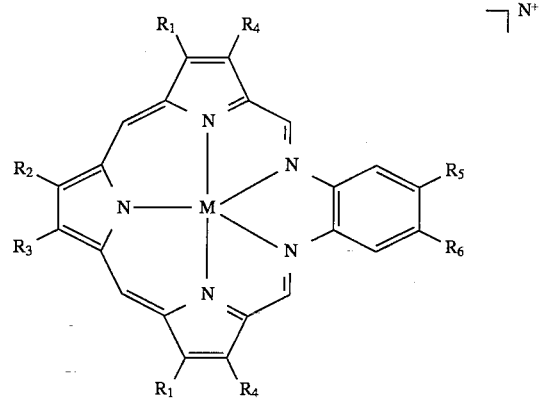

where:

M is a divalent or a trivalent metal cation having catalytic activity for ester bond hydrolysis in aqueous solution;

$R_1$, $R_2$, $R_3$, $R_4$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, a site-directed molecule or a couple to a site-directed molecule or to a catalytic group; and N is an integer less than or equal to 2.

8. The method of claim 7 where at least one of $R_1$, $R_2$, $R_3$, $R_4$, $R_5$ and $R_6$ is a site-directed molecule or is a couple to a site-directed molecule.

9. The method of claim 7 where the site-directed molecule is an oligonucleotide, a hormone, an antibody, a texaphyrin molecule, a sapphyrin molecule, or a peptide having affinity for a biological receptor.

10. The method of claim 7 where the oxyhydroxyalkyl is $C_{(n-x)}H_{((2n+1)-2x)}O_xO_y$ or $OC_{(n-x)}H_{((2n+1)-2x)}O_xO_y$ where
   n is a positive integer from 1 to 10;
   x is zero or a positive integer less than or equal to n; and
   y is zero or a positive integer less than or equal to $((2n+1)-2x)$.

11. The method of claim 7 where the oxyhydroxyalkyl or saccharide is $C_nH_{((2n+1)-q)}O_yR^a_q$, $OC_nH_{((2n+1)-q)}O_yR^a_q$ or $(CH_2)_nCO_2R^a$ where
   n is a positive integer from 1 to 10,
   y is zero or a positive integer less than $((2n+1)-q)$,
   q is zero or a positive integer less than or equal to $2n+1$,
   $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where
   m is a positive integer from 1 to 10,
   w is zero or a positive integer less than or equal to m,
   z is zero or a positive integer less than or equal to $((2m+1)-2w)$,
   R is H, alkyl, hydroxyalkyl, or $C_mH_{((2m+1)-r)}O_zR^b_r$ where
   m is a positive integer from 1 to 10,
   z is zero or a positive integer less than $((2m+1)-r)$,
   r is zero or a positive integer less than or equal to $2m+1$, and
   $R^b$ is independently H, alkyl, hydroxyalkyl, or saccharide.

12. The method of claim 7 where the carboxyamidealkyl is $(CH_2)_nCONHR^a$, $O(CH_2)_nCONHR^a$, $(CH_2)_nCON(R^a)_2$, or $O(CH_2)_nCON(R^a)_2$ where
   n is a positive integer from 1 to 10,
   $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directed molecule or a catalytic group where
   m is a positive integer from 1 to 10,
   w is zero or a positive integer less than or equal to m,
   z is zero or a positive integer less than or equal to $((2m+1)-2w)$,
   R is H, alkyl, hydroxyalkyl, or $C_mH_{((2m+1)-r)}O_zR^b_r$ where
   m is a positive integer from 1 to 10,
   z is zero or a positive integer less than $((2m+1)-r)$,
   r is zero or a positive integer less than or equal to $2m+1$, and
   $R^b$ is independently H, alkyl, hydroxyalkyl, or saccharide.

13. The method of claim 12 where $R^a$ is an oligonucleotide.

14. The method of claim 7 where the carboxyalkyl is $C_nH_{((2n+1)-q)}O_yR^c_q$ or $OC_nH_{((2n+1)-q)}O_yR^c_q$ where
   n is a positive integer from 1 to 10;
   y is zero or a positive integer less than $((2n+1)-q)$,
   q is zero or a positive integer less than or equal to $2n+1$,
   $R^c$ is $(CH_2)_nCO_2R^d$, $(CH_2)_nCONHR^d$, $(CH_2)_nCON(R^d)_2$ or a site-directed molecule or a catalytic group where
   n is a positive integer from 1 to 10;
   $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+m)-2w)}O_wO_z$, where m is a positive integer from 1 to 10,
   w is zero or a positive integer less than or equal to m,
   z is zero or a positive integer less than or equal to $((2m+1)-2w)$,
   R is H, alkyl, hydroxyalkyl, or $C_mH_{((2m+1)-r)}O_zR^b_r$ where
   m is a positive integer from 1 to 10,
   z is zero or a positive integer less than $((2m+1)-r)$,
   r is zero or a positive integer less than or equal to $2m+1$,
   and $R^b$ is independently H, alkyl, hydroxyalkyl, or saccharide.

15. The method of claim 14 where $R^c$ is an oligonucleotide.

16. The method of claim 7 wherein the phosphate ester is RNA.

17. The method of claim 7 wherein M is a lanthanide cation or a Lewis acidic cation.

18. The method of claim 7 wherein M is Lu(III), Eu(III), Dy(III), or Tb(III).

19. The method of claim 8 where the site-directed molecule is an oligonucleotide.

20. The method of claim 8 where the site-directed molecule is an oligodeoxyribonucleotide.

21. The method of claim 19 where the oligonucleotide has complementary binding affinity for oncogenes.

22. The method of claim 19 where the phosphate ester is RNA and the oligonucleotide has complementary binding affinity for the RNA in a region proximal to the phosphate ester bond being hydrolyzed.

23. The method of claim 22 where the RNA is viral RNA.

24. The method of claim 22 where the RNA is retroviral RNA.

25. The method of claim 19 where the oligonucleotide has complementary binding affinity for a bacterial nucleic acid.

26. The method of claim 25 where the bacterial nucleic acid is ribosomal RNA.

27. The method of claim 8 where $R_5$ or $R_6$ is an oligonucleotide or a couple to an oligonucleotide.

28. The method of claim 8 where $R_3$ is an oligonucleotide or is a couple to an oligonucleotide.

29. The method of claim 7 where $R_1$ is $(CH_2)_2CH_2OH$, $R_2$ and $R_3$ are $CH_2CH_3$, $R_4$ is $CH_3$, and $R_5$ and $R_6$ are $OCH_2CH_2CH_2OH$.

30. The method of claim 7 where $R_1$ is $(CH_2)_2CH_2OH$, $R_2$ and $R_3$ are $CH_2CH_3$, $R_4$ is $CH_2$, $R_5$ is $O(CH_2)_nCO$-oligonucleotide where n is 1–7, and $R_6$ is H.

31. The method of claim 30 where n is 1.

32. The method of claim 30 where n is 3.

33. The method of claim 7 where $R_1$ is $CH_2CH_2CH_2OH$, $R_2$ and $R_3$ are $CH_2CH_3$, $R_4$ is $CH_3$, $R_5$ is $O(CH_2CH_2O)_2CH_2CH_2OCH_3$ and $R_6$ is a site-directed molecule or a couple to a site-directed molecule.

34. The method of claim 33 where $R_6$ is $O(CH_2)_nCO$-oligonucleotide where n is 1–7.

35. The method of claim 19 where the oligonucleotide has complementary binding affinity for a targeted intracellular mRNA.

36. The method of claim 35 where the mRNA is transcribed from an oncogene.

37. The method of claim 35 where the mRNA encodes a growth factor.

38. The method of claim 7 where $R_1$–$R_6$ are as in FIG. 18 for texaphyrins A1–A24.

39. The method of claim 38 wherein M is a lanthanide cation or a Lewis acidic cation.

40. The method of claim 38 wherein M is Lu(III), Eu(III), Dy(III), or Tb(III).

* * * * *

UNITED STATES PATENT AND TRADEMARK OFFICE
CERTIFICATE OF CORRECTION

PATENT NO. : 5,559,207
DATED : September 24, 1996
INVENTOR(S) : Jonathan L. Sessler, Daniel A. Smith, Richard A. Miller, Kevin L. Ross, Meredith Wright, William C. Dow, Vladimir A. Kral, Brent Iverson, Darren Magda It is certified that error appears in the above-indentified patent and that said Letters Patent is hereby corrected as shown below:

In claim 30, Column 36, Line 42, delete "$R_4$ is $CH_2$" and substitute -- $R_4$ is $CH_3$ -- therefor.

Signed and Sealed this

Eighteenth Day of March, 1997

*Attest:*

BRUCE LEHMAN

*Attesting Officer*     Commissioner of Patents and Trademarks